(12) United States Patent
Pickard

(10) Patent No.: US 9,541,476 B2
(45) Date of Patent: Jan. 10, 2017

(54) CRYO-PREPARATION SYSTEMS AND METHODS FOR NEAR-INSTANTANEOUS VITRIFICATION OF BIOLOGICAL SAMPLES

(71) Applicant: NATIONAL UNIVERSITY OF SINGAPORE, Singapore (SG)

(72) Inventor: Daniel Shawn Pickard, Singapore (SG)

(73) Assignee: National University of Singapore, Singapore (SG)

( * ) Notice: Subject to any disclaimer, the term of this patent is extended or adjusted under 35 U.S.C. 154(b) by 142 days.

(21) Appl. No.: 13/261,966

(22) PCT Filed: Apr. 4, 2013

(86) PCT No.: PCT/US2013/035341
§ 371 (c)(1),
(2) Date: Oct. 4, 2014

(87) PCT Pub. No.: WO2013/152239
PCT Pub. Date: Oct. 10, 2013

(65) Prior Publication Data
US 2015/0147778 A1    May 28, 2015

Related U.S. Application Data

(60) Provisional application No. 61/620,426, filed on Apr. 4, 2012.

(51) Int. Cl.
| | |
|---|---|
| *A61B 10/00* | (2006.01) |
| *G01N 1/30* | (2006.01) |
| *G01N 1/42* | (2006.01) |
| *G01N 1/44* | (2006.01) |
| *G02B 21/36* | (2006.01) |
| *G02B 21/34* | (2006.01) |
| *B01L 3/00* | (2006.01) |

(52) U.S. Cl.
CPC ................ *G01N 1/30* (2013.01);
*G01N 1/42* (2013.01); *G01N 1/44* (2013.01);
*G02B 21/34* (2013.01); *G02B 21/361* (2013.01); *B01L 3/5027* (2013.01)

(58) Field of Classification Search
CPC ................ G01N 1/30; B01L 3/5027
See application file for complete search history.

(56) References Cited

U.S. PATENT DOCUMENTS

| | | |
|---|---|---|
| 4,839,194 A | 6/1989 | Malluche et al. |
| 6,300,130 B1 | 10/2001 | Toner et al. |
| 2011/0108548 A1 | 5/2011 | Nobue et al. |
| 2011/0229928 A1 | 9/2011 | Dorward et al. |

*Primary Examiner* — Jyoti Nagpaul
(74) *Attorney, Agent, or Firm* — Blakely Sokoloff Taylor & Zafman LLP

(57) ABSTRACT

A sample vitrification system includes a capsule structure configured for carrying a biological sample within a compartment while the sample is subjected to ultra-rapid freezing by way of a cryogenic coolant jet, and while the sample is exposed to pulsed microwave radiation in a manner that disrupts water molecule pentamer formation and which disrupts initial ice crystal nucleation events within the compartment within tens of microseconds to provide a vitrification depth within the compartment of tens of microns or more. The sample can reside between a very high thermal conductivity substrate and a cover. The cryogenic coolant jet is applied to the substrate from beneath the sample. The cover can carry a set of microwave excitation elements configured for providing microwave radiation to internal portions of the compartment. Portions of the capsule structure's interior can be imaged during microwave assisted jet freezing, such as by way of an optical microscope.

35 Claims, 40 Drawing Sheets

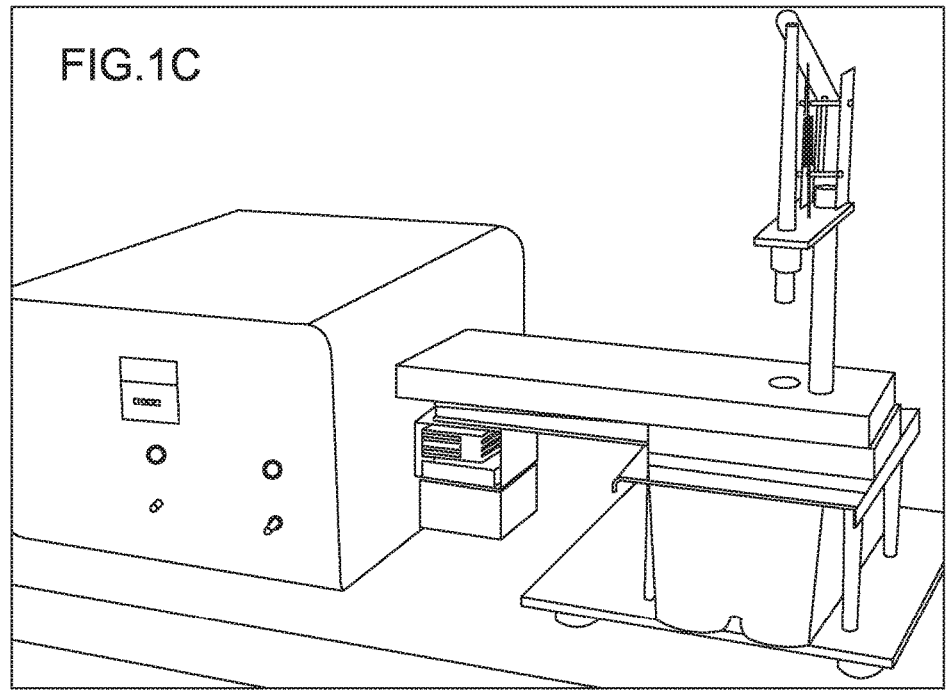
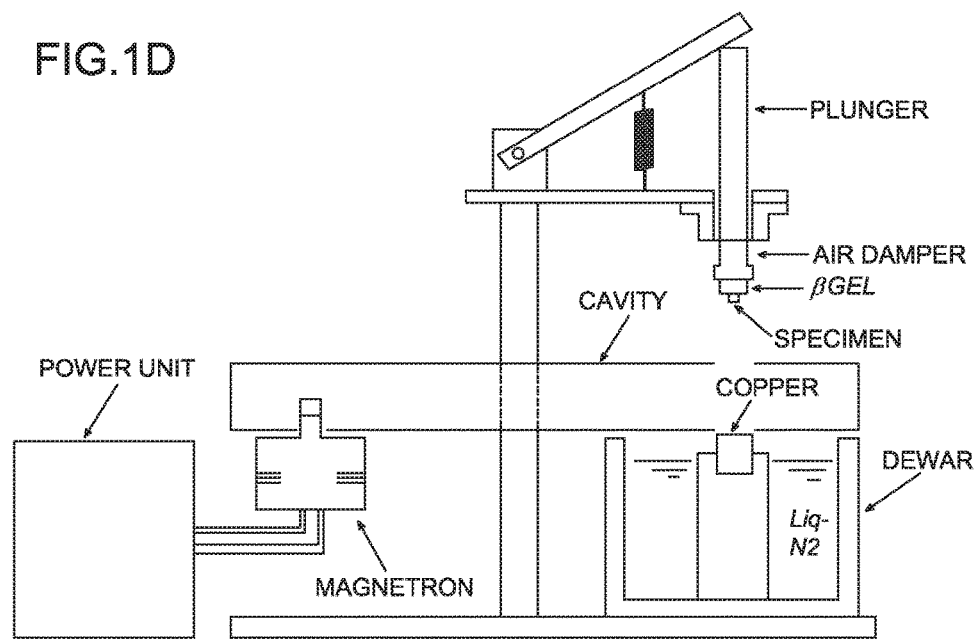

3D VIEW OF MICROWAVE COPLANAR FEED AND LIQUID SPECIMEN (TOP PCB REMOVED)

END VIEW OF MICROWAVE COPLANAR FEED AND LIQUID SPECIMEN

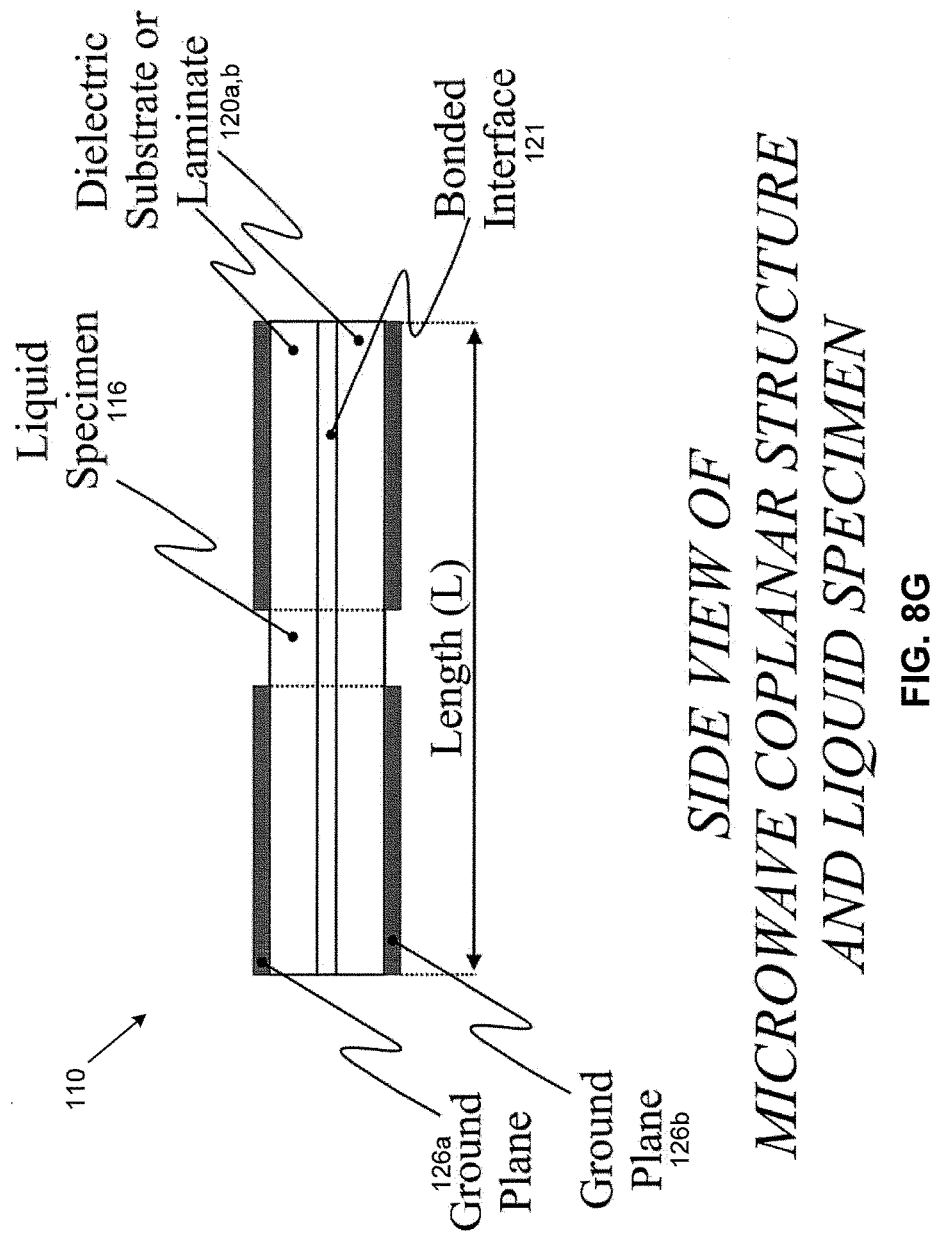

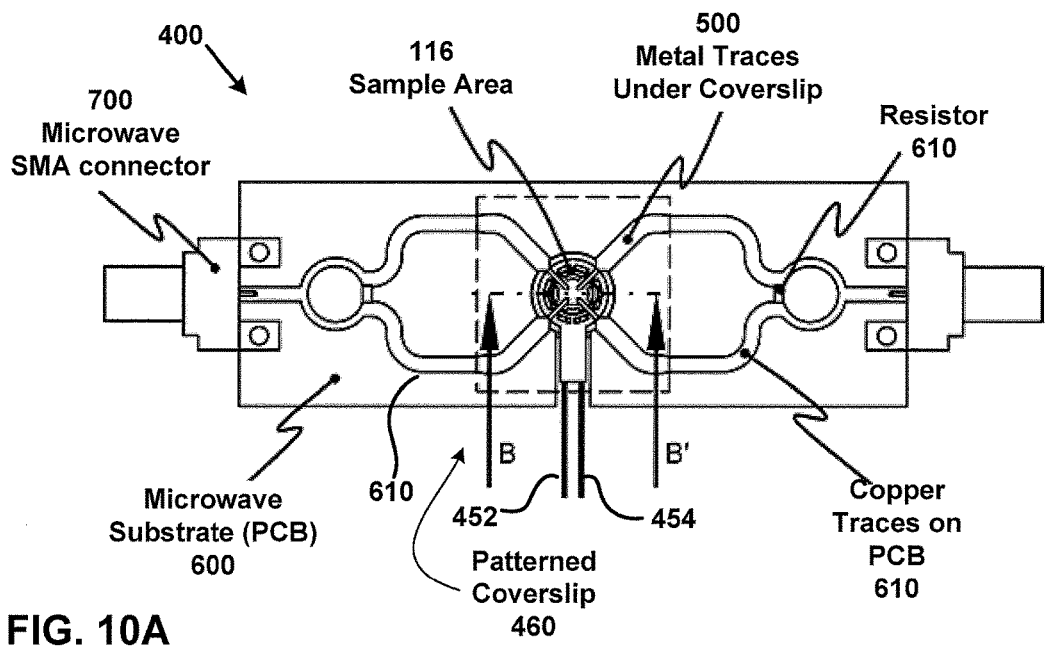
FIG. 10A
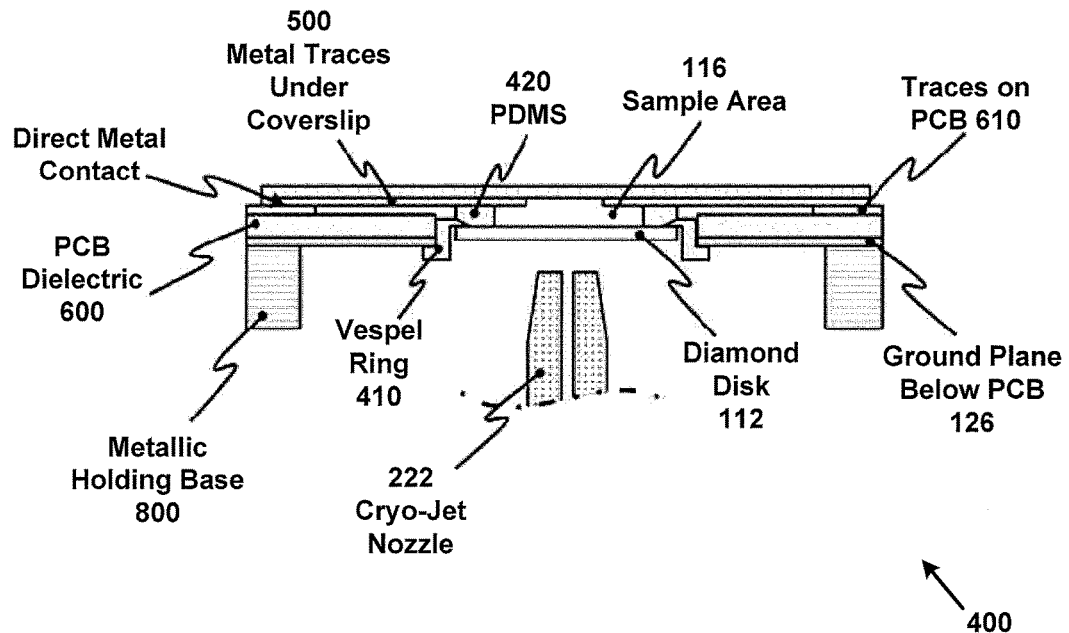
FIG. 10B  PARTIAL SECTION B-B'

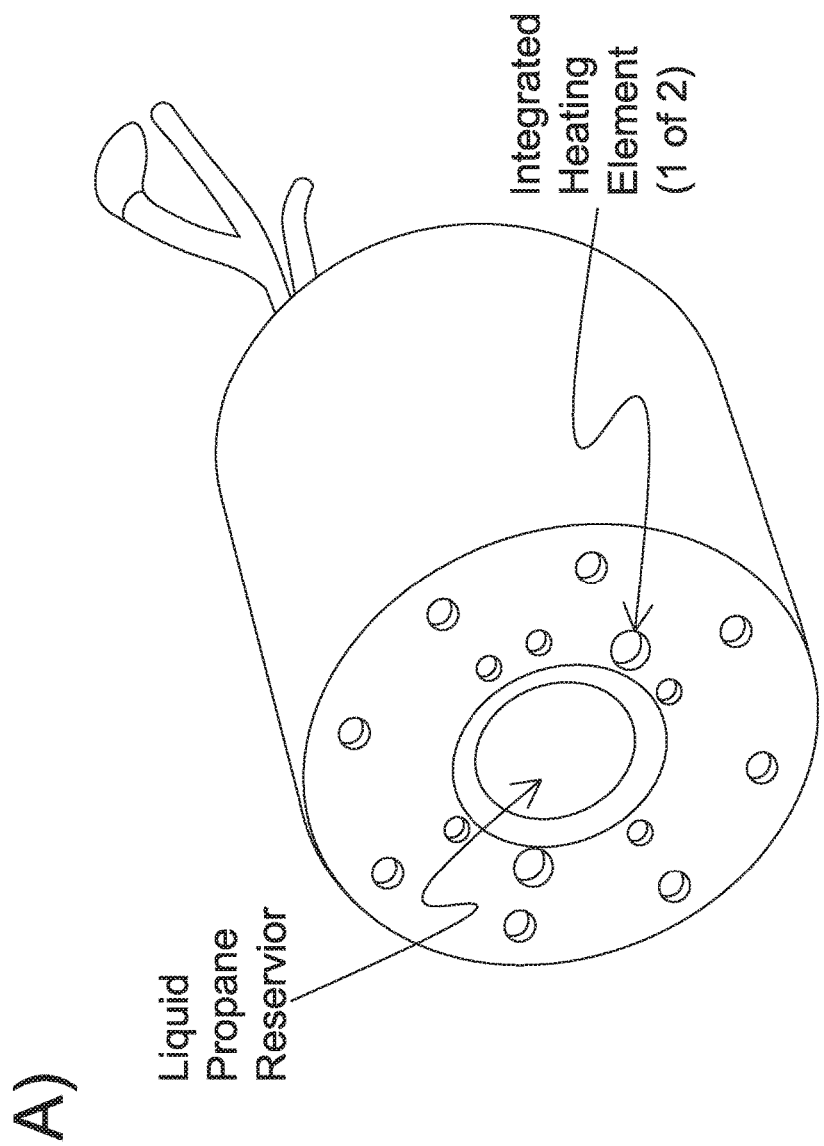

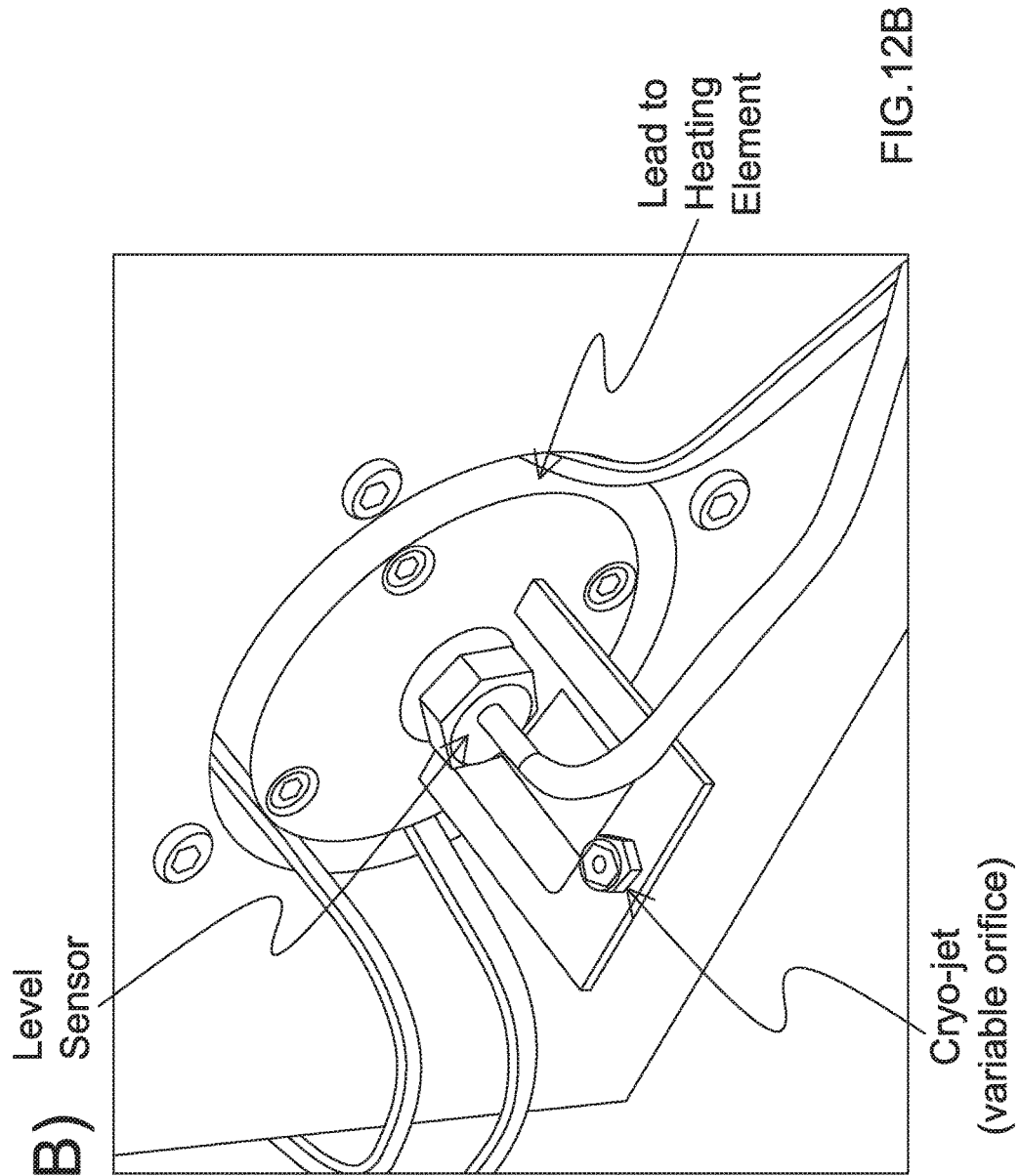

D)

E)

F)

G)

H)

I)

CRYO-PREPARATION SYSTEMS AND METHODS FOR NEAR-INSTANTANEOUS VITRIFICATION OF BIOLOGICAL SAMPLES

TECHNICAL FIELD

The present disclosure relates generally to techniques for selectively applying microwave energy to biological samples in association with preparing such samples for imaging, analysis, and/or processing. More particularly, aspects of the present disclosure are directed to systems, apparatuses, devices, and processes for selectively applying microwave and/or other energy to biological and/or other samples during sample vitrification procedures.

BACKGROUND

The study of biological specimens with charged particles remains integral to the advancement of the biological sciences owing to its superior resolution compared to optical techniques. However, such systems work in a vacuum environment so typically the specimens must be chemically altered and dehydrated prior to imaging. This presents an obstacle to obtaining reliable information because faithful imaging depends critically on the sample preparation technique and all dehydration techniques produce artifacts (protein loss, shrinkage etc).

Imaging specimens in a pristine hydrated state (even in vacuum) is possible if the sample is frozen, but care must be taken to avoid the formation of ice crystals which cause disruption of the cellular structure. Typically, techniques currently employed attempt to decrease the temperature of the specimen below the freezing point faster than ice crystals can propagate in the media (a cooling rate of approximately 10,000 degrees Kelvin/sec is required), and thus a crystal-free amorphous or "vitreous" region free of artifacts can be achieved. However, the range of environmental conditions under which vitrification can occur is extremely limited and current cryo-preparation techniques have major shortcomings. For example, in slam freezing, where the sample is forced on a cold metal block (Liquid Nitrogen, LN, temperature or colder), the vitreous region is limited to about 5 microns in depth. This is because of the limited thermal conductivity of the water in the sample. Often the features of interest exist deeper than this shallow vitreous region, and hence such features of interest are subject to extensive crystal damage. Moreover, even a thin layer of water on the sample surface can take up a significant fraction of this vitreous region, providing limited or no information about the sample whatsoever. A much more effective approach is to freeze the samples under extremely high pressures of approximately 2100 bar (i.e., about 30,000 psi), where the freezing temperature of water is depressed and the propagation speed of the crystal growth is significantly reduced due to viscosity changes within the material. High pressure freezing is currently a type of "gold standard" for sample preparation, providing vitreous regions having a depth of up to approximately 200 microns within the sample. Unfortunately, high pressure freezers are undesirably expensive (approximately $250,000 USD), and they require delicate, time consuming sample preparation prior loading into the freezer.

As described in "An improved cryofixation method: cryoquenching of small tissue blocks during microwave irradiation," *J. Microsc.* 165, 255-271 (1992), Hanyu et al. found that a vitreous region within a sample undergoing slam freezing could be extended to 15 microns using a microwave assisted slam freezing technique, in which continuous wave (CW) microwave energy was provided in a manner that disrupted the aggregation of water molecules which into pentamer structures (breaking them into monomers) immediately before the onset of a freezing wave, as indicated in FIG. 1A. Hanyu found that microwave assisted disruption of nucleation sites significantly extended the depth of vitrification, and also changed the character of the ice crystals which formed beyond the vitrified zone. More particularly, as indicated in FIG. 1B, at depths beyond 15 microns, the crystals remained substantially smaller (bounded to less than 50 nm) than in the control-case without microwave disruption (where the crystal size increased without bound beyond 5 microns depth).

Hanyu's apparatus, which is shown in FIGS. 1C and 1D, exposed the sample to microwave radiation as the sample underwent free-fall through a waveguide cavity. The exposure of Hanyu's sample to microwave radiation thus occurred during the time it took the sample to free-fall through the cavity, just prior to impinging on a LN cooled copper block disposed beyond a lower border of the cavity. Unfortunately, Hanyu's apparatus was undesirably limited with respect to the manner in which applied microwave energy interacted with the propagation of a freezing wave within the sample. Furthermore, Hanyu's apparatus was quite cumbersome in terms of its size, configuration, and difficulty of integration with standard microscopy systems or microscopes, and lack of scalability. Additionally, Hanyu's cooling head needed to be re-heated and polished between each sample, so Hanyu's apparatus is not well suited to correlative microscopy.

A need exists for a system, apparatus, device and method that provides greatly improved performance over slam or plunge freezing by way of the selective application of microwave energy to a sample during slam freezing, which provides vitrification depths of up to tens of microns or more, which can be readily integrated with standard types of microscopy equipment (e.g., optical microscopes), which is well-suited for correlative microscopy, and which has a cost that is much lower than current high pressure devices.

SUMMARY

Embodiments in accordance with the present disclosure provide systems, apparatuses, devices, and procedures for advancing the state-of-the-art of cryo-preparation by way of applying pulsed microwave energy (for instance, between approximately 2.0-18 GHz, e.g., approximately 2.45 GHz, 5.0 GHz, 5.8 GHz, 8.0 GHz, or 10 GHz; and/or another frequency) to a sample or specimen as it is very rapidly cooled in a manner that substantially or essentially entirely avoids ice crystal formation within the sample, thereby managing, controlling, and/or increasing the depth of vitrification within the sample. The timing and power density of the microwave energy are provided in a manner that disrupts water molecules which have aggregated into a pentamer structure (breaking them into monomers) immediately before the onset of a freezing wave. More particularly, various embodiments in accordance with the present disclosure are configured for the application of a microwave signal pulse train that includes multiple high power pulses, but which has low average power, to the sample. Embodiments in accordance with the present disclosure can thus at least substantially minimize, avoid, or prevent the formation of ice crystals within portions of the sample.

Various embodiments in accordance with the present disclosure can provide vitrification depths up to tens of microns or more, at a cost that is much lower (e.g., ten times lower) than current high pressure devices, and can enable a near instantaneous freeze of the specimen (within tens of microseconds) after a key, trigger, or target event is initialized, initiated, or observed. Embodiments in accordance with the present disclosure can be compact or highly compact, and can be readily integrated with or retrofitted onto existing instruments such as optical microscopes, which along with charged particle systems are ubiquitous in universities and research institutions. Systems, apparatuses, and devices in accordance with embodiments of the present disclosure are well suited to and can thus greatly increase the utility of correlative microscopy. Consequently, embodiments in accordance with the present disclosure can become integral elements in the rapidly expanding field of correlative microscopy, which has an estimated annual market exceeding approximately $70M USD for charged particle optics instruments in correlative biological applications, corresponding to roughly 200 or more instruments per year.

FIG. 2A is a schematic illustrations showing particular portions of a sample preparation, fixation, processing, observation, and/or examination system 10 in accordance with an embodiment of the present disclosure. The system 10 includes a carrier or capsule structure 110 configured for carrying, holding, or retaining one or more samples or specimens (e.g., a sample disposed within or carried by a liquid) within a recess, chamber, or compartment 116 while the sample is subjected to ultra-rapid freezing by way of exposure to a cryogenic coolant jet 220. The capsule structure 110 can include or be coupled to a very high or extremely high thermal conductivity substrate 112, such as a diamond or sapphire material, to facilitate extremely rapid thermal energy transfer; and a cover 114, such that the sample resides between the substrate 112 and the cover 114. Portions of the capsule structure 110 can further be exposed to, support, carry, or include a set of microwave energy application or microwave signal delivery elements 122, which can provide microwave signals to internal portions of the compartment 116, and hence to the sample, during an ultra-rapid or jet freezing procedure. In some embodiments, one or more portions of the compartment's interior can be viewed or imaged during freezing, such as by way of a microscope objective 55. The capsule structure 110 itself can be matingly or removably coupled to a panel, platform, or stage structure, such as a microscope stage or platform. In a number of embodiments, one or more portions of the capsule structure 110 can be disposable.

To understand aspects of the motivation underlying particular embodiments in accordance with the present disclosure, a more detailed examination of sample or specimen cooling is required. FIG. 2B is a schematic illustration of representative regions within a sample as the sample undergoes ultra-rapid or jet freezing. In FIG. 2B, Region I corresponds to a diamond substrate 112 which is at LN temperature; Region II corresponds to an initial vitrified frozen interface, which is dynamic and propagating; Region III corresponds to unfrozen, pre-cooled liquid in proximity to the frozen interface; Regions IV and V correspond to the remaining aqueous solution; and Region VI corresponds to the cover 114, through which the sample can be imaged.

Without microwave disruption, the cooling rate and the advance of the frozen interface can be calculated with basic thermodynamic and heat transfer equations. Ideally, within the first 5 microns and approximately 5 microseconds, the cooling rates (e.g., approximately 10,000 K degrees/sec) are sufficient for vitrification. As time progresses, the low thermal conductivity of the sample in Region II degrates the cooling rate substantially. The pre-cooling exacerbates the problem because the concentration of water pentamers increases dramatically as the temperature is reduced. For example, at 298K water consists of approximately 85% pentamers (Ohtomo et al, 1982). Hanyu's approach disrupted the pentamers; however, the molecular relaxation time is much faster than the propagation times of the cooling front (milliseconds), so the nucleation sites reform rapidly, particularly in pre-cooled Region III. Continuous-Wave (CW) application of microwaves is an option, but since the microwave absorption cannot be avoided in Region IV, the power density must be limited to prevent sample heating and degradation.

In FIG. 2B, the aqueous region has been partitioned, and the interface between Regions IV and V (about 50 microns from the substrate) represents the plane at which more rapid cooling at the substrate 110 no longer improves the cooling rate in Region V (as long as it is above a threshold of approximately 5K-10K degrees/sec). That is, even an infinite cooling rate in Region I will not improve the cooling rate in Region V because the thermal diffusion has become limited by the lower diffusivity of the vitrified sample. This is a consequence of the diffusion process, where the diffusion time depends upon distance squared. One additional noteworthy property is that the thermal diffusivity of the vitrified region is lower than that of water, so the pre-cooled region expands faster than the propagation of the vitrified interface.

Various embodiments in accordance with the present disclosure are intended to overcome these limitations, so that much greater peak power densities can be employed at the critical interface the instant before freezing. Additionally, by controlling the duty factor, detrimental thermal effects in Regions IV and V can be mitigated.

An appropriate choice of microwave irradiation frequency also protects the vitrified region of the sample (Region II) from inadvertent heating and re-melting. Appropriate microwave excitation isolates a particular mode of energy transfer which involves only the rotation of the molecules around their dipole. This rotational excitation is extremely effective at breaking the pentamers. Once the molecules are frozen in the vitreous region they lack the ability to rotate, and their absorption of microwave energy decreases by 3 to 4 orders of magnitude. This enables a more aggressive application of microwave peak power, as heating of the aqueous solution is limited only by the time averaged microwave power.

FIG. 2C is a graph indicating the imaginary part of the Index of Refraction for water and ice relative to the frequency or wavelength of applied radiation. As can be seen in FIG. 2C, the efficiency of microwave coupling to the water increases with frequency up to about 18 GHz, agreeing well with the classic debye model for this dielectric system. Additionally, the dimensions of microwave applicators or microwave signal delivery elements decreases with higher frequency, providing for a more compact apparatus, suggesting operation near 18 GHz is desirable. However, these trends should be balanced relative to the availability of low cost microwave power sources (e.g., WiFi components), and available license-free ISM (Industrial, Scientific, and Medical), frequency bands, three of which are shown in FIG. 2C (i.e., 2.45 GHz, 5.8 GHz, and 10 GHz). Multiple embodiments in accordance with the present disclosure are configured for providing microwave sample excitation at approximately 5.8 or 10 GHz; however, other embodiments can be configured for higher frequency excitation.

In various embodiments, the microwave pulse characteristics (e.g., amplitude, pulse duration, and/or inter-pulse interval or period between pulses) are managed, controlled, tailored, or optimized to substantially or essentially match the velocity of the propagating freezing front and the extent of the pre-cooled region, and are applied in a sequence that is sufficiently rapid to disrupt nucleation events before they occur, become established, or propagate, for instance, by way of dendritic growth, which has been found by Stan et. al in "Apparatus for the Study of Ice Nucleation in Supecooled Water Drops," *Lab Chip*, 2009, 9, 2293-2305, to be the first stage of ice crystal formation that is initiated in supercooled water drops within tens of microseconds, and which is completed within 300 microseconds. Nonuniform dendritic growth is followed by a uniform freezing phase from outer edges of a sample toward sample center, and lasts an additional tens of milliseconds. In various embodiments in accordance with the present disclosure, specimen or sample thickness can be up to approximately 200 microns, so a freezing process can last up to approximately 100 milliseconds. Embodiments in accordance with the present disclosure can apply pulsed microwave signals in a manner that substantially or effectively reduces, minimizes, or arrests initial nucleation events within tens of microseconds. In certain embodiments, one or more of the aforementioned parameters can change during the progression of the freeze.

Prior ultra-rapid freezing techniques undesirably freeze a sample from a top exposed surface, either by slamming the specimen onto a polished metal block (e.g., slam freezing) or by plunging it into a cryocoolant. This presents many difficulties, of which the most pressing is the requirement to blot the aqueous solution from the surface prior to the freeze. The blotting procedure can lead to inconsistent results, given that an aqueous film of only 5-10 microns would consume most or all of a limited vitrified region. It is also time-consuming, eliminating the possibility of "freezing" rapid events. Approaches in accordance with embodiments of the present disclosure cool the sample underneath, that is, from a substrate side, for instance, using a super-cooled propellant jet (liquid ethane at LN temperatures, or one or more other cryocoolants). This eliminates the problems of a water layer, allowing for in-situ imaging immediately preceding, during, and after the freeze. Cells, bacteria, or other biological specimens carried by the substrate can remain submerged in a buffer layer such as an aqueous buffer, since the important information is tied directly to the substrate 112 and crystal growth in the aqueous buffer is inconsequential. This also allows for studies which can lock-in a condition a few milliseconds after an observed or triggering event.

Substrates 112 configured for carrying or thermally interfacing with samples in accordance with embodiments of the present disclosure provide a very high or extremely high thermal conductivity. Multiple embodiments employ thin re-usable optical grade diamond substrates, while other embodiments can employ other types of substrates (e.g., sapphire). Diamond has the highest thermal conductivity of any material, far surpassing that of copper, the best metallic conductor. The heat transfer mechanism of diamond is also fundamentally different than that of metals, conducting heat through phonons rather than electrons, and provides enhanced conductivity near LN temperatures. Optical diamond substrates are commercially available and relatively inexpensive (e.g. available at element six, www.e6cvd.com). Reuse of the substrates 112 is possible with simple cleaning procedures between uses. The substrates 112 are bio-compatible and can be configured with fiducial markers, either through metallized patterns or etching, so that specific regions of interest can be identified trivially by the markers as the sample transitions from optical to charged particle instruments.

A number of elements or components in accordance with embodiments of the present disclosure can be miniaturized to adapt to or fit in a standard, replaceable panel, platform, or stage on an optical microscope (e.g., an upright microscope configuration). In accordance with embodiments of the present disclosure, a set of microwave excitation or signal application elements is compact and does not significantly interfere with either an objective lens above or a light illumination source below the sample chamber or capsule. Multiple types of microwave signal delivery elements can be configured to apply microwave energy to a sample within a chamber in accordance with embodiments of the present disclosure, for instance, strip lines and a slab-line elements (e.g., which can be coupled to coaxial cables).

Additionally, in various embodiments an appropriate cryocoolant delivery system design is utilized, which can substantially or essentially entirely avoid interference with an illumination source below the sample, and which remains in a non-contact mode prior to cooling (to prevent pre-cooling of the sample) during optical studies. The fluid dynamics as cryocoolant is ejected from a nozzle facilitate or assure minimal stagnation points and highly uniform cooling across relevant portions of the substrate back plane or the entire substrate back plane. Geometrical aspects of a substrate 112 can be configured in one or more manners to provide an effective or maximum cooling rate, but with sufficient structural stability so that it does not warp the substrate 112 as it is cooled. Several embodiments can empty substrates 112 having a thickness of 0.5 mm or less.

BRIEF DESCRIPTION OF THE DRAWINGS

FIGS. 1C and 1D illustrate a microwave assisted slam freezing apparatus described by Hanyu et al.

FIGS. 8E-8G are schematic illustrations of a coplanar microstrip capsule structure or assembly in accordance with an embodiment of the present disclosure.

FIGS. 10A-10B schematic illustrations of further aspects of the microstrip-based capsule structure of FIGS. 9A-9D in accordance with an embodiment of the disclosure.

FIGS. 12A and 12B are images of a particular type of commercially available cryo-condenser suitable for providing a cryo-coolant jet in accordance with an embodiment of the present disclosure.

DETAILED DESCRIPTION

Figure 1A:
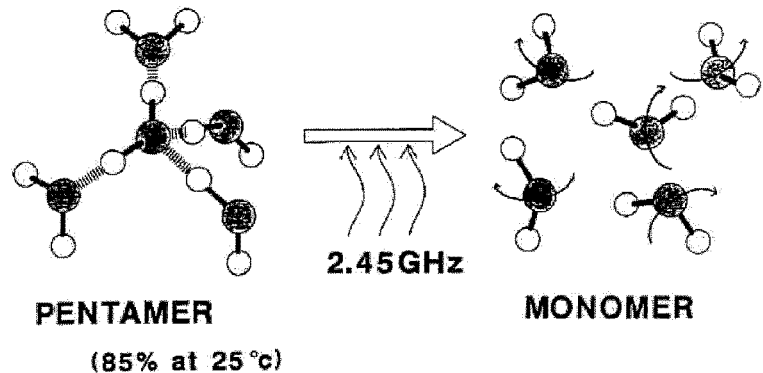
FIG. 1A is an illustration of a disruption of water molecule pentamer structures into monomer structures.
Figure 1B:
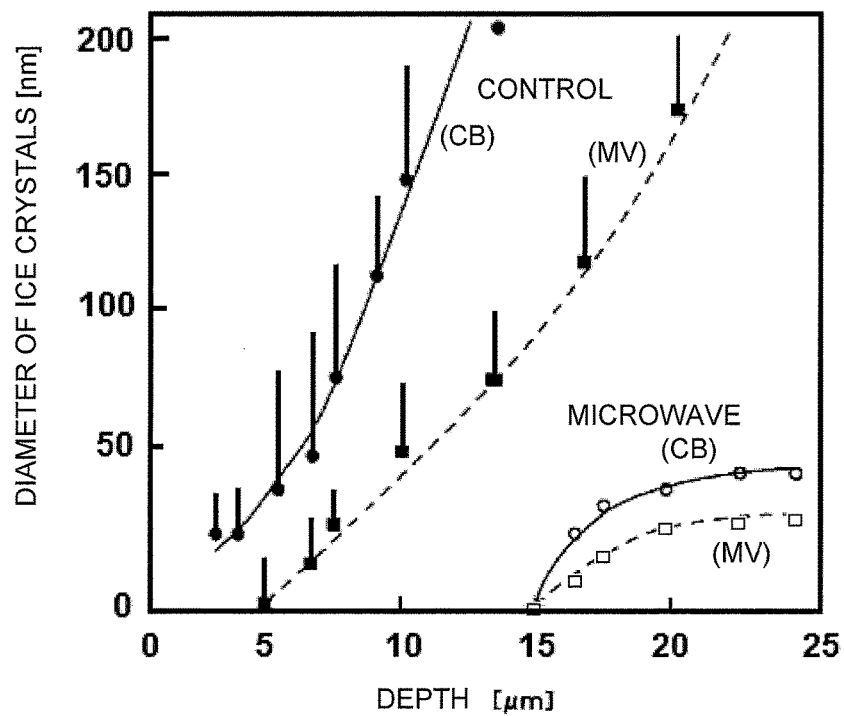
FIG. 1B is a graph illustrating microwave assisted slam freezing results described by Hanyu et al.
Figure 2A:
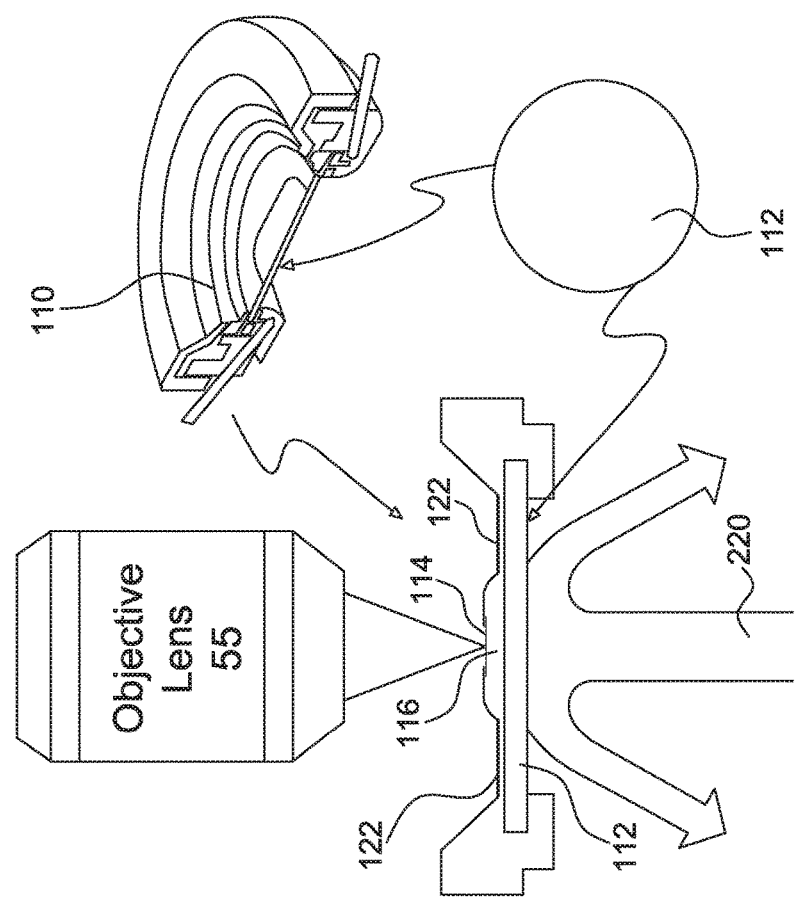
FIG. 2A is a schematic illustrations showing particular portions of a sample preparation, fixation, processing, observation, and/or examination system 10 in accordance with an embodiment of the present disclosure.
Figure 2B:
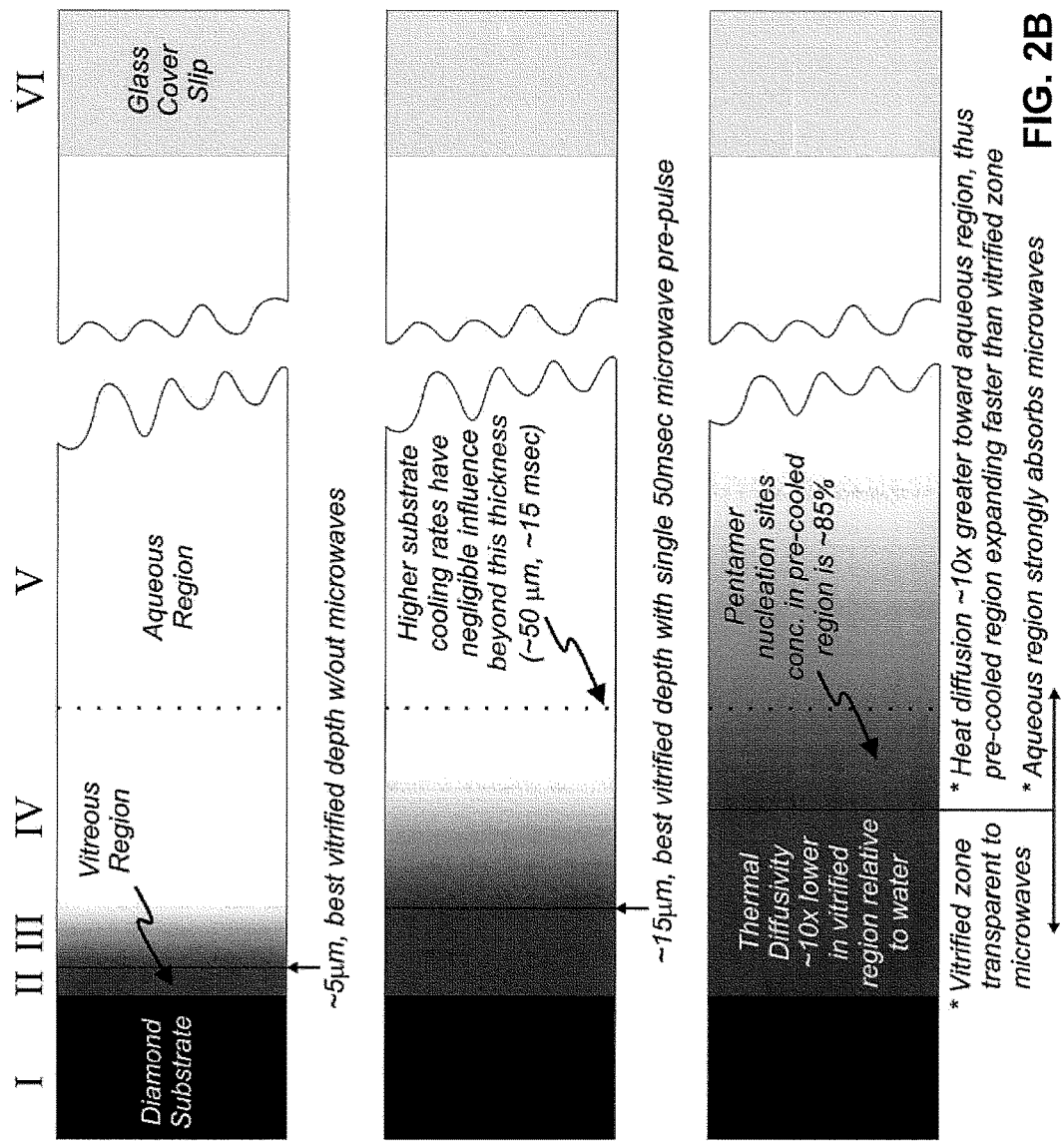
FIG. 2B is a schematic illustration of representative regions within a sample as the sample undergoes ultra-rapid freezing.
Figure 2C:
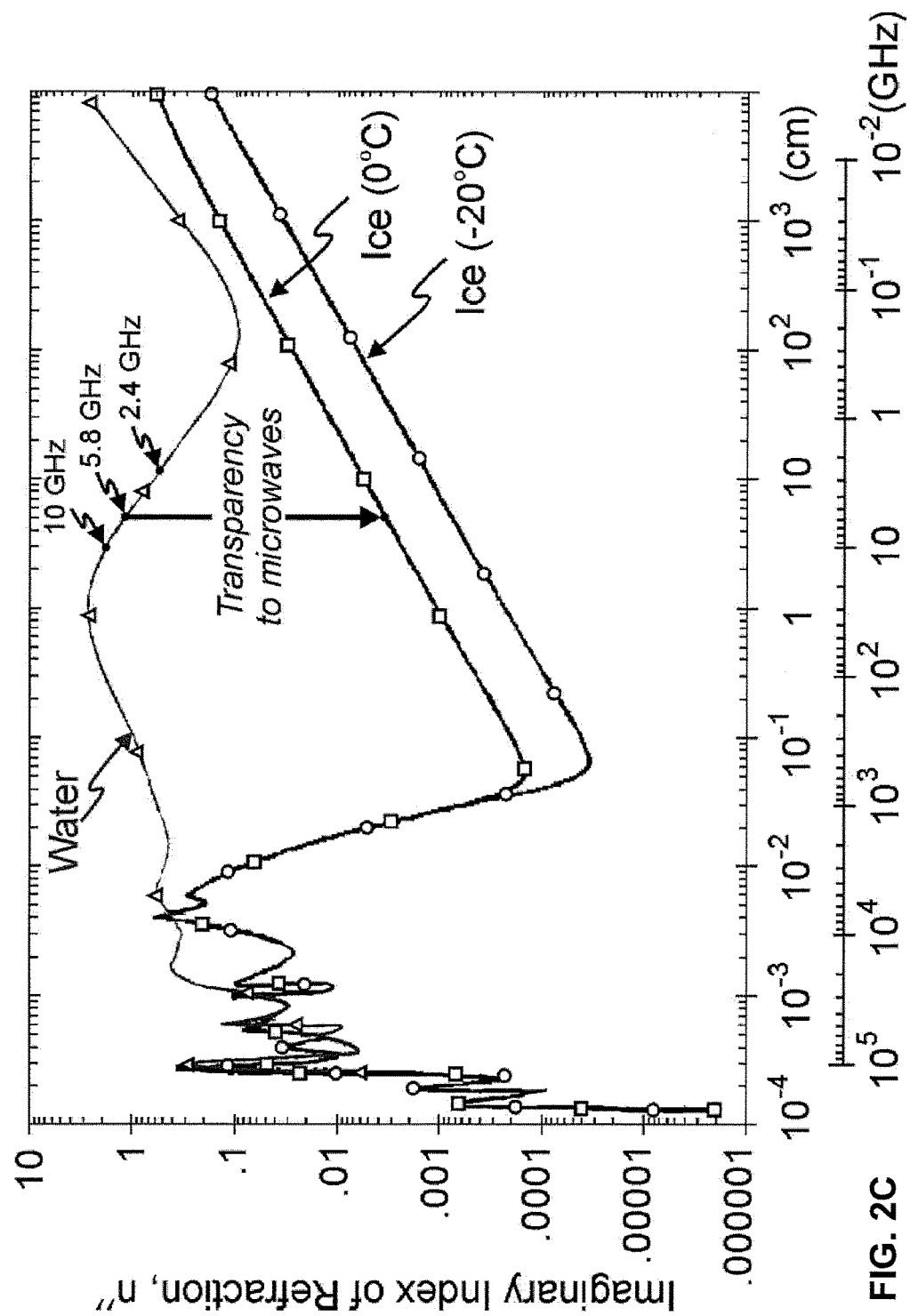
FIG. 2C is a graph indicating the imaginary part of the Index of Refraction for water and ice relative to the frequency or wavelength of applied radiation.

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in a FIG. or associated text is understood to mean "and/or" unless otherwise indicated. Additionally, unless explicitly stated otherwise, in the description herein, the recitation of particular numerical values or value ranges is taken to be a recitation of particular approximate numerical values or approximate value ranges.

As used herein, the term "set" corresponds to or is defined as a non-empty finite organization of elements that mathematically exhibits a cardinality of at least 1 (i.e., a set as defined herein can correspond to a singlet or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, a structural feature, an object, a process, a physical parameter, or a value depending upon the type of set under consideration.

Embodiments of the present disclosure are directed to systems, apparatuses, devices, and processes configurable or configured for controllably and/or selectively applying electromagnetic energy, which in various embodiments includes or is microwave energy, to a specimen, object, or sample (e.g., a biological sample) during a sample preparation or fixation process. In various embodiments, a sample preparation process includes or is a vitrification process involving rapid or extremely rapid sample cooling, e.g., at an initial cooling rate on the order of approaching, at least substantially equal to, or greater than 10,000 degrees Kelvin per second. During such a vitrification process, microwave energy (e.g., pulsed microwave energy) can be directed or applied to a sample in particular manners to affect or perturb water molecule dipole rotation energies in order to manage, reduce, disrupt, or substantially eliminate the formation of molecular $H_2O$ aggregates (e.g., $H_2O$ pentamer structures) associated with ice crystal formation. Consequently, ice crystal formation within the sample can be at least substantially avoided or eliminated. Some embodiments in accordance with the present disclosure are additionally or alternatively configurable or configured for performing related or other types of sample preparation or fixation processes (e.g., on a stand-alone basis, or on a selectable/combinable basis with respect to sample vitrification processes such as those described herein), for instance, freeze substitution processes.

Various embodiments in accordance with the present disclosure include at least some of (a) a carrier or capsule structure, assembly, device, or element, each of which is configured for carrying, housing, retaining, or holding a sample or specimen, and each of which includes at least one high or very high thermal conductivity surface, substrate, or support member configured for thermal communication or thermal energy transfer with a sample within the capsule; (b) an electromagnetic signal application apparatus, device, circuit, or structure configured for selectively delivering or applying electromagnetic energy or signals, such as microwave frequency signals, electromagnetic fields, or radiation, to or through portions of a capsule in which a sample resides; and (c) a cooling system, apparatus, device, or unit configured for rapid or extremely rapid capsule cooling, such as by way of an application of at least one cryocoolant stream or jet to a capsule's high/very high thermal conductivity substrate. Various embodiments in accordance with the present disclosure further include or are configured for use with an imaging system, such as an optical microscopy system, which can capture images of a sample before, during, and/or after a sample preparation or fixation process.

Depending upon embodiment details, particular portions of a sample carrier, an electromagnetic signal application apparatus, and/or a cooling apparatus can be combined or integrated, for instance, in one or more representative manners described below. Furthermore, in multiple embodiments, one or more portions of a sample carrier, an electromagnetic signal application apparatus, and/or a cooling apparatus can form a modular sample preparation or fixation apparatus or unit that can be combined or integrated with or adapted to a microscope configured for reflectance and/or transmission microscopy; a fluorescence microscope, such as a total internal reflection fluoroscopy (TIRF) microscope; a laser scanning confocal microscope; or another type of microscope. In a representative implementation, a sample preparation or fixation apparatus in accordance with an embodiment of the present disclosure can be combined or integrated with or adapted to a commercially available microscope such as a Zeiss Axio Imager Vario microscope.

Aspects of particular representative embodiments in accordance with the present disclosure are described in detail hereafter. Such representative embodiments are not intended to limit the scope of the present disclosure and/or any claims based thereupon. Unless defined otherwise, all technical and scientific terms used herein have the same, essentially the same, or an analogous meaning as technical and scientific terms commonly understood by one of ordinary skill in the relevant art.

Aspects of Representative System Embodiments

Figure 3A:
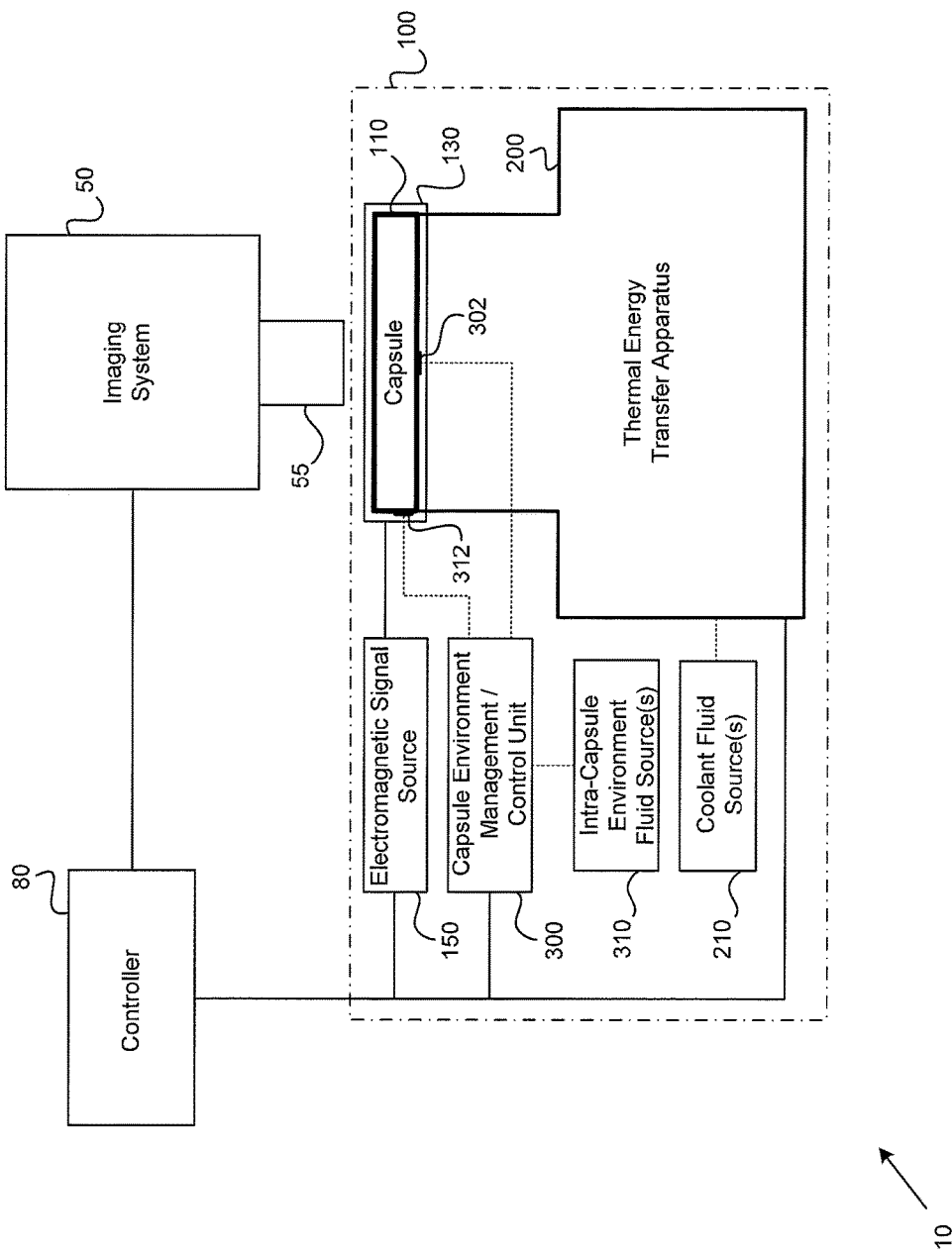
FIG. 3A is a schematic illustration of a sample preparation, fixation, processing, observation, and/or examination system in accordance with an embodiment of the present disclosure.

FIG. 3A is a schematic illustration of a sample preparation, fixation, processing, observation, and/or examination system 10 in accordance with an embodiment of the present disclosure. In an embodiment, a sample preparation, fixation, processing, observation, and/or examination system 10 includes a sample preparation or fixation apparatus 100 having a capsule structure, assembly, device, or element (hereafter capsule or sample capsule) 110; a set of electromagnetic signal delivery elements 130; at least one electromagnetic signal source 150; a thermal energy transfer apparatus 200; and a capsule environment management/control unit 300. Various embodiments of the system 10 further include an imaging system, apparatus, or device 50, such as a microscopy system having a set of optical and/or imaging elements 55 such as one or more objective lenses and/or imaging devices (e.g., an image capture device such as a CCD camera, which can be coupled to a computer system having a display device). The system 10 can also include a controller 80 (e.g., a computer system, a microcontroller, or other type of programmable or programmed device), which can be configured for communicating with or controlling the electromagnetic signal source 150, the thermal energy transfer apparatus 200, the capsule environment control unit 300, and possibly the imaging system 50.

The sample preparation or fixation apparatus 100 can include a set of coolant fluid sources 210 configured for fluid communication with the thermal energy transfer apparatus 200; and a set of intra-capsule environment fluid sources 310 configured for fluid communication with interior portions of the capsule 110. The capsule environment control unit 300 can be configured to monitor, measure, manage, and/or control particular aspects of the capsule's internal and/or external environment. For instance, the capsule environment control unit 300 can monitor one or more capsule temperatures, for instance, by way of a set of temperature sensing elements or probes 302 such as a number of thermocouples coupled to or carried by portions of the capsule 110 (e.g., thermocouples distributed in a predetermined pattern relative to an interior or exterior portion, region, or surface of the capsule 110). The capsule environment control unit 300 can also facilitate, manage, or control the flow of one or more substances and/or fluids (e.g., one or more of a gas such as air, nitrogen, or argon; a liquid such as water or a growth medium; and a chemical substance intended to trigger a reaction, response, or event within a sample) into/out of the capsule 110 by way of a set of valves, openings, channels, conduits, and/or passages 312.

Figure 3B:
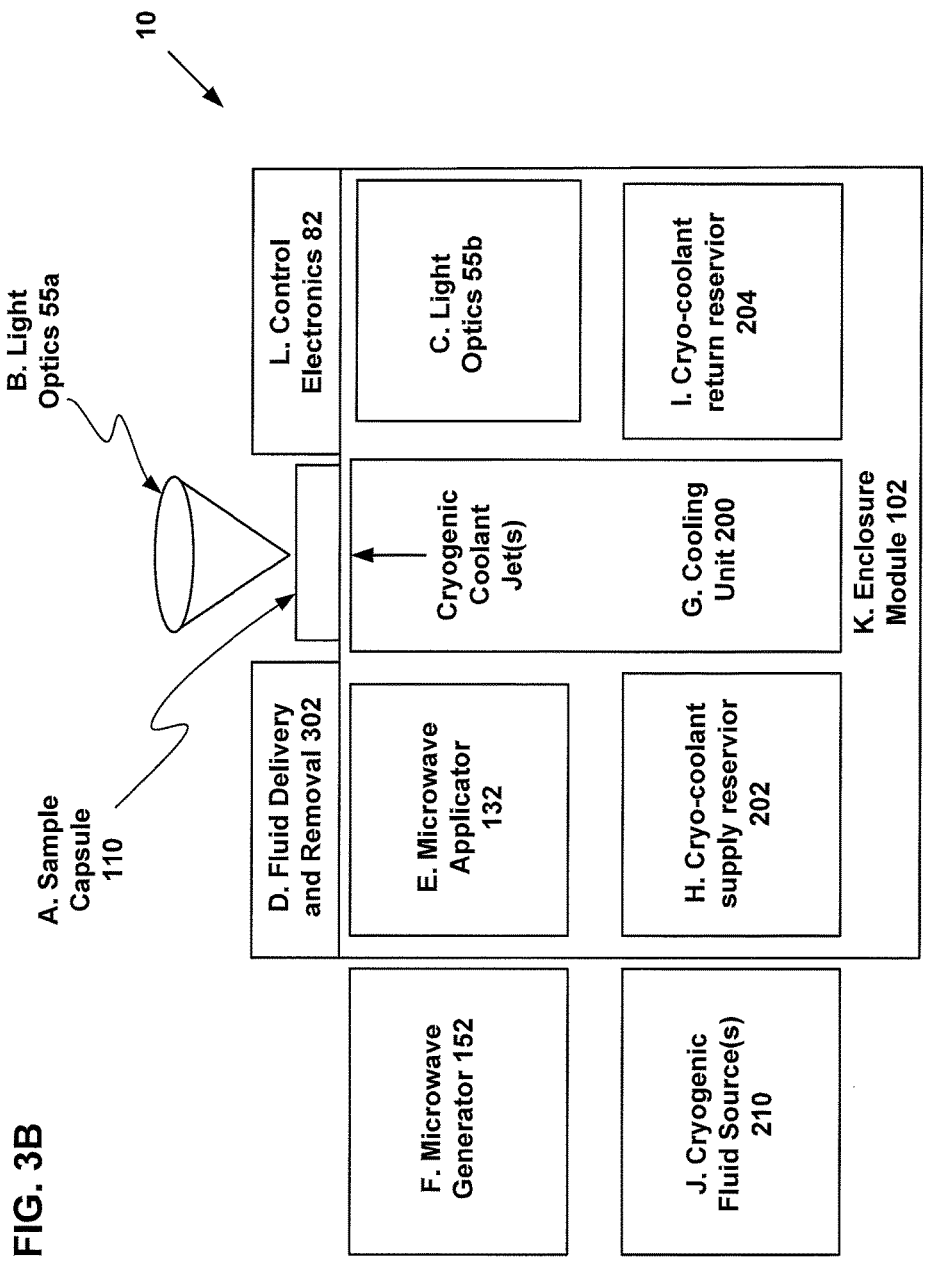
FIG. 3B is a schematic illustration showing portions of a sample vitrification system in accordance with another embodiment of the present disclosure.
Figure 4A:
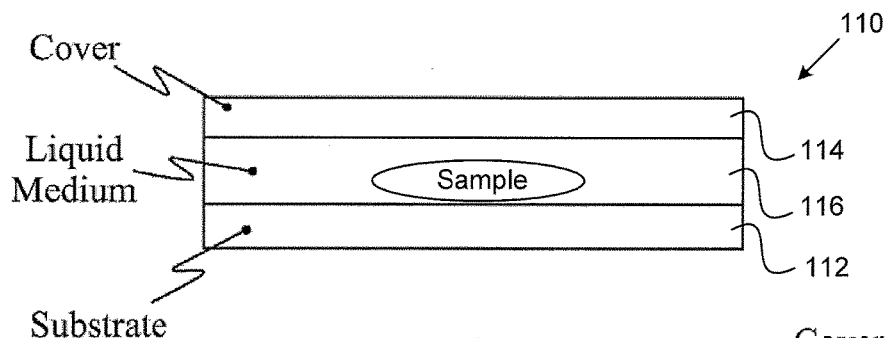
FIGS. 4A-4D are representative illustrations showing portions of sample chambers, receptacles, or capsules in accordance with particular embodiments of the present disclosure.
Figure 4B:
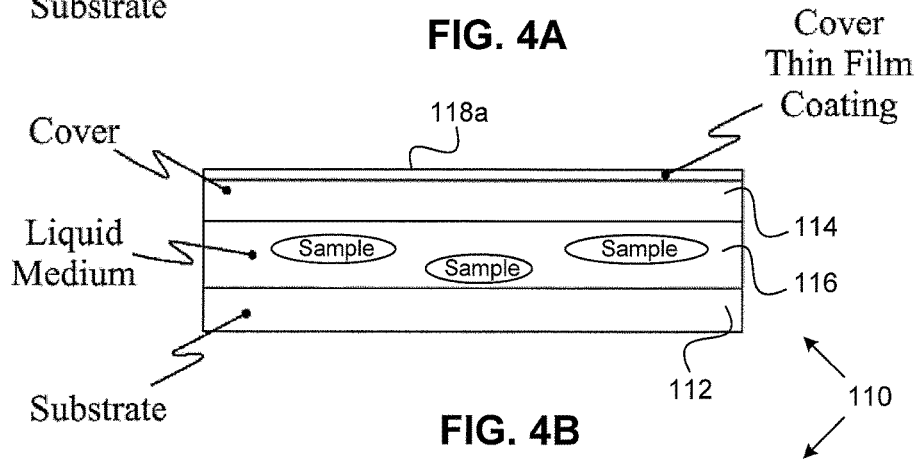
Figure 4C:
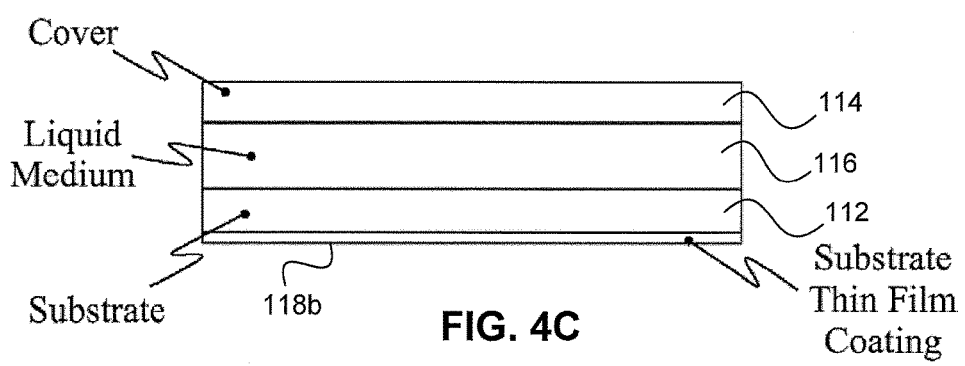
Figure 4D:
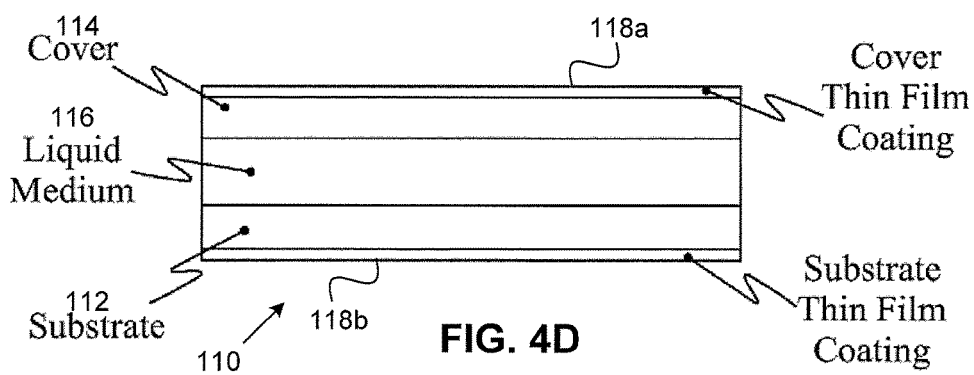

FIG. 3B is a schematic illustration showing portions of a sample vitrification system in accordance with another embodiment of the present disclosure. In an embodiment, the system 10 includes a sample capsule 110; first light optics 55a (e.g., configurable or configured for focusing on or within a sample carried by the capsule 110); second light optics 55b (e.g., configured for transmission microscopy); an intra-capsule fluid delivery and removal apparatus 302 (e.g., which can correspond to or form a portion of a capsule environment management/control unit 300 and an intra-capsule environment fluid source 310 shown in FIG. 3A); a microwave applicator 132 (e.g., which can correspond to or form a set of electromagnetic signal delivery elements 130 shown in FIG. 3A); a microwave generator 152 (e.g., which can correspond to or form a portion of an electromagnetic signal source 150 shown in FIG. 3A); a cooling unit 200 configured for directing one or more cryogenic coolant jets to the capsule 110; a corresponding cryocoolant supply reservoir 202, a cryocoolant return reservoir 204, and a cryogenic fluid source 210; an enclosure module or housing 102 in which various portions of the system 10 reside, for instance, as a self-contained or sealable/sealed subsystem module; and control electronics 82, which can be coupled to or form a portion of a control system 80 shown in FIG. 3A.

In some embodiments, a sample processing, preparation, or fixation system 10 includes multiple sample capsules 110. For instance, a system 10 can include a first through nth capsule 110 configured in a predetermined spatial arrangement (e.g., a rectangular array, or a circular/rotary configuration). Depending upon embodiment details, such a system 10 can include one or multiple cooling units 200. For instance, a set of cooling units 200 can be configured to direct or apply cryocooled fluid(s) to multiple capsules 110, e.g., to facilitate or enable sequenced or simultaneous sample vitrification processes involving multiple capsules 110. Furthermore, one or more cooling units 200 can be configured for selectable or programmable displacement relative to the capsules 110 (e.g., capsules 110 can be configured for rotary or turret-style displacement relative to one or more cooling units 200), such that cryocooled fluid(s) can be directed or applied to particular capsules 110 at particular times and/or in accordance with a desired or intended (e.g., programmably specified) sample vitrification sequence. In embodiments that include multiple capsules 110, individual capsules 110 can be sufficiently separated and/or thermally isolated (e.g., by way of insulative materials or the establishment of a partial vacuum between individual capsules 110) in a manner that ensures that distinct vitrification processes performed upon different capsules 110 can remain thermally or substantially thermally independent (e.g., such that a first vitrification process directed to a first sample carried by a first capsule 110 does not affect or significantly affect a second sample carried by a second capsule 110 or a second vitrification process directed to the second sample).

In any of the foregoing embodiments, one or more capsules 110 can be carried by, coupled to, or form a portion of a positioning apparatus or stage assembly, such as a manual, semi-automated, or automated stage configured for 2-axis or 3-axis positioning or displacement (e.g., x, y, z, and/or θ positioning), in a manner understood by one of ordinary skill in the relevant art.

Aspects of Representative Capsule Design, Sample Cryofixation, and Microwave Energy Application FIGS. 4A-4D are representative illustrations showing portions of sample chambers, receptacles, or capsules 110 in accordance with particular embodiments of the present disclosure. In general, a capsule 110 includes a first or lower surface or layer; a second or upper surface or layer 114; and an internal compartment 116 disposed between the first and second layers 112, 114. In the description hereafter, the first or lower layer 112 is referred to as a substrate or substrate layer; and the second or upper layer 114 is referred to as a cover.

The substrate 112 exhibits a high, very high, or extremely high thermal conductivity, and serves as a thermal energy transfer interface or medium between a sample carried within the chamber's internal compartment 116 and one or more cryogenically cooled substances or materials provided by a cooling unit 200. Depending upon embodiment details and/or the nature of a sample under consideration, one or more portions of the sample can be in direct contact with the substrate 112, and/or one or more portions of the sample can be carried or suspended in a liquid medium such as water within the compartment 116.

The substrate 112 is additionally at least substantially transmissive or transparent with respect to microwave and/or other electromagnetic energy wavelengths that can be directed into the capsule 110. Furthermore, in embodiments configured for transmission microscopy, the substrate 112 is at least substantially transmissive or transparent with respect to one or more imaging wavelength ranges under consideration. In multiple embodiments, the substrate 112 includes or is a layer of diamond or sapphire. In a representative implementation, the substrate 112 is a diamond disk having a diameter of approximately 8 mm.

The cover 114 forms one or more portions of an imaging interface or imaging interface layer that is at least substantially transparent or transmissive with respect to a set of imaging wavelength ranges under consideration, such as one or more of visible light wavelengths, infrared light wavelengths, and ultraviolet light wavelengths. In various embodiments, the cover 114 is transparent to optical microscopy illumination wavelengths, and includes or is a material such as glass, quartz, or plastic. In certain embodiments, the cover 114 can include or be a material that is significantly or substantially thermally insulating (e.g., a plastic or polymer based material), which can enhance a rate at which the substrate 112, and hence a sample within the compartment 116, can be cooled.

The compartment 116 forms a receptacle within which (a) at least one sample can be disposed; and (b) microwave and/or other electromagnetic energy or fields can be directed, applied, or delivered to the sample(s). The compartment 116 provides or establishes a gap, depth, or thickness between the substrate 112 and the cover 114, such that the sample can reside within the spatial (e.g., vertical) extent of the gap. Depending upon embodiment details and/or the nature of a sample under consideration, the gap can have a depth or thickness on the order of one micron, several microns, tens of microns, or hundreds of microns. In some embodiments, the capsule 110 is configured to provide an adjustable or selectable gap, depth, or thickness, while in other embodiments particular capsules 110 (e.g., which can be removably transferred or selectably inserted onto/into the apparatus 100) exhibit a predetermined gap, depth, or thickness.

Various embodiments in accordance with the present disclosure are configured for exposing a sample within the compartment 116 to microwave energy, signals, or radiation (e.g., which can be generated in accordance with particular, predetermined, selectable, or programmable microwave signal parameters). A wide variety of electromagnetic signal delivery element configurations, e.g., for directing microwave energy into portions of the capsule 110, can exist, as further detailed below. In general, particular portions of the system 10 such as the capsule 110 and/or a set of optical elements 55 can include one or more shielding interfaces or coatings to ensure or maximize the likelihood that microwave and/or other electromagnetic energy directed into the capsule's compartment 116 remains confined within an intended, predetermined, or limited spatial region.

For instance, as indicated in FIGS. 4A-4D, the capsule 110 can include a first shielding layer 118a carried by the capsule cover 114, and/or a second shielding layer 118b carried by the capsule substrate 112. In embodiments in which the capsule's cover 114 carries or includes a shielding layer 118a, the shielding layer 118a is at least substantially transparent to a set of imaging wavelength ranges under consideration, and at least substantially non-distorting with respect to imaging requirements. In embodiments in which the substrate 112 carries a shielding layer 118b and the system 10 is configured for transmission imaging, the shielding layer 118b is at least somewhat or substantially transmissive or transparent to imaging wavelength ranges under consideration. For instance, a shielding layer 118a,b can include a layer based upon or formed from an Indium Tin Oxide (ITO), graphene, and/or other material (e.g., a metamaterial), which is transparent to optical illumination wavelengths and optically non-distorting, and which is electrically conductive and hence is suitable as a microwave field barrier or shield. Additionally, a substrate-side shielding layer 118b can be structured or engineered in a manner that avoids substantially impacting the substrate's thermal conductivity (e.g., a substrate-side shielding layer 118b should exhibit a high, very high, or extremely high thermal conductivity, and/or minimally impact the substrate's transfer of thermal energy from the sample to a cryogenically cooled substance or material provided by the cooling unit 200, such as by way of a thin or very thin ITO-based shielding layer 118b).

Depending upon embodiment details, a shielding layer 118a-b can be essentially or entirely continuous across one or more portions of a planar surface of a substrate 112 or a cover 114, or a shielding layer 118a-b can be patterned. For instance, in an embodiment, a substrate 112 can carry a shielding layer 118b (e.g., a thin layer or coating of ITO, gold, or graphene) that is patterned in a manner that provides apertures having dimensions that are sub-wavelength with respect to particular wavelengths of microwave energy under consideration. In such an embodiment, microwave energy originating from a source, device, or circuit element external to the capsule 110 and incident upon the capsule 110 at the substrate-side will be prevented from establishing a propagating mode within the capsule 110. However, an evanescent microwave field will couple into or enter the capsule 110 by way of the apertures. This evanescent microwave field can extend to or within one or more portions of a sample and/or surrounding fluid, and hence can affect or control sample vitrification by way of disrupting $H_2O$ pentamer formation during a vitrification process that involves exposing the substrate 112 to a cryogenically cooled substance or material, as further detailed below.

In embodiments in which one or more optical elements 55 such as a microscope objective lens are exposable or exposed to microwave fields, such optical elements 55 can be associated with or include shielding layers or structures. For instance, an objective lens backplane can be associated with or include a conductive plate structure having an appropriate type of microwave field shielding layer or coating (e.g., an ITO, graphene, and/or other material layer).

A number of temperature sensitive or sensing elements or devices can be configured for sensing, monitoring, or measuring temperatures or temperature changes corresponding to the substrate 112 and/or other portions of the chamber 110. In some embodiments a substrate 112 can carry, include, or be coupled to a set of thermocouple or thermoresistive elements, which can be disposed in accordance with a desired or predetermined pattern such as an array. Certain embodiments can include optical devices (e.g., infrared light detectors) configured for sensing or measuring temperatures or temperature changes.

Figure 5A:
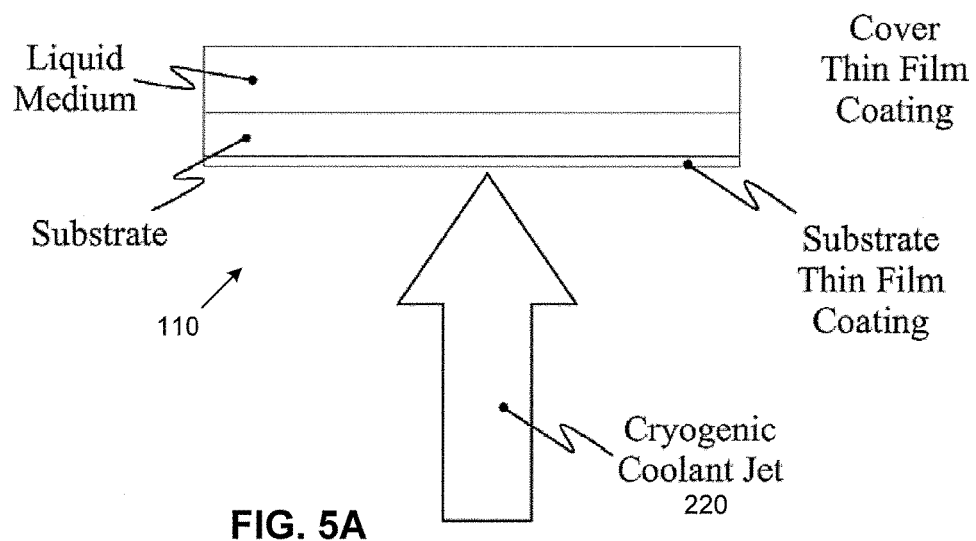
FIGS. 5A and 5B illustrate aspects of a cooling unit that can direct at least one cryogenic coolant jet to a very high or extremely high thermal conductivity substrate in accordance with embodiments of the present disclosure.
Figure 5B:
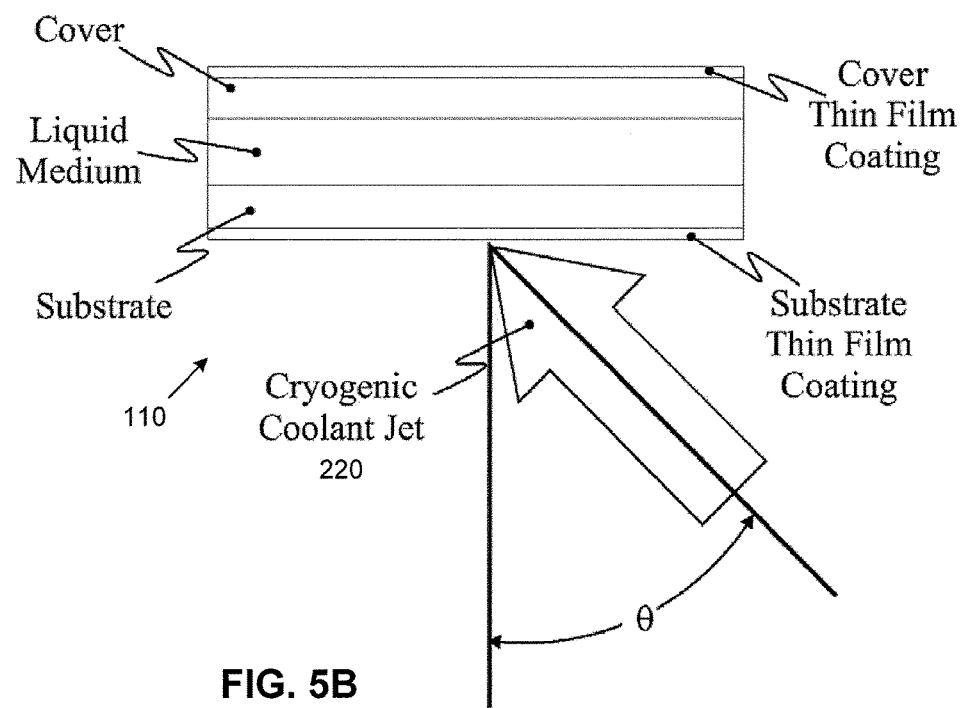
Figure 6A:
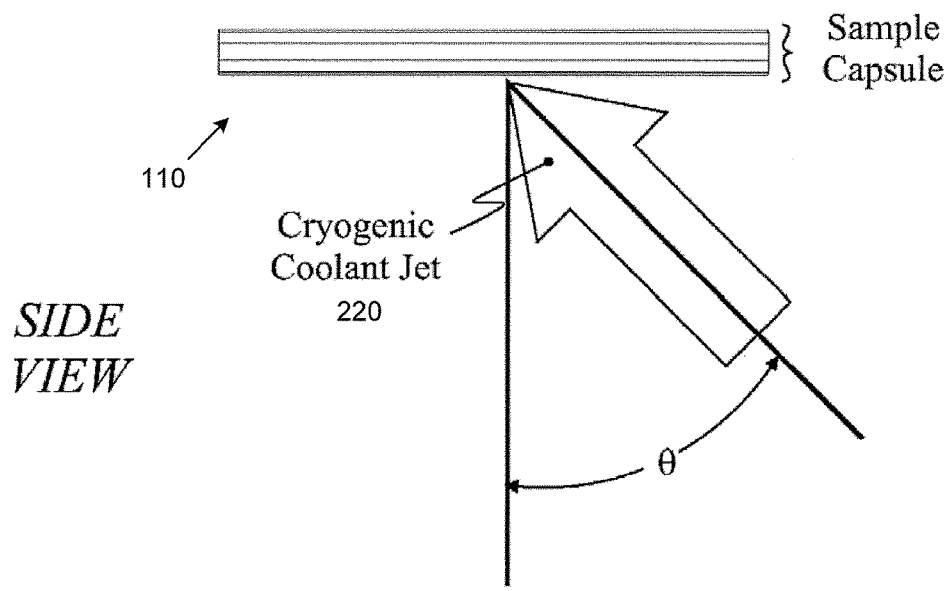
FIGS. 6A-6H are schematic illustrations of a cryocoolant jet that is incident upon very high or extremely high thermal conductivity substrates having one or more patterned substrate regions in accordance with embodiments of the present disclosure.
Figure 6B:
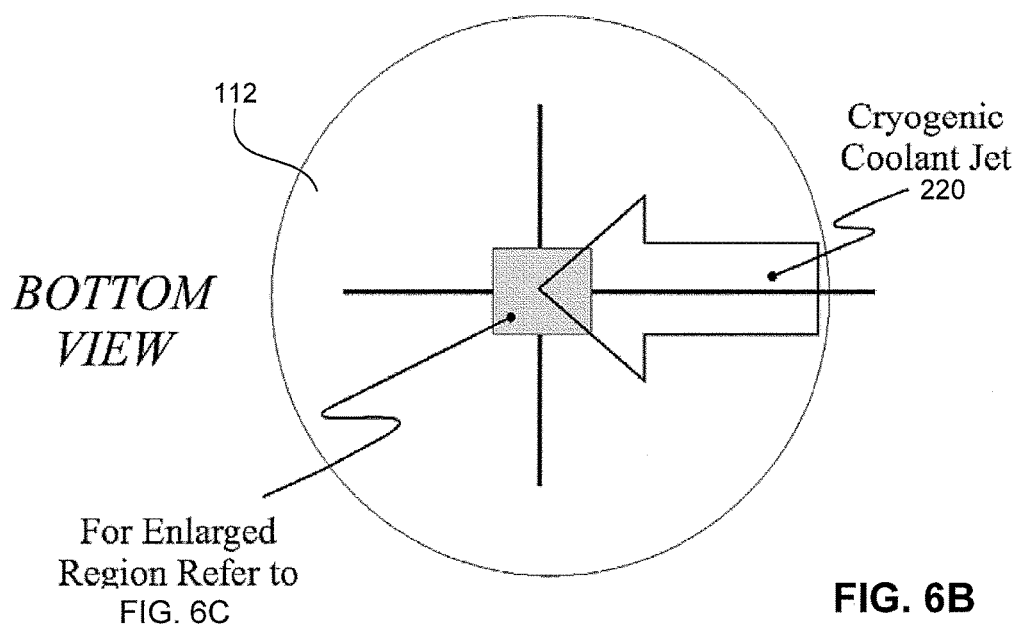
Figure 6C:
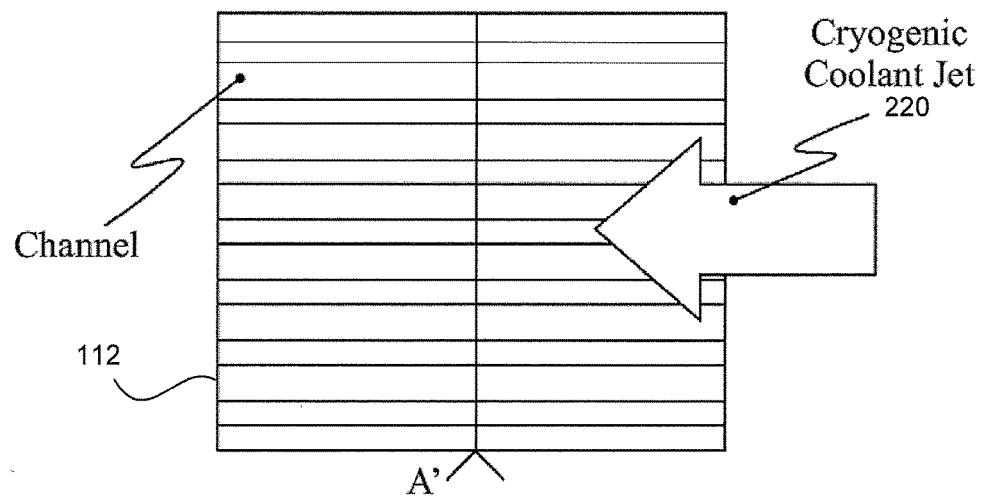
Figure 6D:
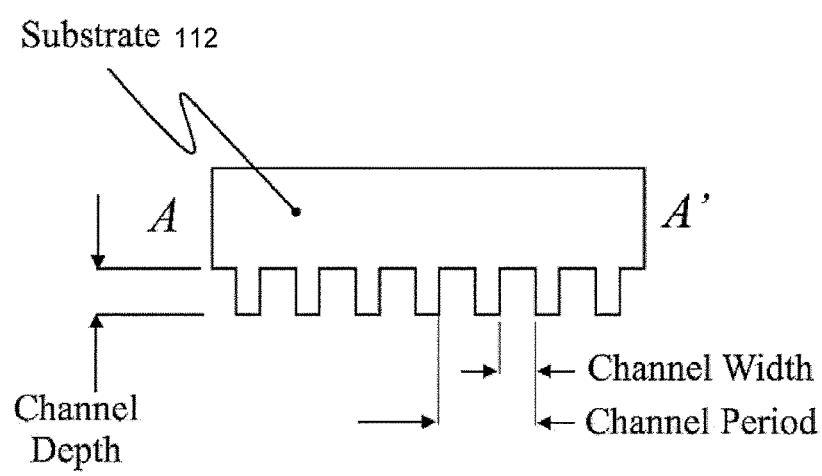
Figure 6E:
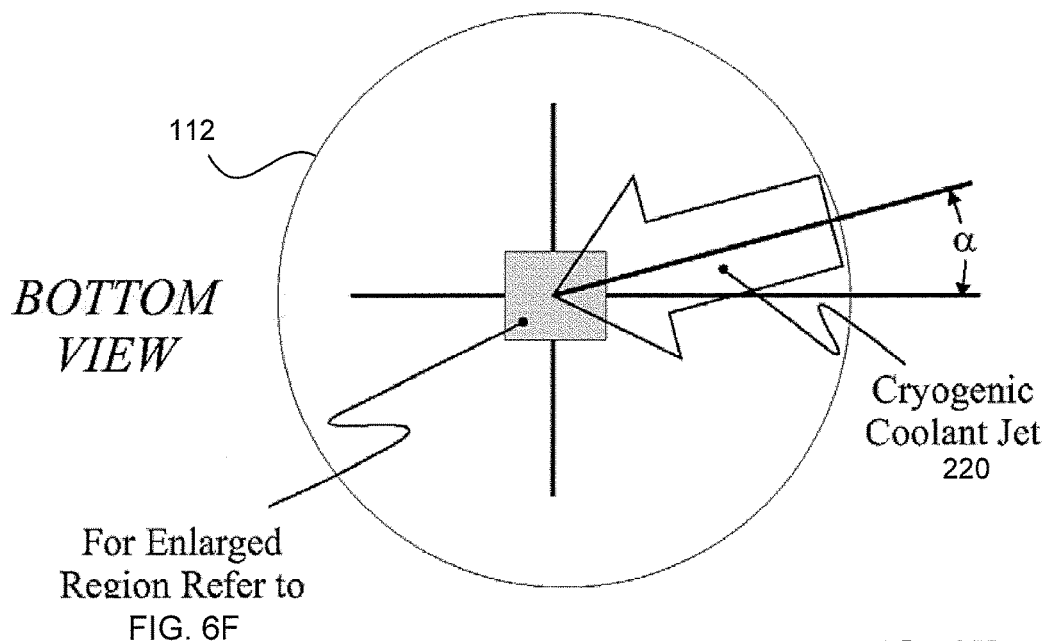
Figure 6F:
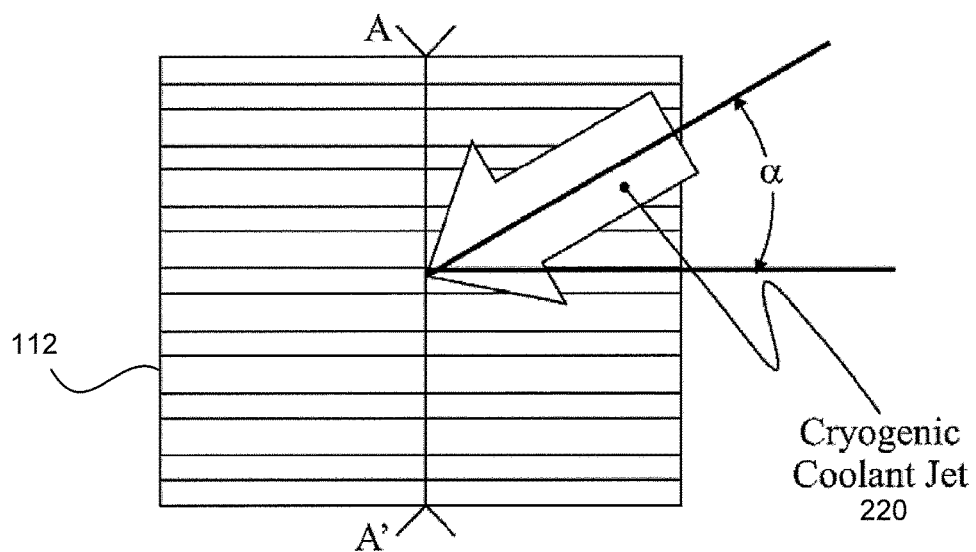
Figure 6G:
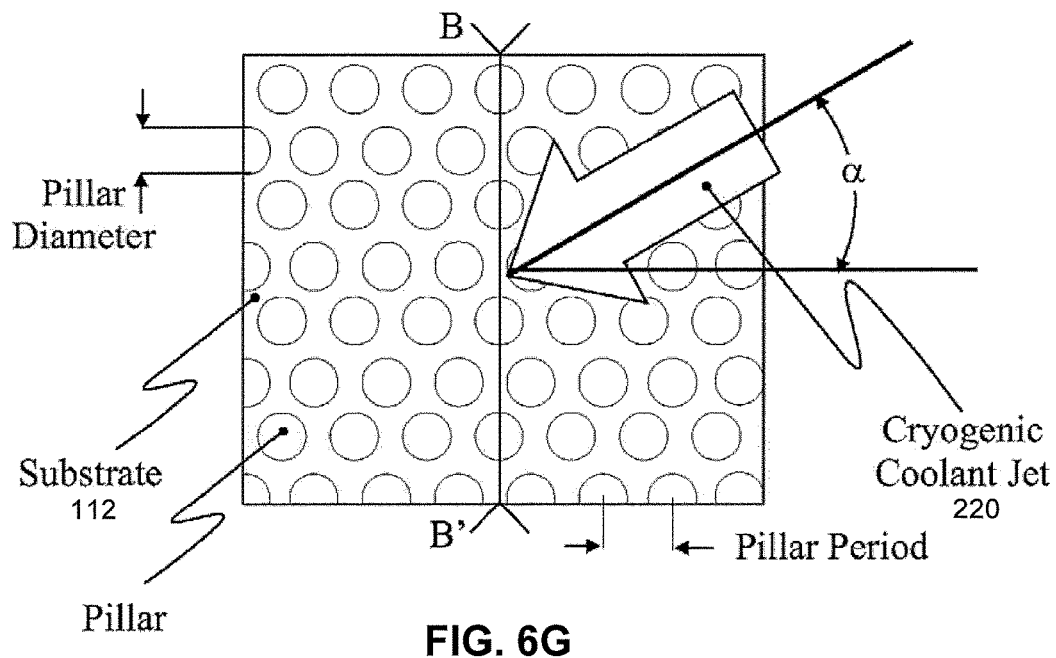
Figure 6H:
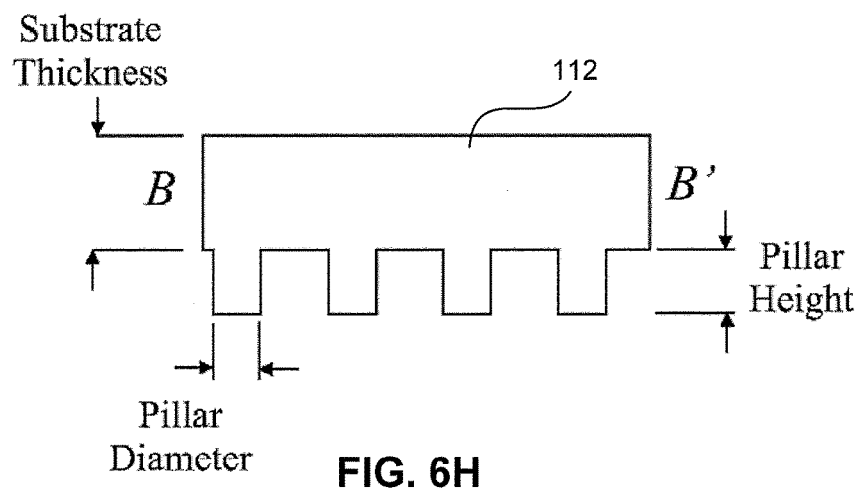

Thermal coupling, energy transfer, or contact between the capsule's substrate 112 and one or more cryogenically cooled substances and/or materials provided by a cooling unit 200 can be provided or established in multiple manners. In various embodiments, the cooling unit 200 is configured for directing at least one stream of cryogenically cooled liquid such as liquid nitrogen, liquid ethane, liquid propane, or another cryogenic liquid to an outer or exterior surface of the substrate 112 which is exposable or exposed to the stream(s) in order to facilitate or enable extremely rapid thermal energy transfer between a sample within the capsule 110 and the cryogenically cooled liquid(s). As indicated in FIGS. 5A and 5B, the cooling unit 200 can direct (e.g., by way of a set of cryocoolant applicator elements, conduits, or nozzles) at least one cryogenic coolant jet 220a,b to the substrate 112 in one or more manners, e.g., in a direction normal or substantially normal to a substrate plane that is parallel to or which forms an exterior planar surface of the capsule 110, and/or at a given non-normal angle θ with respect to such a substrate plane.

Various embodiments in accordance with the present disclosure can direct or apply cryogenically cooled liquid(s) to the substrate-side of the capsule 110 in a manner that reduces or minimizes the effect(s) of a stagnation point that can be associated with an inner or central region (e.g., centroid) of a cryocoolant stream or jet. A stagnation point arises as a result of a low or very low local cryocoolant fluid velocity at a substrate impact interface at which cryocoolant velocity approaches or effectively equals zero. Consequently, a stagnation point can give rise to nonuniform substrate cooling. In some embodiments, a cryocoolant jet 220b can be directed toward the substrate 112 at one or more non-normal angles, e.g., an angle of θ degrees, or rapidly cycled, displaced, or swept within an angular range, in order to reduce or minimize stagnation points, where an angle θ or an angular range can be defined with respect to a normal direction or axis relative to the substrate plane. Additionally or alternatively, multiple time sequenced or time multiplexed and/or pressure sequenced or pressure multiplexed cryocoolant jets 220a,b can be directed toward the substrate 112 (e.g., by way of multiple cryocoolant jet nozzles) to reduce or minimize stagnation points.

In some embodiments, the substrate 112 can include one or more shaped, contoured, or patterned portions or regions that can facilitate or effectuate an enhanced thermal energy transfer efficacy or rate; reduced thermal stagnation effects; and/or the establishment or maintenance of intended cryocoolant flow patterns (e.g., in view of thermal energy transfer efficacy associated with turbulent and/or laminar flow, for instance, microstructures intended to facilitate disruption of laminar flow). For instance, FIGS. 6A-6H are schematic illustrations of a cryocoolant jet 220 that is incident upon substrates 112 having one or more patterned substrate regions. A substrate 112 can include or be fabricated to carry or include micro-scale structural features such as channels, grooves, and/or pillars that result in portions of the substrate 112 having reduced thickness. Such micro-scale structural features can be spatially or geometrically organized or distributed in a uniform or non-uniform manner that facilitates or enables enhanced efficacy thermal energy transfer while substantially maintaining or retaining adequate substrate structural integrity. A cryogenic coolant jet 220 can be incident upon an external, exterior, or outer surface of the substrate 112 along a direction or at an angle α defined relative to particular structural features. Depending upon embodiment details, a direction or angle of incidence corresponding to a given cryocoolant jet 220 can be aligned or substantially aligned relative to particular structural features such as channels, or at least partially misaligned relative to particular structural features such as pillars. Depending upon embodiment details, micro-structural features can have a vertical extent or depth of less than one to one, several, tens, or several tens of microns, and a lateral separation or periodicity of less than one to one, several, tens, or several tens of microns.

In various embodiments, the cooling system 200 provides a self-contained, closable, sealable, closed, or sealed system or subsystem in which one or more cryocoolant liquids can be directed or applied to the substrate 112 and internally recirculated, reused, or reapplied to the substrate 112. Such embodiments can include a cryocoolant supply reservoir 202 and a cryocoolant return reservoir 204 as indicated in FIG. 5B, which are coupled to at least one pressurized (e.g., high pressure) cryogenic fluid stream, jet, and/or spray delivery apparatus, device, applicator, or nozzle. A cooling system 200 in accordance with an embodiment of the present disclosure can include one or more devices, components, or elements described in U.S. Pat. Nos. 4,336,691; 5,044,165; and/or 7,637,187.

In general, a sample should be maintained at a desired, target, or predetermined initial or reference temperature or within a desired, target, or predetermined initial or reference temperature range prior to the application of a cryocooled substance or material to the substrate 112. Sample pre-cooling, that is, cooling of the sample(s) away from or below a target initial or reference temperature or temperature range prior to a time at which thermal energy transfer of contact between a cryocooled substance or material with the substrate 112 is intended to occur, can augment nucleation sites and corresponding ice crystal growth. Hence, sample pre-cooling should generally be avoided. Furthermore, the application of a cryocooled substance or material to the substrate 112 should occur in a manner that transitions the substrate 112, and hence the sample carried by the capsule's chamber 116, from the initial or reference sample temperature or temperature range to a sample vitrification temperature as rapidly as possible.

In order to minimize the likelihood or extent of sample pre-cooling, or at least substantially avoid sample pre-cooling, a system 10 or apparatus 100 in accordance with particular embodiments of the present disclosure can include one or more types of chamber or sample temperature establishment, regulation, or maintenance mechanisms or elements. For instance, the substrate 112 and/or the cover 114 can include conductive portions or elements (e.g., conductive lines or wires, or a conductive shielding layer 118a,b itself) that can be coupled to an electrical current source, and which can provide or deliver a controllable or monitorable amount of thermal energy (e.g., small amounts of heat, such as by way of ohmic or resistive heating) to portions of the capsule 110. The system 10 or apparatus 100 can additionally or alternatively include a number of optical heating elements configured for applying or delivering thermal energy to portions of the capsule 110, such as infrared LEDs or optical fibers. Moreover, portions of a system 10 or apparatus 100 configured for carrying microwave signals can deliver or apply microwave energy to the sample(s) and/or the capsule's compartment 116 at a wavelength, wavelength range, and/or intensity that results in sample and/or compartment 116 temperature establishment, maintenance, or selectable/selective heating. Some embodiments can additionally establish, provide, or inject a neutral gas (e.g., a dry gas) that facilitates thermal insulation, e.g., a heavier dry gas such as Argon, into a spatial region of the cooling unit 200 between a cryojet nozzle terminus or tip and the capsule 110.

In some embodiments, the cooling unit 200 includes at least one breakable or pierceable membrane (e.g., a polymer membrane) disposed between the cryocoolant jet(s) and an external, exterior, or outer substrate surface. More particularly, each such membrane can serve as a thermal energy transfer regulation or barrier element between the cryocoolant jet(s) and the substrate 112. The membrane(s) can be broken or pierced in response to an incident cryocoolant jet pressure or force that exceeds a predetermined or target level or value (e.g., one or more grams per square centimeter), which can occur at an intended vitrification initiation time or in response to a trigger event. Furthermore, the cooling unit 200 can be configured to establish or maintain a partial vacuum within a spatial region between a breakable membrane and the capsule 110, which provides or enhances a thermal barrier between a cryojet nozzle tip and the sample(s). In other embodiments, the cooling unit 200 can include an ultra fast mechanical shutter mechanism configured to selectively isolate a set of cryocoolant jets from the substrate 112 before an intended vitrification initiation time or the occurrence of a trigger event.

A likelihood or extent of sample pre-cooling can also be reduced or minimized by way of a cryocoolant jet displacement mechanism (e.g., a solenoid based or magnetic displacement mechanism) that is configured for keeping the cryocoolant jet(s) at a minimum intended distance away from the substrate 112 prior to an intended vitrification initiation time or the occurrence of a trigger event, and further configured for rapid displacement (e.g., relative or parallel to or along a direction or axis normal to a planar substrate 112) to a position proximate or adjacent to the substrate 112.

Figure 7A:
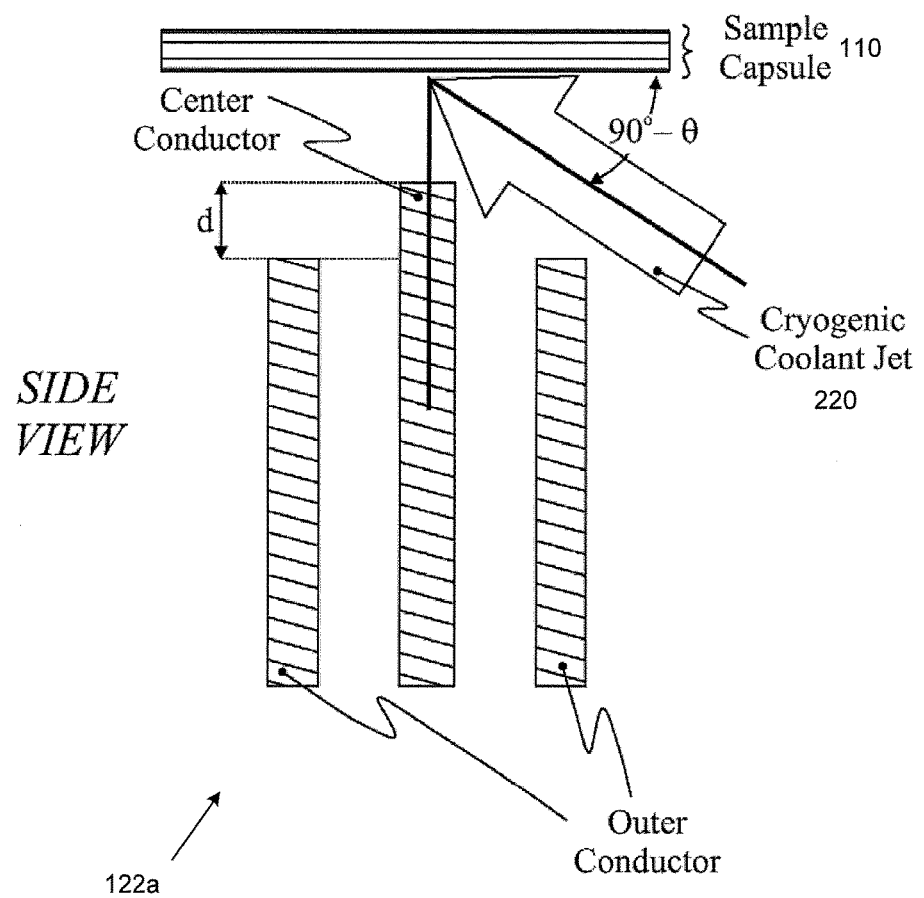
FIG. 7A is a schematic illustration of a microwave probe in accordance with an embodiment of the present disclosure.

As indicated above, depending upon embodiment details, microwave energy can be directed, delivered, or applied to portions of the capsule 110 and/or one or more samples therein in a variety of manners. In some embodiments, a set of electrically conductive elements or lines configured for carrying microwave signals can be disposable or disposed within the cooling unit 200, below and substantially normal to the substrate 112, such that the set of electrically conductive elements are configured for providing, delivering or applying microwave energy to particular portions of the capsule 110. In some embodiments, such a microwave field application device can correspond to or be analogous to a microwave drill, in a manner understood by one of ordinary skill in the relevant art. FIG. 7A is a schematic illustration of a microwave probe 122 in accordance with an embodiment of the present disclosure, which includes a center conductor and a set of outer conductors. At least one microwave probe 122 can be positionable or positioned such that microwave energy is deliverable or delivered to one or more target regions within the capsule 110 as a result of a microwave field or field distribution provided by the center and outer conductors. A vertical offset between the center conductor and the outer conductor(s) and/or a horizontal or lateral offset between the center conductor and the outer conductor(s) can be selected relative to microwave wavelengths under consideration, such that a terminal portion or end of the microwave probe 122 can provide or couple near-field or evanescent wave energy to portions of the cavity 110 (e.g., by way of sub-wavelength geometry or a near-field microwave conductor separation, gap, aperture, opening, or hole corresponding to a terminal portion or end of the microwave probe 122). For instance, in some embodiments, the microwave probe 122a is configured to provide near-field or evanescent wave coupling of microwave energy into a sample that is carried at or within an expected portion of the compartment 116. Thus, during a sample vitrification process, the center conductor can be positioned at a normal or vertical gap or distance relative to the underside or exterior surface of the substrate 112 such that evanescent wave coupling with the compartment 116 and/or sample can occur. As indicated in FIG. 7A, a cryogenic coolant jet 220 can be directed toward or to the substrate 112 at a non-normal angle of incidence θ, such that cryocooled liquid flows within the gap between the center conductor and the substrate 112.

In some embodiments, a microwave energy application or delivery device can be coupled to or associated, combined, or integrated with portions of a cryocoolant jet apparatus to form a microwave field-cryocoolant applicator that can (a) generate microwave fields suitable for disrupting $H_2O$ pentamer formation during a vitrification process; as well as (b) carry or output one or more cryocooled liquid streams or jets.

Figure 7B:
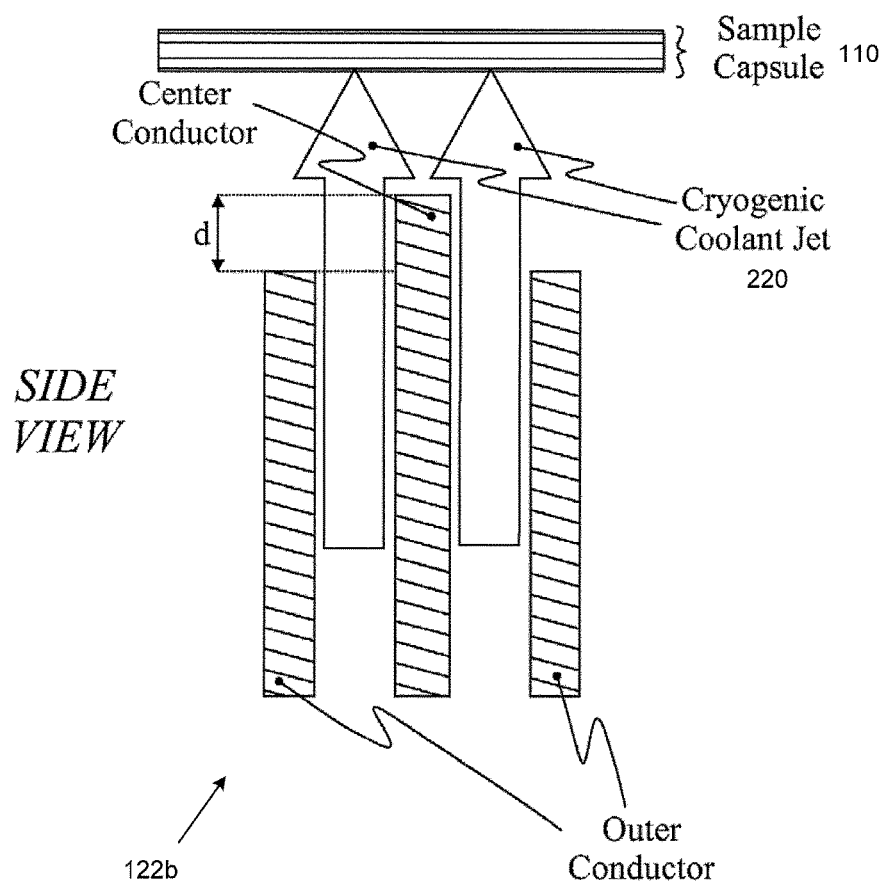
FIGS. 7B and 7C are schematic illustrations of a microwave probe/cryocoolant applicator in accordance with embodiments of the present disclosure.
Figure 7C:
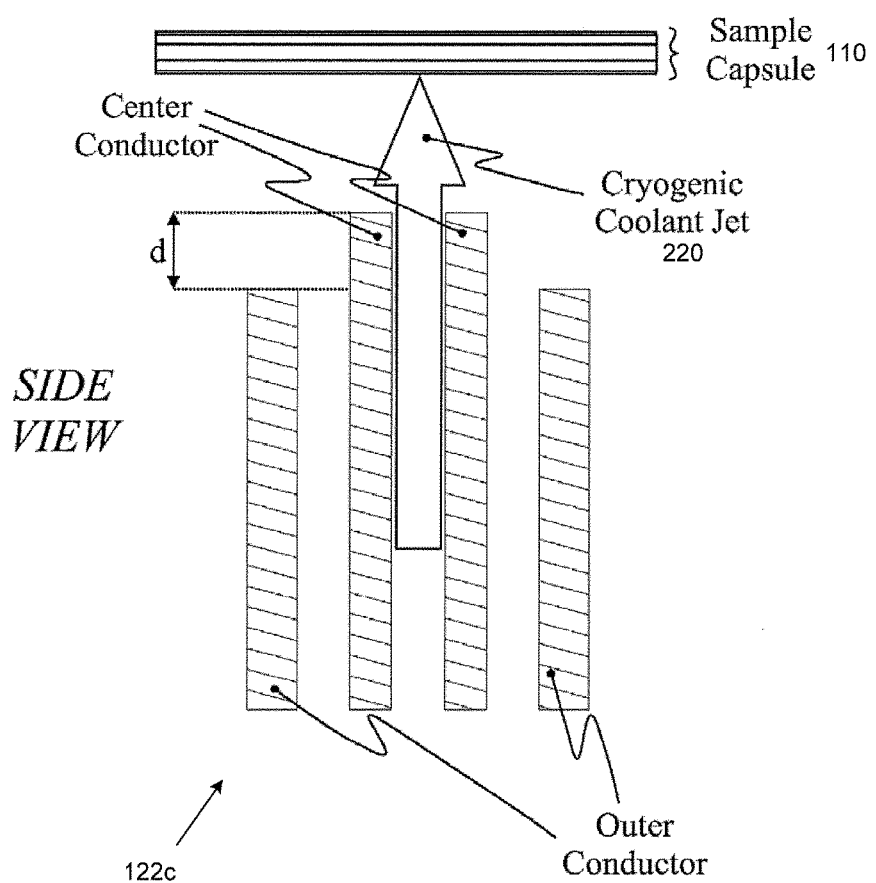

For instance, FIG. 7B is a schematic illustration of a microwave probe/cryocoolant applicator 122b in accordance with an embodiment of the present disclosure, which is configured for providing, supplying, or establishing a cryocoolant jet by way of cryocoolant liquid flow between a center conductor and an outer conductor, such that the cryocoolant liquid can be output, ejected, or shot from a terminal portion or end of the field microwave probe/cryocoolant applicator 122b and directed toward or to the substrate 112 (e.g., in a direction normal or substantially normal to a plane of the substrate 112). The terminal portion or end of the microwave probe/cryocoolant applicator 122b can thus form a nozzle structure for delivering cryocooled liquid to the substrate 112. FIG. 7C is a schematic illustration of a microwave probe/cryocoolant applicator 122c in accordance with another embodiment of the present disclosure, which is configured to provide, supply, or establish a cryocoolant jet by way of cryocoolant liquid flow within a channel or passage defined by a center conductor. In other embodiments, aspects of FIGS. 7B and 7C can be combined. In some embodiments, a microwave probe or a microwave probe/cryocoolant applicator 122 can be configured to carry, propagate, or transmit light within a gap between a center and an outer conductor, or within a center conductor passage, to facilitate transmission microscopy.

Microwave fields can also be delivered to a sample within a capsule 110 in additional or other manners. For instance, some embodiments in accordance with the present disclosure generate or deliver microwave fields by way of stripline or co-planar waveguide elements, which enable microwave energy transport along patterned conductors such that microwave fields can be controlled to initiate and terminate relative to particular portions of conductive lines or branches. Embodiments that include stripline or co-planar waveguide elements can be compact or highly compact, and can facilitate tight microwave field confinement and/or minimal microwave field leakage.

FIGS. 8A-8D are schematic illustrations of a microstrip capsule structure or assembly 110 in accordance with an embodiment of the present disclosure. In an embodiment, the microstrip capsule assembly 110 includes a dielectric support member or substrate 120 that includes at least one sample or specimen compartment 116, and which carries or includes a set of microwave signal elements coupled to a microwave signal source or generator 152 (e.g., a microwave amplifier). The set of microwave signal elements is configured for providing, delivering, applying, or coupling microwave fields to internal portions of the compartment(s) 116, as further detailed below.

Depending upon embodiment details, the substrate 120 can be fabricated as one or more layers using one or more materials. In some embodiments, the substrate 120 can include or be portions of a printed circuit board (e.g., provided by Rogers Corporation Advanced Circuit Materials (Rogers Corporation, Connecticut, USA, www.rogerscorp.com). One or more portions of the substrate 120 can additionally or alternatively be coupled to, carry, include, or be a high, very high, or extremely high thermal conductivity material, such as diamond or sapphire.

The set of microwave signal elements includes a number of microwave transmission lines 122 and a ground signal path, element, or plate 124. In several embodiments, the set of microwave signal elements further includes a number of impedance matching or tuning structures or elements 126, such as a set of integrated stub tuner elements (e.g., multi-stub tuners), such that the set of microwave signal elements can be coupled to and impedance matched with a set of conventional or standard impedance (e.g., 50 Ohm) signal lines. The matching structures or elements 126 can include non-adjustable and/or adjustable (e.g., microelectromechanical (MEMS) based and/or microfluidic liquid based) impedance matching elements.

In general, the set of microwave signal elements includes at least one microwave transmission line 122 configured for carrying microwave frequency electrical signals to, across, over, under, into, and/or through portions of the compartment(s) 116. The microwave transmission line(s) 122 can exhibit various spatial or geometric configurations, such as a straight or substantially straight stripline pattern, or a meander pattern. The microwave transmission lines 122 and the ground plate 124 can be fabricated using one or more conductive or highly conductive materials (e.g., copper or gold). An individual of ordinary skill in the relevant art will understand that the set of microwave signal elements can be directly or substantially directly fabricated or integrated upon and/or within portions of the substrate 120, for instance, by way of microfabrication techniques (e.g., corresponding to semiconductor device or integrated circuit fabrication processes).

The compartment 116 is configured for carrying, retaining, or surrounding a sample (e.g., a liquid within which a biological specimen is disposed), and can be fabricated or integrated upon or within portions of the substrate 120. For instance, the compartment 116 can be a machined, micro-machined, milled, etched, and/or molded opening or recess within the substrate 120. Additionally or alternatively, the compartment 116 can be an insertable structure (e.g., an insert configured for carrying or at least partially retaining a liquid, and a biological specimen disposed therein). In some embodiments, a microstrip capsule assembly 110 includes a number of microfluidic channels 117 configured for fluid communication (e.g., gas and/or liquid flow) with the compartment 116, which can be fabricated or integrated upon or within the substrate 120 in a manner identical, substantially identical, or analogous to that for the compartment 116 as understood by one of ordinary skill in the relevant art. Such embodiments can include or be coupled to additional or other microfluidic structures or elements (e.g., fluid flow control elements), in a manner also understood by one of ordinary skill in the relevant art.

The microstrip capsule assembly 110 can further include a cover structure, member, or element 114 configured for overlaying or covering the compartment 116. The cover 114 can be substantially transmissive or transparent with respect to one or more imaging wavelength ranges under consideration (e.g., optical imaging wavelengths) in order to facilitate or enable imaging, focusing, or image capture therethrough. The cover 114 can additionally carry or include one or more electrically conductive materials (e.g., a layer of ITO) and/or structures (e.g., transmission line or electrode elements) configured for providing electrical continuity between or across distinct or separate portions of a given microwave transmission line 122. Electrically conductive materials carried by the cover 114 can be substantially transmissive or transparent relative to imaging wavelength ranges under consideration, or electrically conductive materials can be patterned or routed in a manner that minimizes or avoids obstructing or adversely affecting imaging, focusing, or image capture (e.g., which substantially or entirely avoids obstructing and/or distorting optical signals propagating along an optical/imaging axis corresponding to an optical microscopy system). Depending upon embodiment details, electrical continuity between a microwave transmission line 122 and electrically conductive portions of the cover 114 can be provided by way of direct or substantially direct electrical coupling or contact, or by way of a gap feed, in a manner understood by one of ordinary skill in the relevant art.

In addition or as an alternative to the foregoing, in certain embodiments, a cooling unit 200 can include a selectively displaceable (e.g., vertically displaceable) cryogenically cooled plate, stage, or disc configured for establishing contact with the substrate 112. For instance, the cooling unit 200 can include a cryogenically cooled plate that can be pre-cooled to an intended or desired cryogenic temperature (e.g., by way of exposure to or at least partial immersion in liquid nitrogen or another cryofluid), and which can be controllably and rapidly displaced to establish contact with an exterior or outer surface of the substrate 112 to initiate sample vitrification. The cryocooled plate and the substrate 112 can include very smooth/uniformly planar surfaces (e.g., machined/polished parallel surfaces) configured for establishing intimate contact with each other. The cryocooled plate can include or be carried by a positional accommodation mechanism, such as a set of springs or an elastomeric material, to facilitate auto-adaptive positional adjustment (e.g., angular tilt adjustment) in the event that surfaces intended for maximum intimate planar contact exhibit a certain degree of non-planarity. Additionally or alternatively, the cryocooled plate can carry or include one or more material layers or coatings (e.g., an ITO layer) on an exterior surface intended for contact with the substrate 112 that can facilitate enhanced intimacy contact with the substrate 112 and/or enhanced efficacy thermal energy transfer.

A cooling unit 200 can include a port configured for automatically or semi-automatically loading (e.g., on a user-selectable basis) new or unused cryocooled plates into the cooling unit 200 or unloading used or insufficiently planar cryocooled plates from the cooling unit 200. Furthermore, a cooling unit 200 can be configured for internally carrying multiple cryocooled plates therein, such that a new or unused cryocooled plate can be selected and/or loaded into an appropriate spatial position relative to the substrate 112 prior to a sample vitrification process, and a cryocooled plate that has been used more than a selectable or predetermined number of times or which exhibits insufficient planarity or surface defects can be automatically or semi-automatically displaced or offloaded to a different spatial position following a sample vitrification process. In certain embodiments, a cryocooled plate and the substrate 112 can carry one or more alignment members (e.g., at outer portions) configured for mating engagement with each other.

In an embodiment involving a cryocooled plate, a microwave signal source can be coupled to the cryocooled plate such that microwave signals can be carried by or applied to the cryocooled plate itself. Hence, the cryocooled plate can serve as a microwave excitation source configured for exposing the sample(s) within the chamber 110 to microwave fields in order to disrupt or prevent $H_2O$ pentamer formation during a vitrification process.

In various embodiments, a microwave signal source or generator 152 can include or be a microwave amplifier such as a solid state microwave amplifier configurable or configured for outputting microwave signals having a frequency of between approximately 2 GHz-18 GHz (e.g., about 2.4-2.45 Ghz, 5.8 GHz, or 10 GHz or higher). Some embodiments include or utilize WiFi or analgous types of signal generators or components configured to provide up to, for instance, 10 W of power. Certain embodiments can include or utilize a Voltage Controlled Oscillator (VCO) configured for outputting a signal that is modulated by a PIN switch, where the modulated signal can be further amplified. Other embodiments can include or use a magnetron (e.g., a pulsed magnetron).

Microwave energy, signals, fields can be provided, delivered, applied, and/or coupled (e.g., by way of near field or evanescent wave coupling) to portions of a chamber in various manners, such as by way of a microwave probe or applicator; a set of patterned or integrated micro-scale transmission lines; resonant coupling; and/or a traveling wave apparatus or device. In general, microwave energy is providable or provided to a sample at a power density that is sufficient to affect, modulate, or prevent ice crystal formation or nucleation processes, but which avoids adversely affecting the sample or the sample vitrification process. In various embodiments, microwave energy, signals, or fields is provided in one or more pulsed manners to facilitate or effectuate a high or very high instantaneous microwave pulse power density that can disrupt or prevent $H_2O$ pentamer formation, yet which itself avoids or substantially avoids sample heating. More particularly, in multiple embodiments, microwave pulses are provided in a manner such that pulses or pulse sequences are timed or synchronized relative to ice crystal growth dynamics in a manner that corresponds to expected, simulated, or measured ice crystal nucleation/formation processes, for instance, ice crystal nucleation that occurs within a nucleation time or interval of approximately 300 microseconds (e.g., in which case microwave pulses are applied at time intervals less than or equal to approximately 300 microseconds), and substantially complete solidification within approximately 30 microseconds.

Figure 8A:
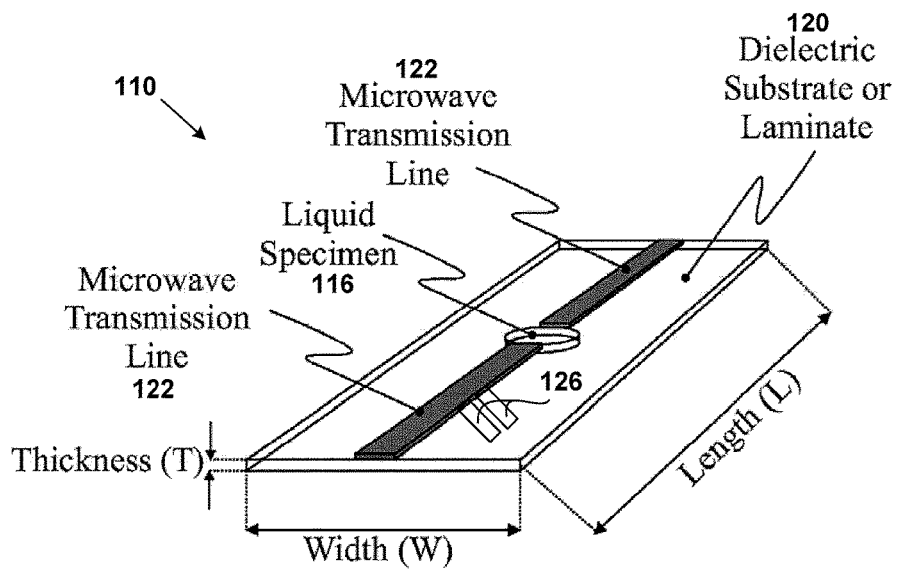
FIGS. 8A-8D are schematic illustrations of a microstrip capsule structure or assembly in accordance with an embodiment of the present disclosure.
Figure 8B:
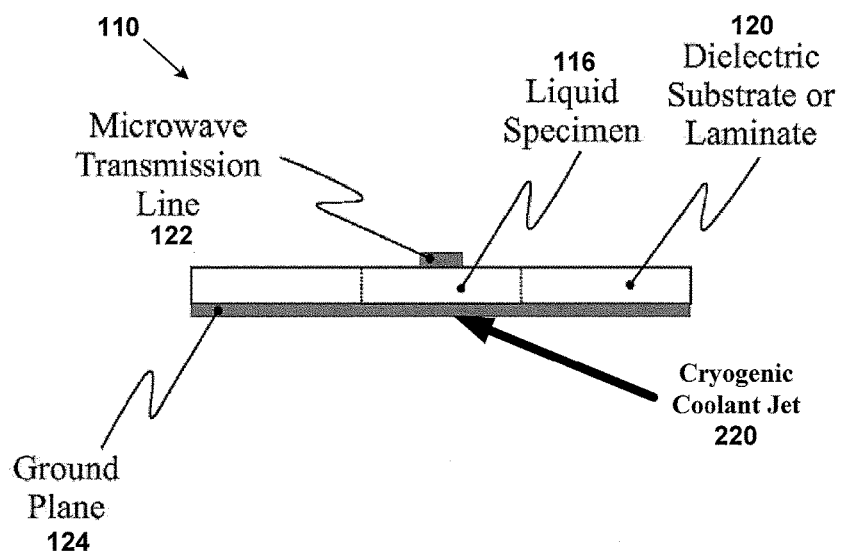
Figure 8C:
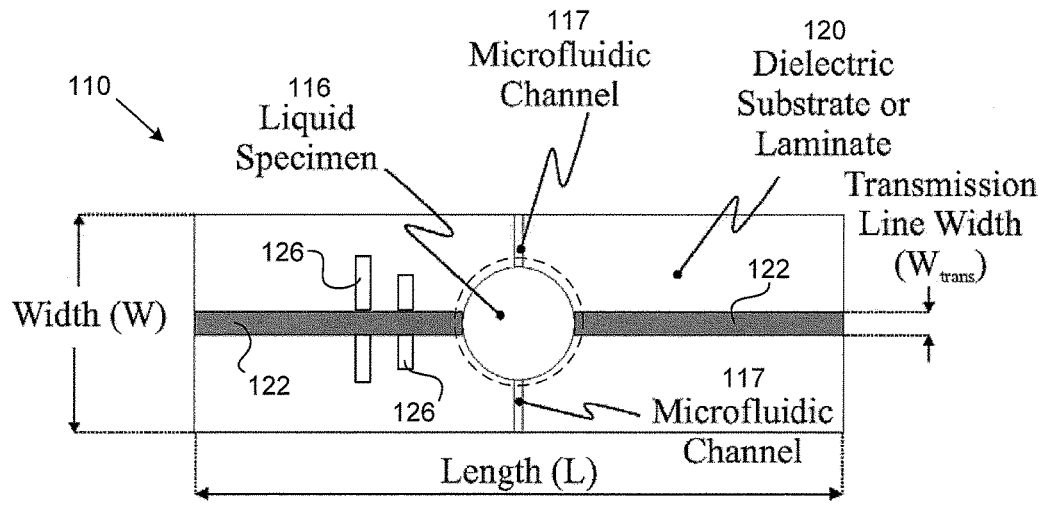
Figure 8D:
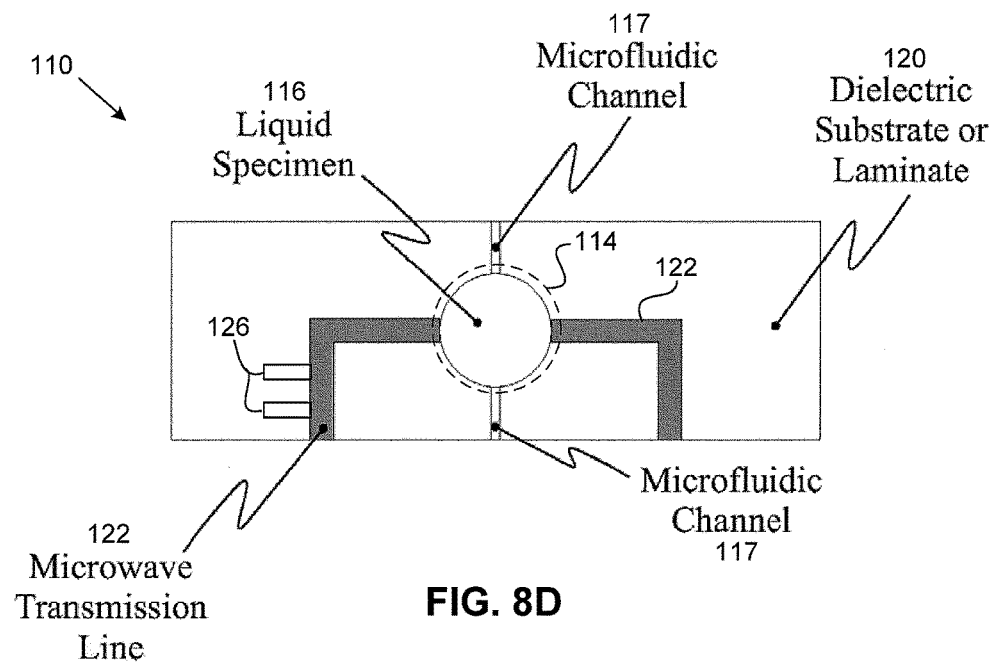
Figure 8E:
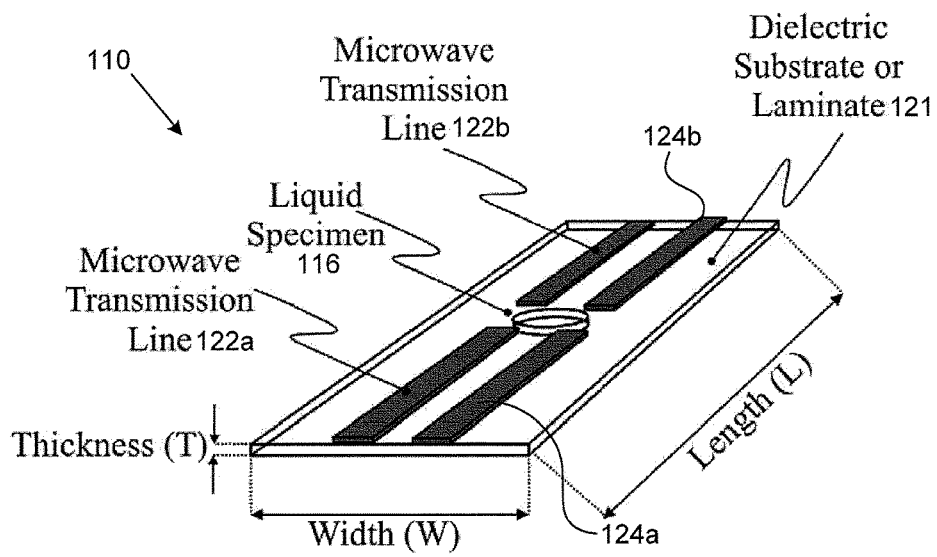
Figure 8F:
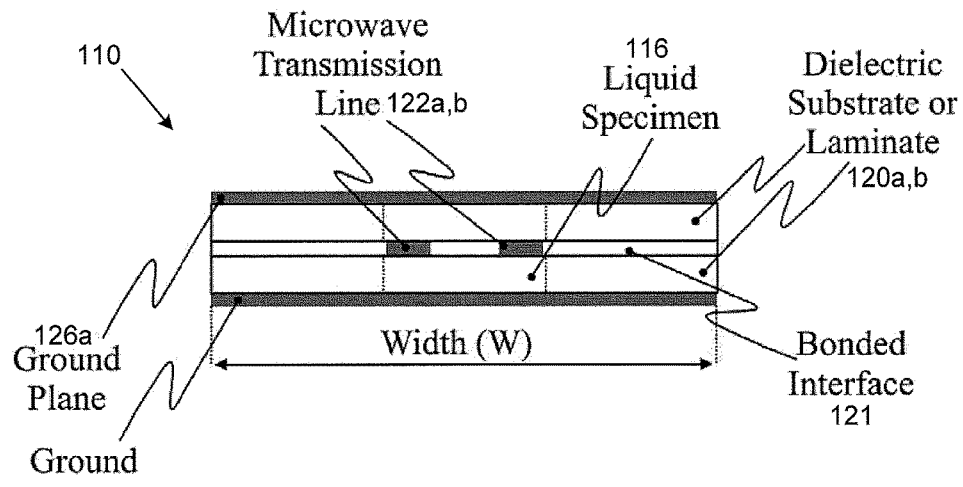

FIGS. 8E-8G are schematic illustrations of a coplanar microstrip capsule structure or assembly 110 in accordance with an embodiment of the present disclosure. In an embodiment, the coplanar microstrip capsule structure 110 includes a set of coplanar microwave signal transmission lines 122*a*1, 122*a*2, 122*b*1, 122*b*2 which are carried by or between a first and a second dielectric substrate or laminate structure 120*a*, *b*, and which are disposed between a first ground plane structure 126*a* and a second ground plane structure 126*b*, as indicated in FIGS. 8F and 8G. A specimen or sample compartment or chamber 116 can be disposable or disposed between transmission line segments as shown, in a manner analogous to that described above. In several embodiments, the transmission lines 122*a,b* can reside within a bondable or bonded interface 121 that structurally couples or assembles the first and second ground plane structures 126*a,b*. Depending upon embodiment details, the bondable interface 127 and the transmission lines 122*a,b* can be formed independent of or separate from one or both of the ground plane structures 126*a,b*, after which appropriate bonding between the bondable interface 127 and one or both ground plane structures 126*a,b* can occur. The manner in which the set of transmission lines 122*a*, 122*b* is disposed between the ground plane structures 126*a,b* provides tight electromagnetic field confinement, and facilitates effective shielding.

While the set of transmission lines 122*a,b* shown in FIGS. 8E-8G corresponds to a pair of conductive traces, other embodiments can be scaled to include a larger number of conductive traces, depending upon embodiment details, electrode configuration, intended microwave radiation distribution characteristics, and shielding considerations. Furthermore, other/additional conductive traces can be added on outer edges of the structure 110, or between trace pairs to provide signal isolation and/or shielding between transmission lines 122 and/or the structure's edges. Additionally or alternatively, various types of circuit structures (e.g., vias, slots, and/or stubs) can be integrated into portions of the structure 110. Moreover, one or more types of cutouts or recesses on feed ends can be provided to make space for and/or facilitate microwave signal delivery into internal portions of the compartment 116. Coupling to a set of electrodes or electrode structures that facilitate microwave signal delivery to internal portions of the compartment 116 can be achieved by way of an appropriate electrical structure, a recess, or a gap feed, depending upon embodiment details. Some embodiments include a signal balancing device such as a balun, which can be externally coupled to or integrated as part of the structure 110. Microfluidic channels can also be provided in a manner analogous or generally analogous to that described elsewhere herein.

Figure 8H:
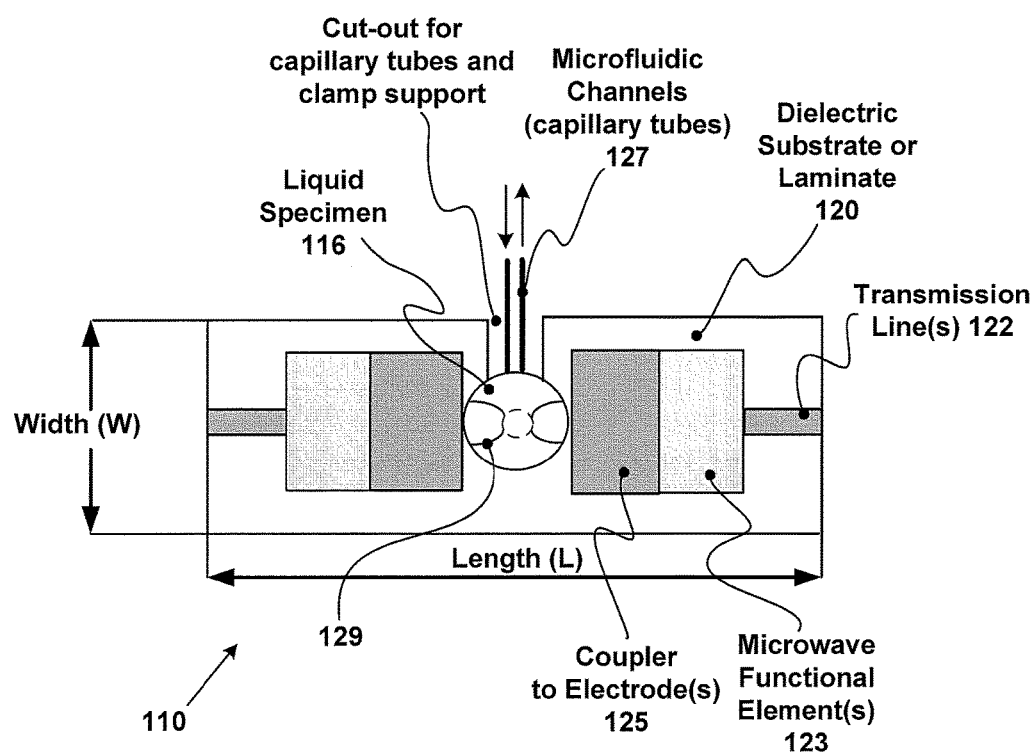
FIG. 8H is a schematic illustration of a generalized microstrip capsule structure or assembly in accordance with an embodiment of the present disclosure.

In view of the foregoing, FIG. 8H is a schematic illustration of a generalized microstrip capsule structure or assembly 110 in accordance with an embodiment of the present disclosure. In an embodiment, the generalized structure 110 includes at least one dielectric substrate or laminate 120 that carries a set of microwave transmission lines 122; a set of microwave functional elements 123, a set of microwave coupling elements 125, possibly a set of microfluidic elements 127; and an electrode based microwave signal applicator 129 (e.g., comprising a set of electrodes) by which microwave energy can be delivered into portions of a sample or specimen chamber or compartment 116. The set of microwave functional elements 123 can include one or more of matching devices (e.g., stubs, or quarter wave transformers); a balun to convert between balanced and unbalanced signal transmission lines 122; a set of phase shifters; a set of power dividers; a set of isolators; a set of microwave opens, shorts, gaps, slots, plated or unplated vias; couplers, controlled length and controlled impedance transmission line elements; microwave resistors, capacitors, or inductors; or other microwave structures or elements as understood by one of ordinary skill in the relevant art.

The set of coupling elements 125 is configured for communicating or delivering microwave signals to the electrode applicator/set of electrodes 129, and can include one or more of metal contact elements and associated mechanical pressure or force application devices that establish electrical signal communication between metal-to-metal contacts; intermediate conductive film(s) between metal-to-metal contact elements, which can facilitate reduced or low contact resistance under pressure or bonding conditions; contact elements that can be selectively and rapidly released after freezing; and gap feeds or gap couplers designed to couple microwave energy from the transmission lines to the electrode applicator 129.

In several embodiments, the size of one or more portions of a capsule structure or assembly 110 is correlated with or corresponds to a standard microscope slide size, such that the capsule structure 110 and associated elements of a sample preparation or fixation system 10 can be readily carried by, used with, or removably/matingly engaged with one or more conventional or generally conventional types of sample/specimen imaging devices, such as an optical microscope. Aspects of a representative embodiment of such a capsule structure 110 is described in detail hereafter with respect to FIGS. 9A-11B.

FIGS. 9A-9D are schematic illustrations of portions a microstrip-based capsule structure or assembly 400 in accordance with yet another embodiment of the present disclosure. FIGS. 10A-10I are illustrations or images corresponding to aspects of the microstrip-based capsule structure 400 of FIGS. 9A-9D. In an embodiment shown in an exploded view in FIG. 9A, the capsule structure 400 includes an extremely high thermal conductivity substrate (hereafter "thermal energy transfer substrate") 112, such as a diamond or sapphire plate or disk, having an underside or bottom face that forms a physical interface to which a cryo-coolant jet 220 can be directed, and an upper side or top face that forms a bottom surface of a specimen or sample compartment, chamber, or cell 116 within which a biological sample or specimen can be disposed. As will be understood by one of ordinary skill in the relevant art, a biological sample can be grown or placed on the upper face of the thermal energy transfer substrate 112. The capsule structure 400 further includes a holding ring 410 that forms exterior portions of the compartment 116; and a microfluidic ring insert 420, which forms internal side walls of the compartment 116. More particularly, the holding ring 410 is configured for carrying, holding, or retaining the thermal energy transfer substrate 112, as well as the microfluidic ring insert 420, which can be matingly engaged with the holding ring 410. The microfluidic ring insert 420 forms an internal region of the compartment 116 that forms a microfluidic cell, which is configured for carrying a specimen and exposing the specimen to a fluid environment by way of microfluidic elements. The microfluidic cell can include a set of flexible fluid capillaries 450 that can be coupled to or inserted into the microfluidic ring insert 420, and which facilitate or effectuate fluid delivery into and fluid withdrawal from the microfluidic cell 416, or fluid circulation therein.

The capsule structure 400 further includes a microwave applicator coverslip 460, which forms a cover 114 for the compartment 116, and which carries a set of excitation elements 500, which can be patterned microwave signal conductors or traces (e.g., an underside of the coverslip) that serve as electrodes by which microwave energy can be provided to internal portions of the microfluidic ring insert 420 to thereby irradiate a sample disposed within the microfluidic cell 116. The microwave applicator coverslip 460 can be manufactured performing standard conductive trace patterning techniques upon a support member or material such as a standard microscope coverslip (e.g., a standard no. 1.5 square quartz coverslip having a thickness of 0.17 mm, and a side length of 22 mm), such as by way of performing optical masking, photolithography, etching, and possibly electroplating to selectively form or define conductive traces in accordance with a predetermined pattern defined by a mask (e.g., a photomask).

Taken together, the thermal energy transfer substrate 112, the microfluidic holding ring 410, the ring insert 420, and the microwave applicator coverslip 460 form or provide a hermetically sealable microfluidic microwave delivery chamber module or sample cell 402, by way of which (a) a specimen or sample disposed within the microfluidic ring insert can be exposed to one or more types of fluids (e.g., a buffer and/or nutrient solution to maintain cell viability; or a chemical substance that can provide a chemical impulse to rapidly change the chemical environment to which a sample is exposed; or a chemical substance such as glutaraldehyde, which can be used in a microwave assisted chemical fixation procedure in which cryofixation or ultra-rapid freezing does not or need not occur); (b) the specimen or sample can be jet frozen as a result of exposure of the underside of the thermal energy transfer substrate 112 to a cryogenic cooling jet 220, and corresponding high efficiency ultra-rapid cooling of the sample from below or underneath the sample; and (c) which can be transferred to a cryogenic environment such as a dewar containing LN, and/or a low temperature high resolution imaging system, for instance, a scanning electron microscope (SEM), a scanning helium ion microscope (SHIM), or other type of very high resolution microscope (e.g., an atomic force microscope (AFM)) having a cold stage configured for cryo-microscopy.

In several embodiments, the sample cell 402 exists in two joinable or sealable (e.g., hermetically sealable) portions, namely, a top or upper portion and a bottom or lower portion. The top portion includes the microwave applicator coverslip 460, the microfluidic ring insert 420, the capillaries 450, and the holding ring 410, each of which can be joined together (e.g., by way of appropriate bonding) to form a single or integrated unit prior to combining with the bottom portion, which includes the thermal energy transfer substrate 112. An embodiment of an assembled microfluidic microwave delivery chamber module or sample cell 402 is shown in perspective view in FIG. 9B. One or more portions of the microwave delivery chamber module or sample cell 402, such as its top portion, can form a disposable unit that can be manufactured reliably an inexpensively.

In several embodiments, a sealing structure or apparatus, which can include a hemostat type mechanism, can securely apply pressure or force to or across portions of the microwave delivery chamber module or sample cell 402 to facilitate hermetic sealing. The sealing structure or apparatus simultaneously aligns (e.g., self-aligns) and clamps the thermal energy transfer substrate 112, the holding ring 410, and the microwave applicator coverslip 460. In some embodiments, a sealing apparatus can include a set of forceps configured for holding and sealing the microwave delivery chamber module or sample cell 402.

The holding ring 410 serves to securely retain the thermal energy transfer substrate 112 as well as the microfluidic ring insert 420 and the sample (e.g., a vitrified biological specimen) from below. The holding ring 420 can be formed or machined using one or more materials that (a) exhibit high or very high material stability and thermal stability at cryogenic temperatures; (b) exhibit microwave compatibility; (c) can be machined or formed in accordance with tight or very precise mechanical tolerances; and (d) is vacuum compatible or exhibits minimal or negligible outgassing under vacuum conditions. In a representative embodiment, the holding ring 410 includes or is made of Vespel, and/or another suitable type of polymer material. The holding ring 410 can carry a set of fiducial markers that can be identified under an optical microscope as well as a SEM, a SHIM, or other type of very high resolution microscope, in order to facilitate correlative microscopy procedures. The thermal energy transfer substrate 112 can also carry one or more types of fiducial markers or substrate location reference structures in order to facilitate correlative microscopy procedures. However, following sample vitrification, fiducial markers carried by the thermal energy transfer substrate 112 may not be detectable, imageable, or viewable. Thus, in various embodiments, the microfluidic microwave delivery chamber module or sample cell 402 can include a first set of fiducial markers internal to the compartment 116 and a second set of fiducial markers external to the compartment 116.

Figure 9A:
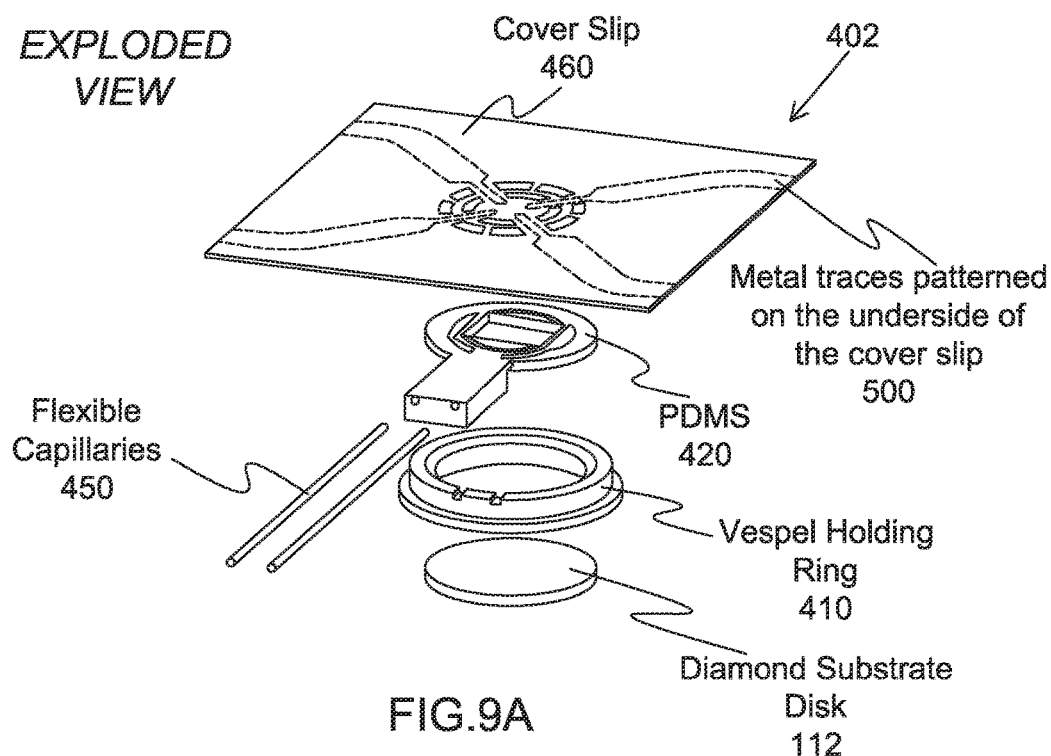
FIGS. 9A-9D are schematic illustrations of portions a microstrip-based capsule structure or assembly in accordance with yet another embodiment of the present disclosure.
Figure 9B:
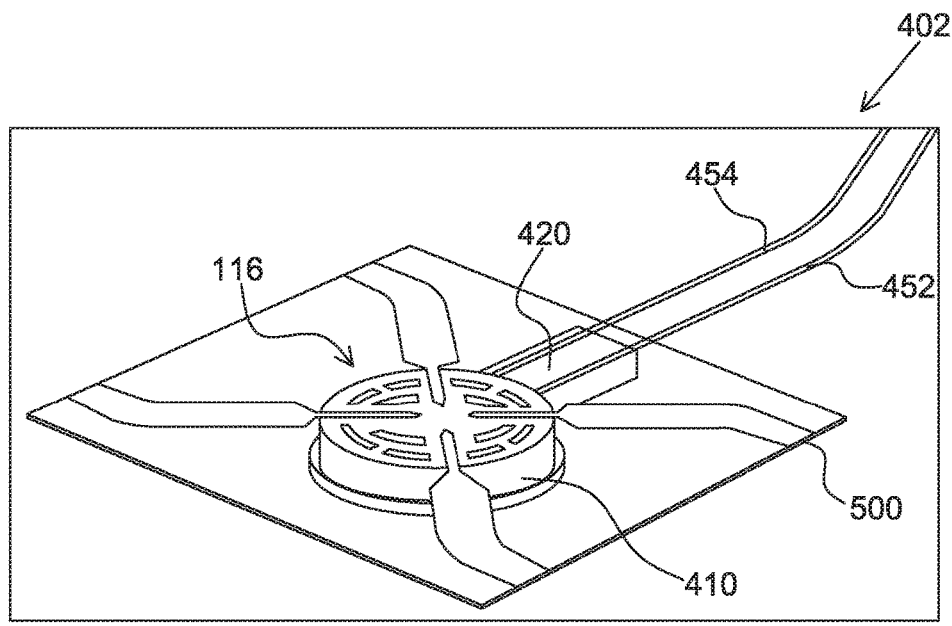
Figure 9C:
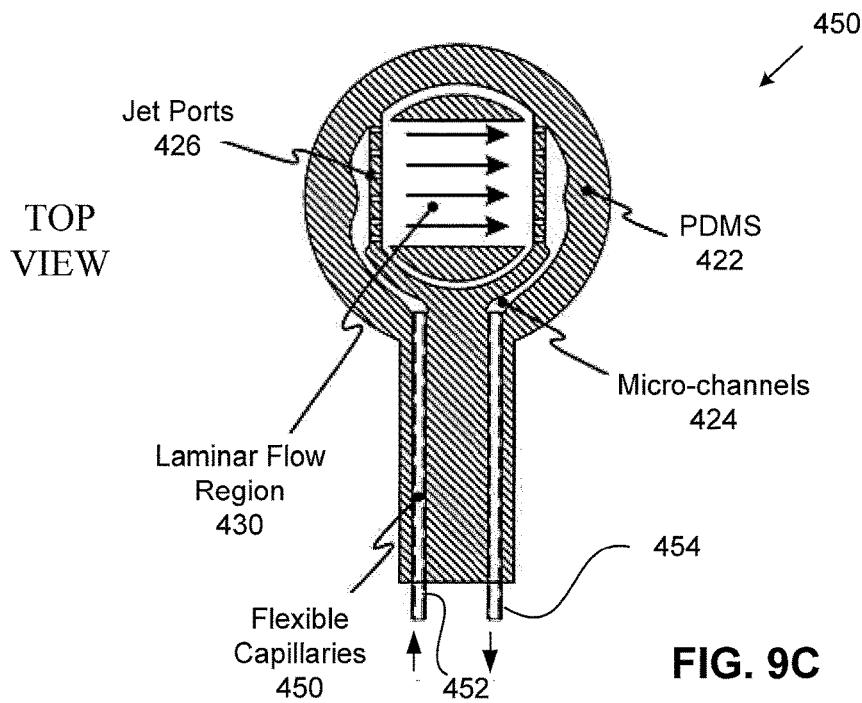
Figure 9D:
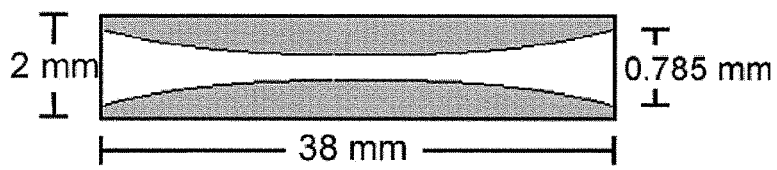

FIG. 9C is a plan view showing portions of a microfluidic ring insert 420 in accordance with an embodiment of the present disclosure. In an embodiment, the microfluidic ring insert 420 includes a main body 422 in which a set of micro-channels 424 are formed; a set of jet ports 426 capable of fluid communication with the micro-channels 424; and a laminar, substantially laminar, or approximately laminar flow region 430 configured for fluid communication with the set of jet ports 426. At least one fluid input capillary 452 and at least one fluid output capillary 454 can be inserted into the main body 422 and fluidically coupled to corresponding micro-channels 424 therein, such that fluid can be communicated or conveyed into and out of the laminar flow region 430. In some embodiments, the main body 422 is fabricated or machined to include tapered micro-channel portions that can provide a secure friction fit fluid seal (e.g., by way of Inner-Lok™ friction fit structures or elements, Polymicro Tehnologies, Phoenix, Ariz. USA) to the fluid input and fluid output capillaries 452, 454, in a manner indicated in FIG. 9D. The capillaries 452, 454 can be made of glass, and coated with a cryogenic compatible jacket to enable flexure without cracking. The capillaries 452, 454 can be fluidically coupled to other fluid transfer structures (e.g., other capillaries or tubes) using push-fit connector elements that facilitate quick connect/disconnect.

The microfluidic ring insert 420 and the flexible fluid capillaries 452, 454 are configured for providing a microfluidic cell, chamber, or compartment having minimal dead volume and an engineered laminar flow region 430 that is fed by the capillaries 454, 454. The jet ports 426 can affect or control the flow of fluid into and across the laminar flow region 430, and hence the flow of fluid toward, to, across, and/or around a specimen or sample (e.g., a biological specimen) that resides within the laminar flow region 430. Particular representative manners in which the microfluidic ring insert 420 can be implemented, including the jet ports 425 are provided by Elisabeth Verpoorte and Nico F. De Rooij in "Microfluidics meets MEMS," *Proceedings of the IEEE*, Vol. 91, No. 6, June 2003.

The microfluidic ring insert 420 can be made using a moldable material. For instance, the microfluidic ring insert 420 can be injection molded using a material such as polydimthylsiloxane (PDMS), which exhibits suitable material and thermal properties in a manner analogous to that indicated above for the holding ring 410, as well as compatibility with biological specimens or samples. For injection molding, a stainless steel mold or form can provide a microfluidic ring insert 420 having smooth surfaces and minimal surface roughness. The holding ring 410, the flexible capillaries 450, and the microwave applicator coverslip 460 can be placed in the mold such that the PDMS microfluidic ring insert 420 spatially forms around them, and such parts are automatically bonded together. The open ends of the capillary tubes 452, 454 are temporarily sealed, prior to molding, in order to prevent backflow of liquid PDMS therein when injection molding occurs. Silanization can be carried out on mold parts to passivate surfaces and enable the formed microfluidic ring insert 420 to easily disengage from the mold. Additionally, the surfaces of the mold that come into contact with the microwave applicator coverslip 460 are maintained in a highly flat and even condition to prevent the application of uneven stress on the coverslip 460 or cracking the coverslip 460 when the mold is sealed shut.

Figure 9E:
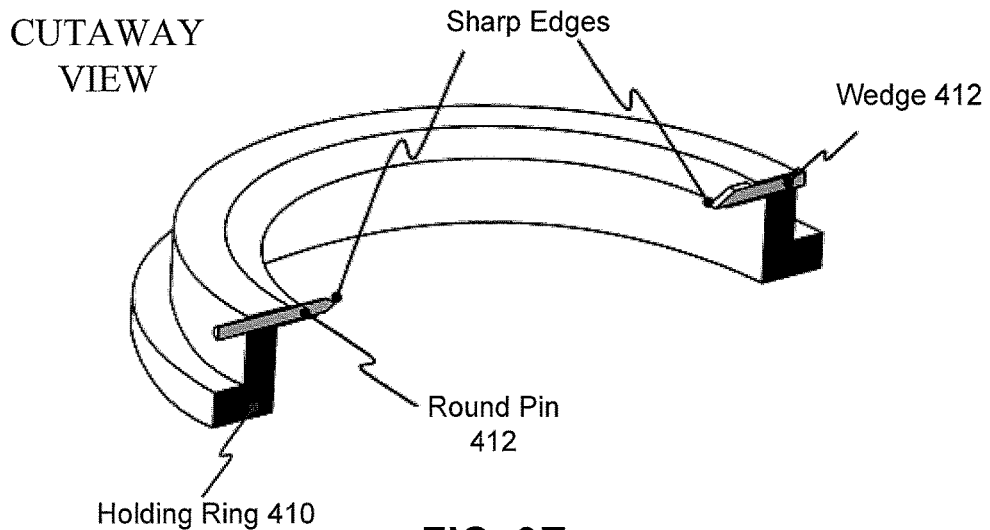
FIG. 9E is a schematic illustration of a representative type of fracture initiation element carried by a microstrip-based capsule structure or assembly in accordance with an embodiment of the present disclosure.

In various embodiments, the holding ring 410 and possibly the microfluidic ring insert 420 are configured for carrying at least one fracture initiation element 412, such as a tungsten wire or a wedge, which can facilitate or enable in-situ freeze fracturing (e.g., when the microfluidic microwave delivery chamber module 402 is carried by a stage or platform assembly inside a very high resolution imaging device, such as a SEM or SHIM. The fracture initiation element 412 can be carried by or secured or embedded within the holding ring 410 and possibly the microfluidic ring insert 420 at a predetermined height or distance (e.g., approximately 10 microns, 25 microns, or 50 microns, depending upon a specimen or sample under consideration) away from an exposed surface (e.g., the upper surface) of the thermal energy transfer substrate 112 that carries a frozen specimen or sample, to facilitate sample imaging at a predetermined freeze depth or height relative to the upper surface of the thermal energy transfer substrate 112. A representative type of fracture initiation element 412 is shown in FIG. 9E.

As indicated in FIGS. 10A and 10B are plan view and side view illustrations of portions of a microstrip-based capsule assembly 400 in accordance with an embodiment of the present disclosure. As indicated in FIGS. 10A and 10B, the assembly 400 further includes a dielectric substrate 600 such as a printed circuit board (PCB), on which conductive traces 610 reside. The dielectric substrate 600 can be shaped and dimensioned to have a size that matches or substantially matches the size of a standard microscope slide. In a representative implementation, the dielectric substrate 600 can include a Rogers RO3010 laminate (10 GHz), or a Rogers RO4003C laminate (5.85 GHz). The dielectric constants of Rogers RO3010 and RO4003C and are 10.2 and 3.55, respectively.

In several embodiments, the conductive traces 610 on the dielectric substrate 600 form a set of Wilkinson power dividers, which provide isolation and minimize crosstalk between output ports, with the addition of surface mount RF resistors 612 (e.g., 100 Ohm resistors) while maintaining a matched condition among input and output ports, in a manner understood by one of ordinary skill in the relevant art. The Wilkinson power dividers can include resistors 612, as also understood by one of ordinary skill in the relevant art.

The conductive traces 610 can be coupled to a microwave signal source by way of a set of connectors 700, such as microwave subminiature version A (SMA) connectors. A holding base or stage/platform structure 800 can carry or support the microstrip-based capsule assembly 400, such that the thermal energy transfer substrate 112 is above a cryogenic cooling jet 220, which can be supplied by a cryo-jet nozzle 222.

The microwave applicator coverslip's excitation elements 500 have different dimensions than the dielectric substrate's conductive traces 610 due to the dielectric properties of the quartz coverslip on top and the aqueous medium below the excitation elements 500. Numerical simulation can be utilized to determine excitation element width, such that a desired electromagnetic field distribution within the sample region 116 can be achieved. In a representative embodiment, an excitation element width corresponding to a microwave frequency of 5.85 GHz can be approximately 0.5 mm. A corresponding excitation element thickness can be selected to achieve low resistivity and reliable electrical contact with the dielectric substrate's conductive traces 610.

Figure 10C:
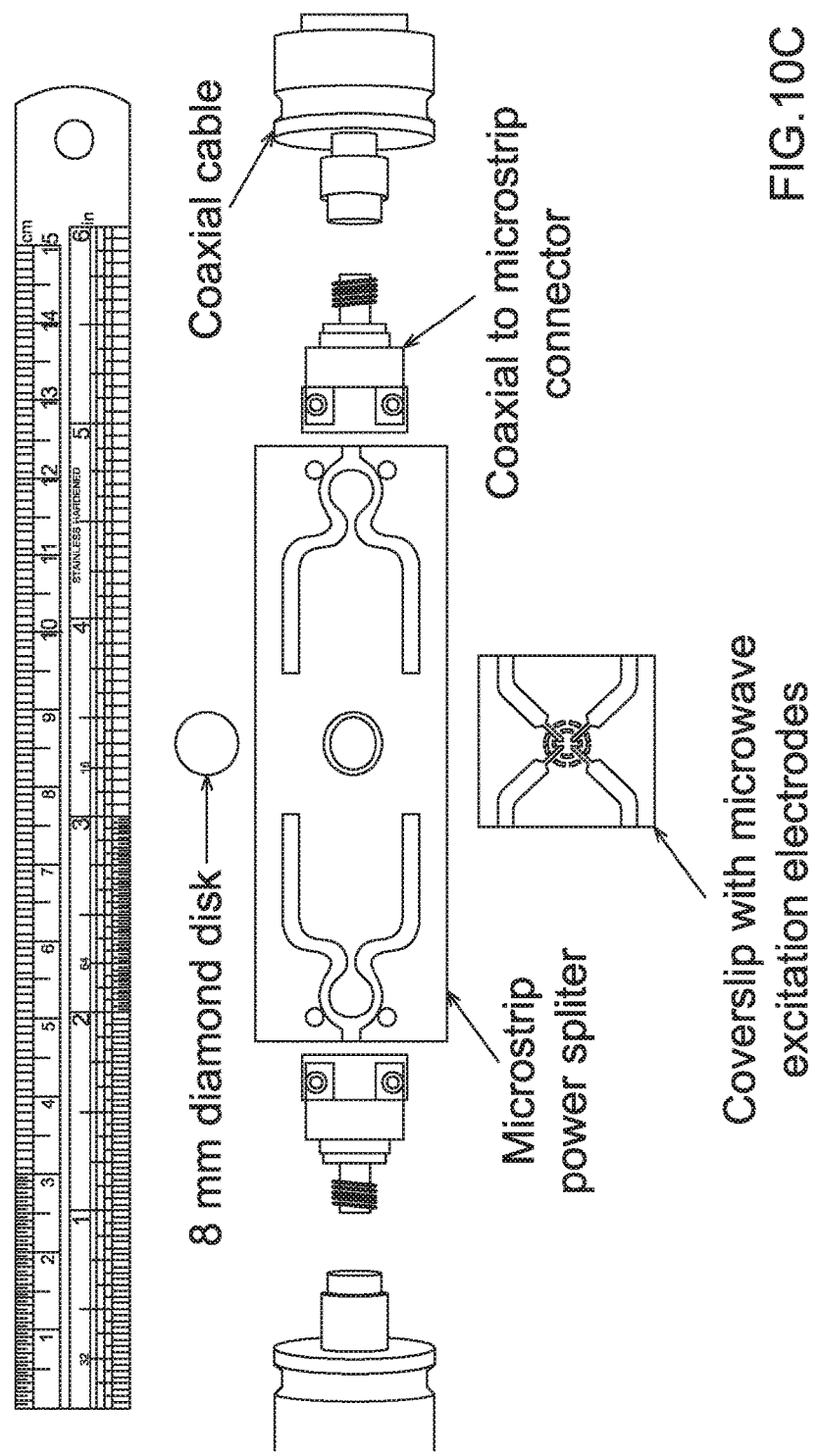
FIGS. 10C-10I are illustrations showing particular aspects of the microstrip-based capsule structure of FIGS. 9A-10B.
Figure 10D:
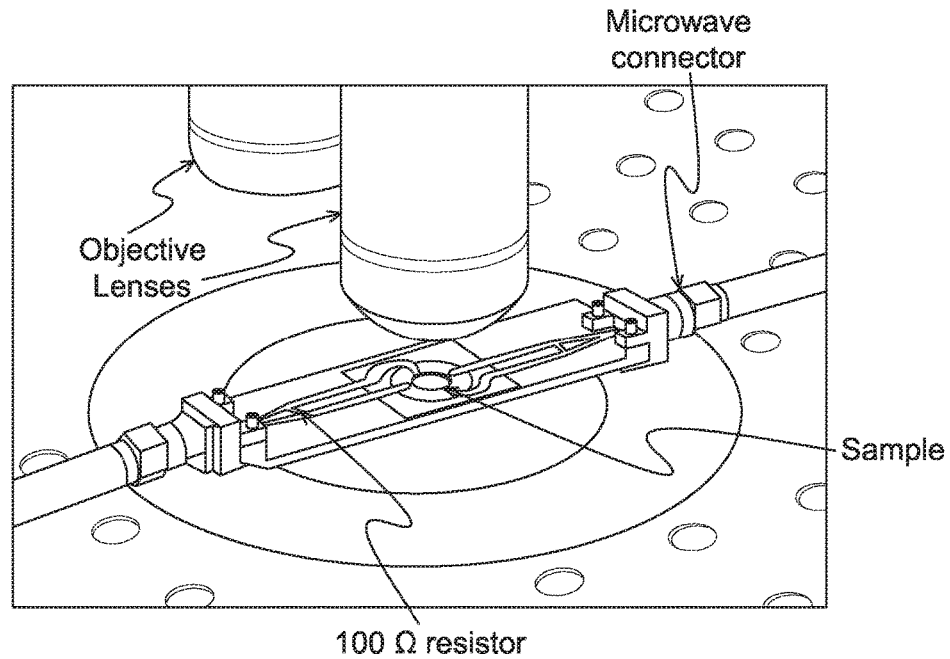
Figure 10E:
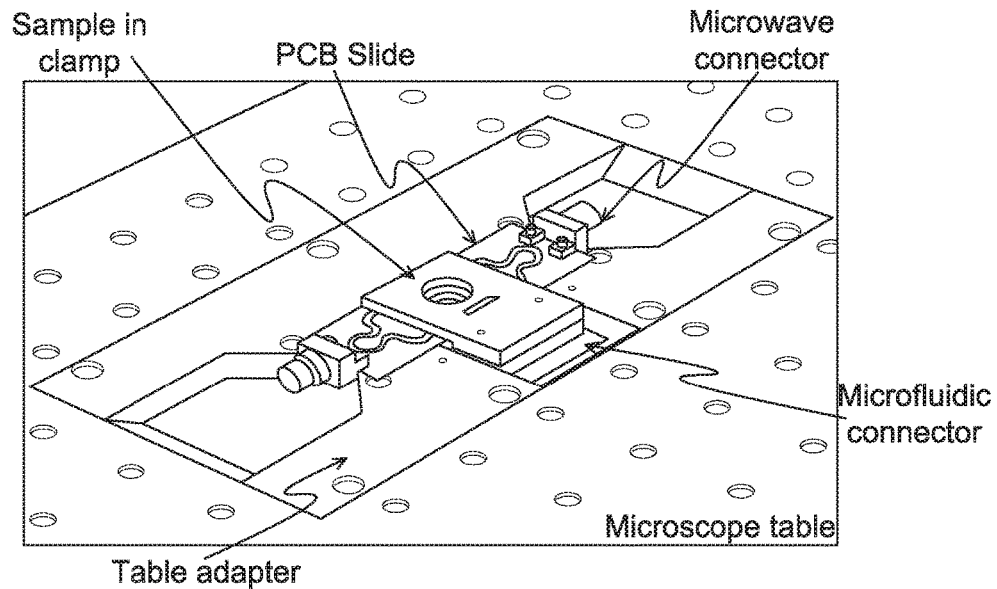
Figure 10F:
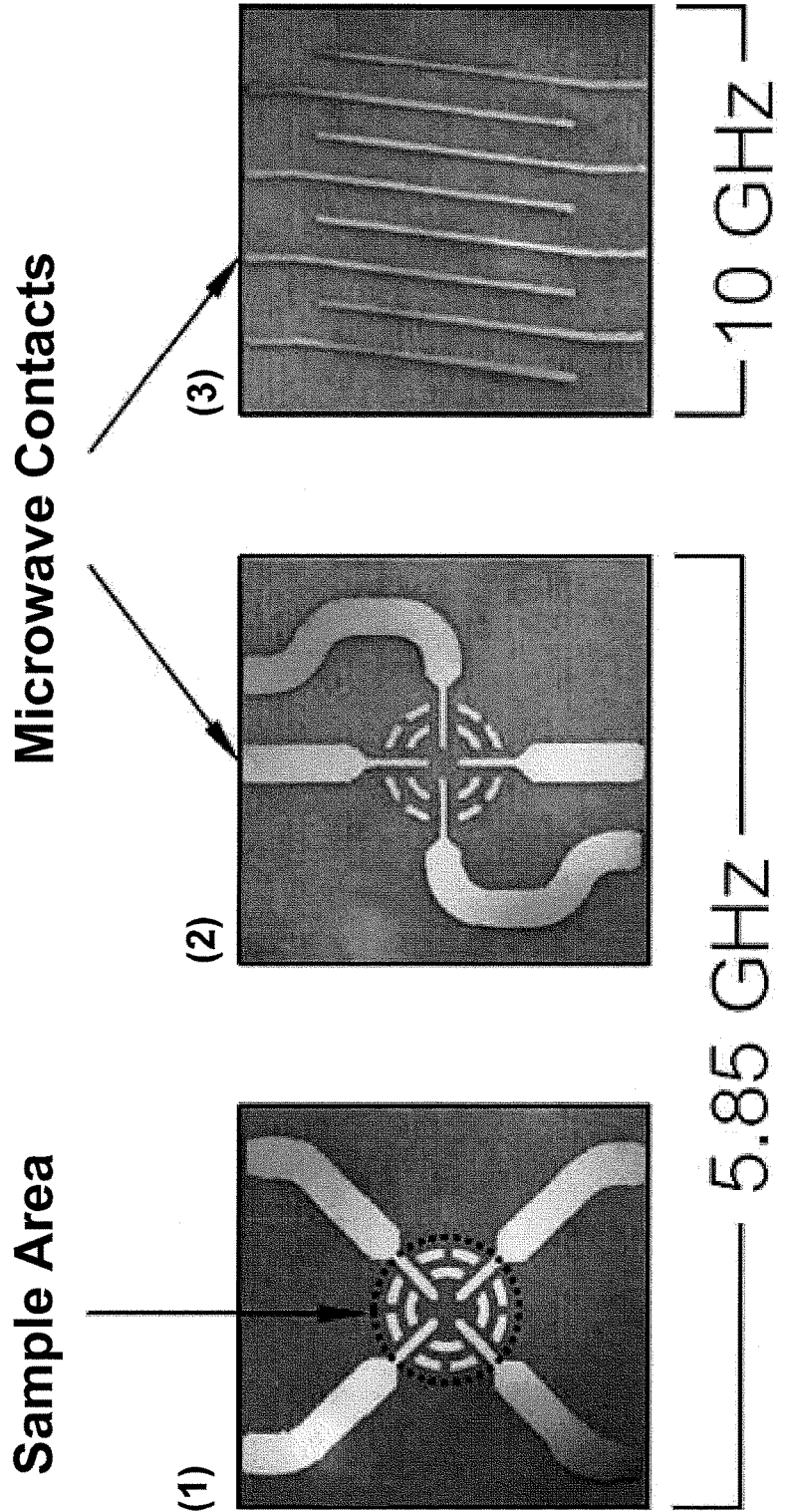

FIGS. 10C-10E are images showing portions a representative implementation of the microstrip-based capsule assembly 400 of FIGS. 9A-10B, positioned relative to a platform or stage of an optical microscope. In an embodiment, electrical signal communication between the microwave substrate's conductive traces 610 and the microwave applicator coverslip's excitation elements 500 can occur by way of direct metal-to-metal contact therebetween, which can be facilitated by way of mechanical pressure or force that results in reliable electrical contact. As indicated in FIG. 10E, such mechanical pressure or force can be provided by a clamp structure that is disposable over the microwave applicator coverslip 460, and which can apply as a gentle downward pressure or force upon the microwave applicator coverslip 460 to establish electrical contact between the coverslip's excitation elements 500 and the microwave substrate's conductive traces 610.

Figure 10G:
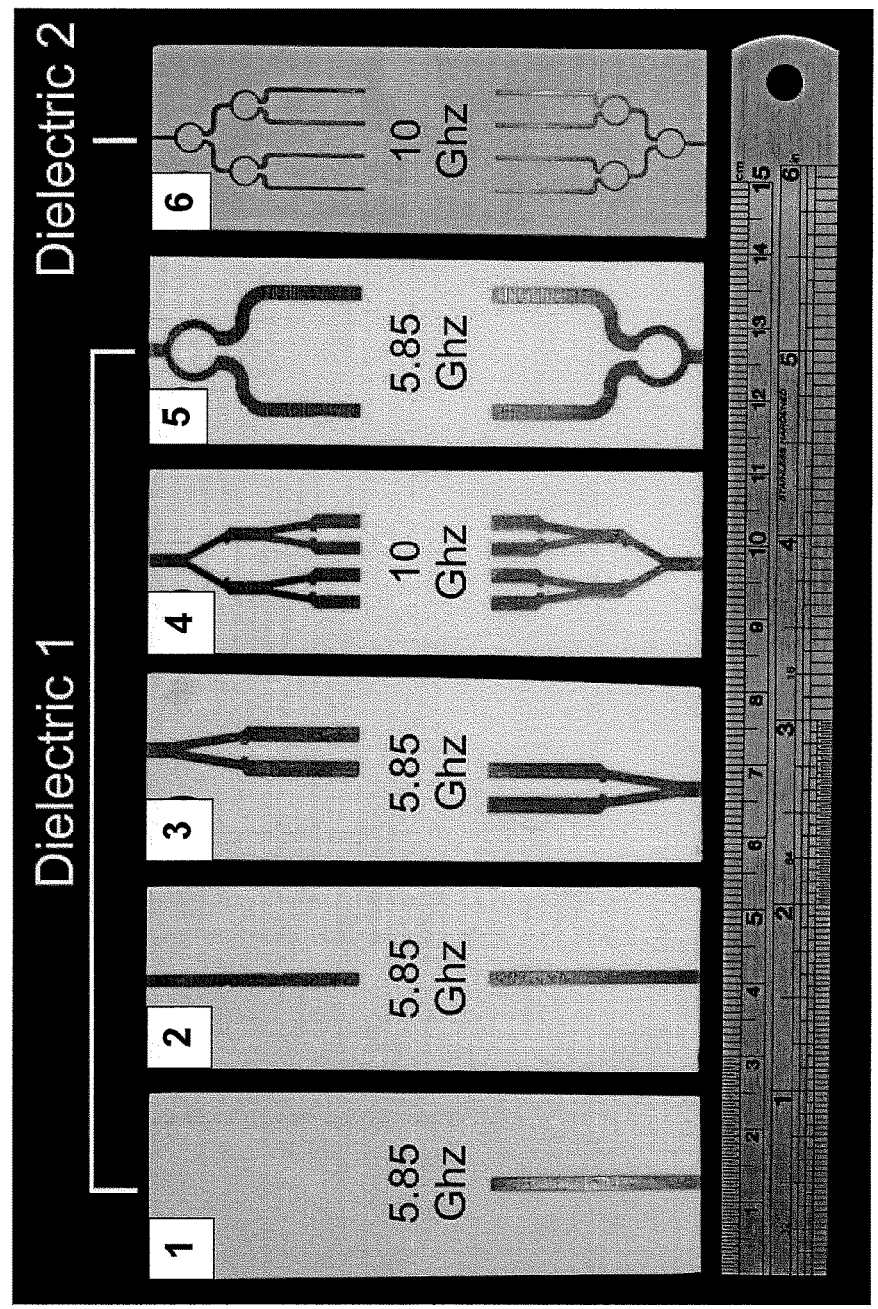

Various configurations, layouts, or designs are possible for the coverslip's excitation elements 500, for instance, depending upon a microwave frequency under consideration. For instance, FIG. 10F includes images depicting multiple representative types of excitation element designs in accordance with particular embodiments of the present disclosure. In general, excitation elements 500 are designed to (a) minimize electrode coverage relative to the surface area of the coverslip 460, which provides optical access for sample imaging; and (b) maximize microwave field strength and absorption uniformity across the sample within the microfluidic cell 420. In a manner analogous to that for the excitation elements 500, various configurations, layouts, or designs are possible for the microwave substrate's conductive traces 610. FIG. 10G includes image depicting multiple representative types of microwave substrate conductive trace layouts in accordance with particular embodiments of the present disclosure.

Figure 10H:
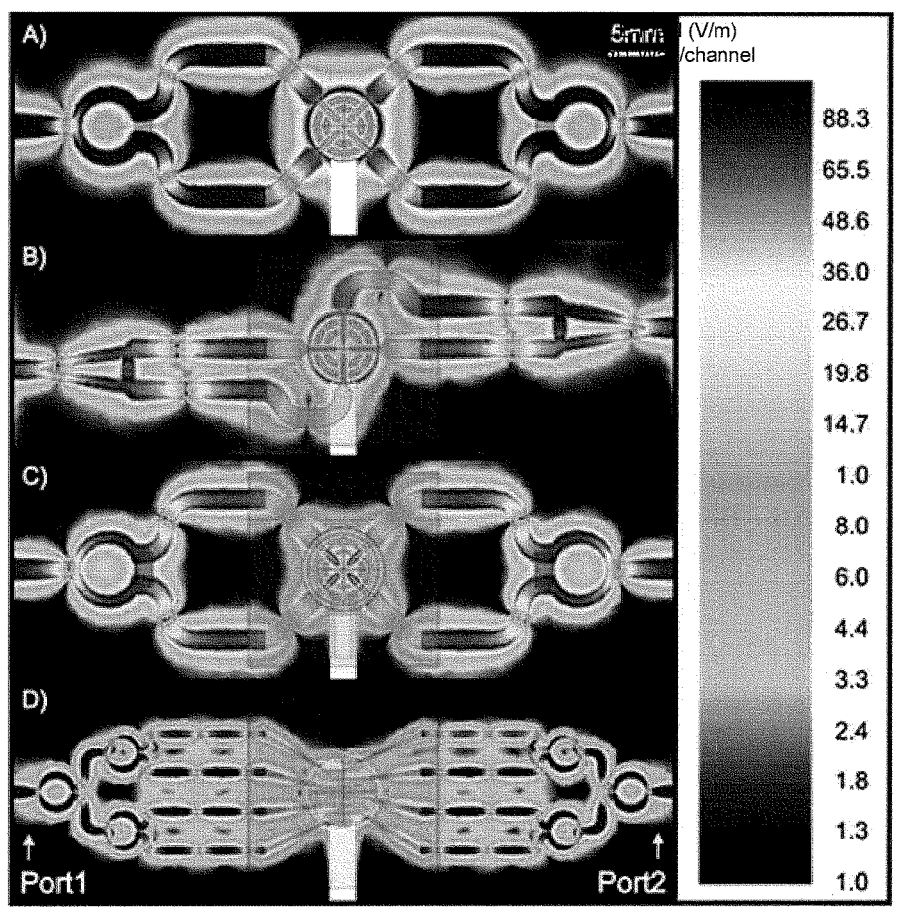
Figure 10I:
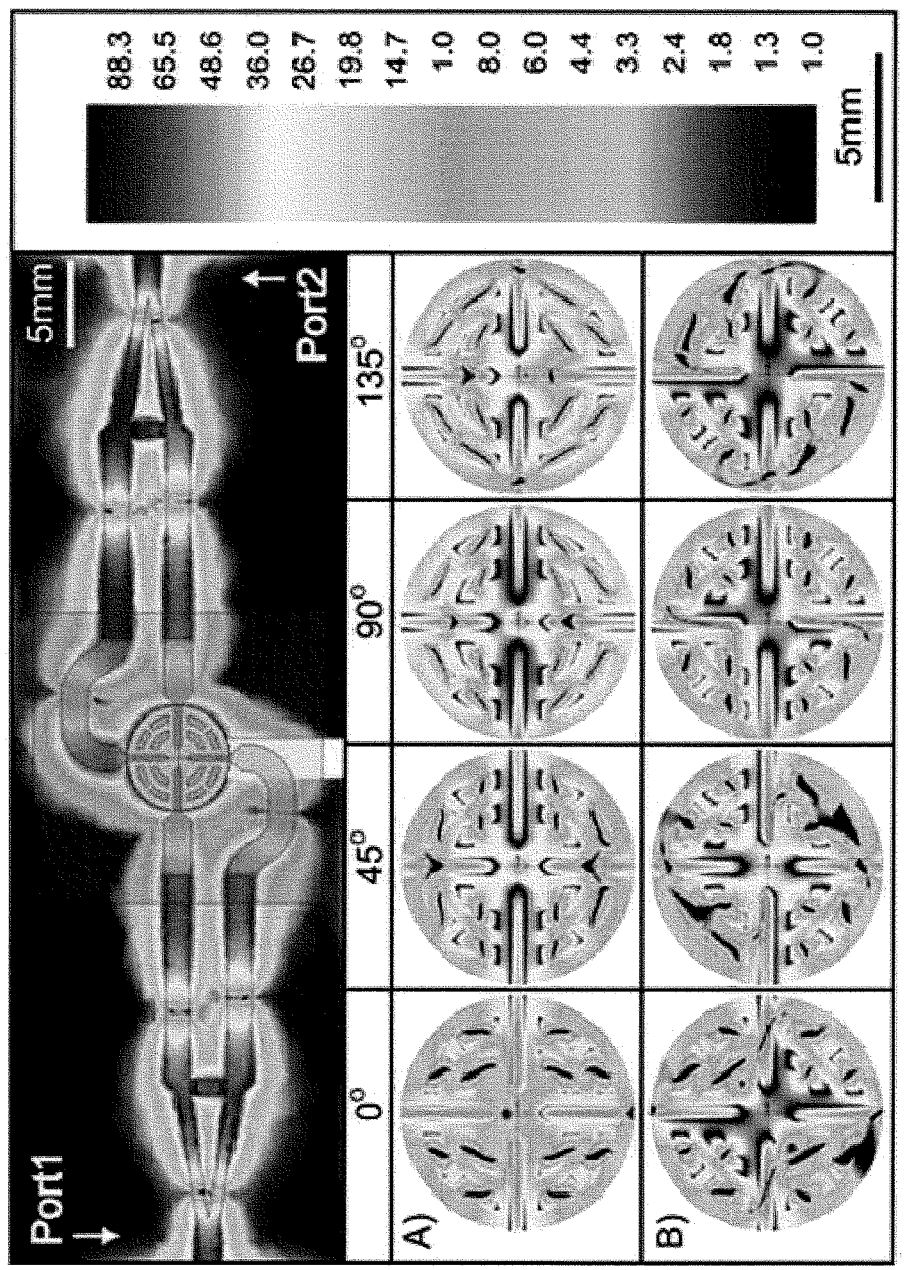

Representative electric field simulation results corresponding to different coverslip excitation element layouts and microwave substrate conductive trace layouts are shown in FIGS. 10H and 10I. Such simulation can facilitate the optimization of the energy deposition and uniformity, while maintaining large electrode free regions for sample observation. As indicated in FIG. 10I, the phase of the microwaves can be shifted between alternating pulses to generate a vortex field pattern to expand the microwave energy distribution more uniformly across the sample. In FIG. 10I, the E-field distribution for a half cycle is confined near the excitation elements 500, where the sample is not visible optically. In FIG. 10I(1), there is no phase difference between port 1 and 2 (e.g. a push-push field); In FIG. 10I(2), the E-field distribution is for half cycle when there is 180 degree phase difference between port 1 and 2 (e.g. push-pull). Rotation of the phase in (2) between alternating pulses delivers a more uniform time-averaged energy distribution.

Figure 11A:
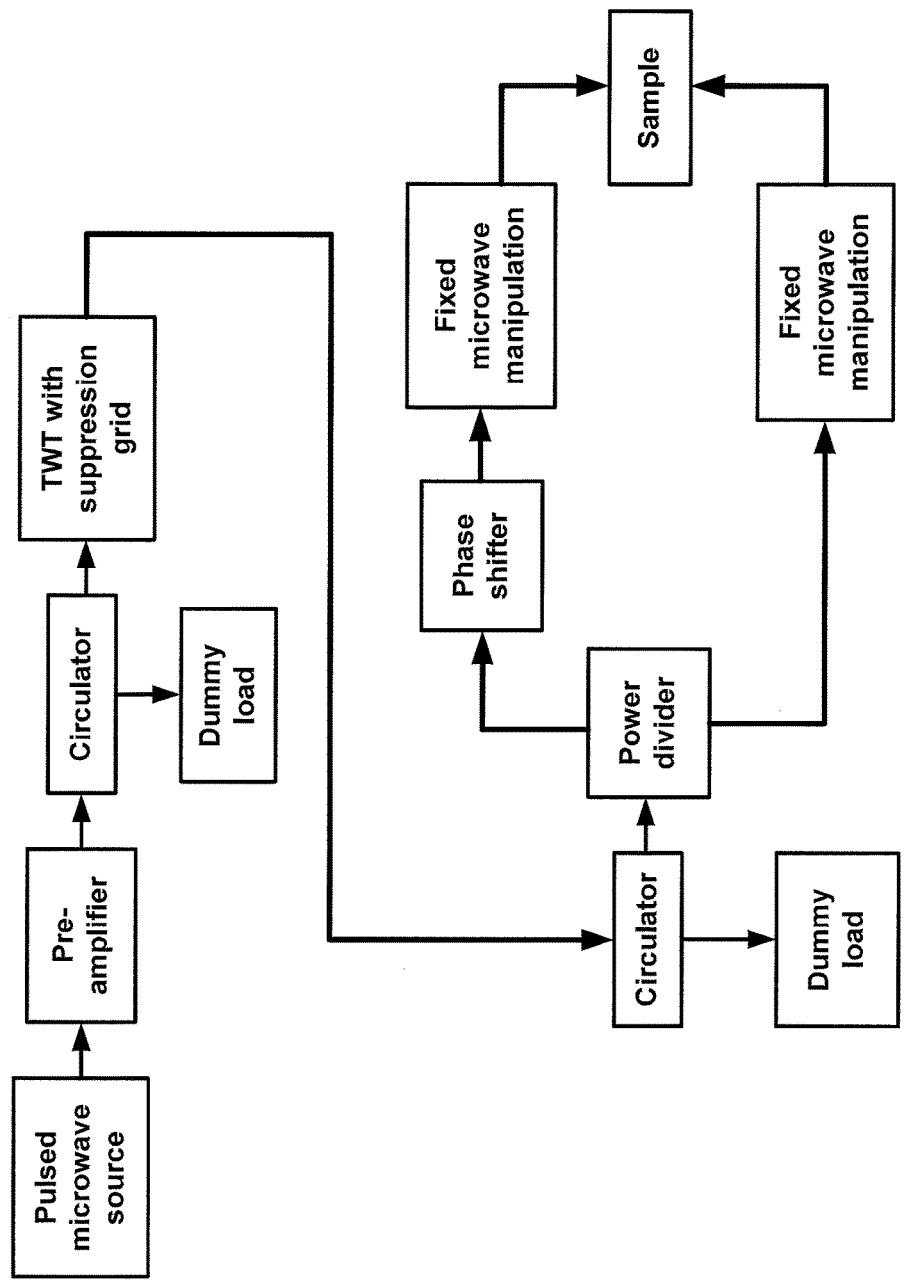
FIGS. 11A-11D are block diagrams showing aspects of a design for microwave signal generation and delivery circuitry in accordance with an embodiment of the present disclosure.

FIGS. 11A-11D are block diagrams showing aspects of a design for microwave signal generation and delivery circuitry in accordance with particular embodiments of the present disclosure, such as the microstrip-based capsule assembly 400 of FIGS. 9A-10E. In FIG. 11A, a pulsed microwave source (e.g., an Anritsu MG3694C, Anritsu Electric Corporation, Kanagawa, JP) provides pulsed microwave signals and allows flexible control of a pulse train, frequency, and amplitude. A traveling wave tube (TWT) amplifier has high headroom for reliable operation, and a suppression grid at its output that allows thermal amplifier noise to be eliminated during steady off state periods. Circulators with dummy loads protect devices from reflected power caused by circuit mismatches. The power divider separates the pulsed microwave signal into two feeds, and a phase shifter is used to control the relative phase between feeds. The darkened lines in FIG. 11A indicate phase stable connections/signals at latter portions of the circuit. Fixed microwave manipulation elements include matching networks, and further features on a dielectric substrate (e.g., PCB) side. Such elements can include baluns, Wilkinson power dividers, matching elements, phase shifters, or other types of elements.

Figure 11B:
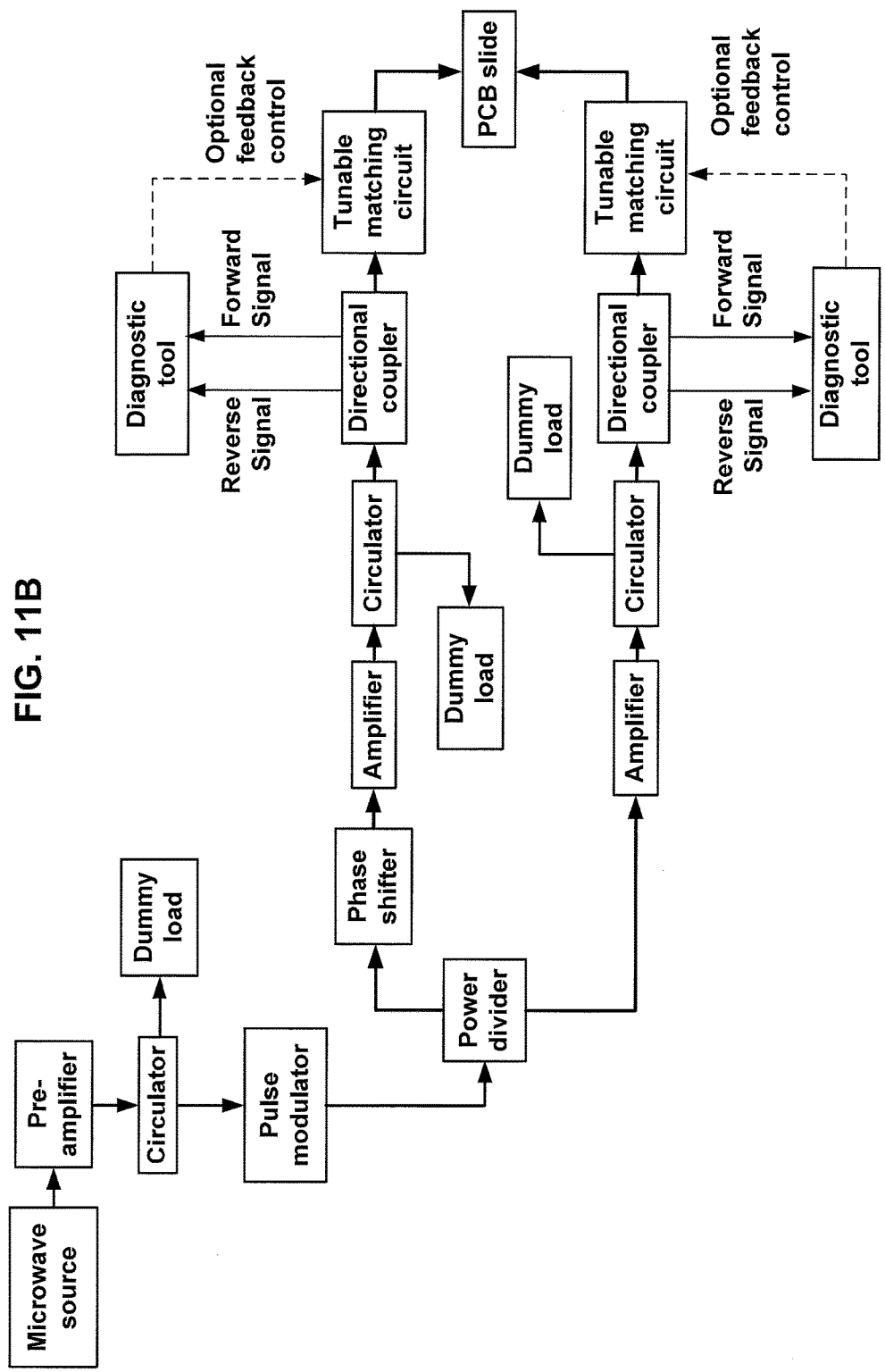

In FIG. 11B, an alternative topology is considered, having different microwave sources and separate external pulse modulation. Multiple low cost amplifiers can be used instead of a single TWT amplifier. Tunable matching is also shown. A low cost continuous wave microwave source is used in this embodiment instead of a complex signal generator, which necessitates independent pulse modulation. A fast switching PIN switch can be used, for example, to achieve desired or required pulse modulation. A low level signal is split by way of a power divider, and separate low cost amplifiers amplify each channel separately. Multiple low power amplifiers can be used to achieve higher total power output, in a manner readily understood by one of ordinary skill in the relevant art.

Impedance mismatches can arise from inaccuracies in construction or changes in environmental factors. The right side portion of FIG. 11B indicates how a directional coupler and a tunable matching network can be used to achieve dynamic impedance matching. The directional coupler re-routes reverse power signals that are indicative of an impedance mismatch. By using a diagnostic tool, the impedance mismatch can be estimated and compensated for by adjusting the tunable matching network. Finally, a tuning process can be automated, such that dynamic matching can be performed in real time to compensate for impedance changes when ultra-fast freezing is carried out. The signal is fed to the dielectric substrate/PCB side, where additional microwave circuit elements can exist in a manner understood by one of ordinary skill in the relevant art.

Figure 11C:
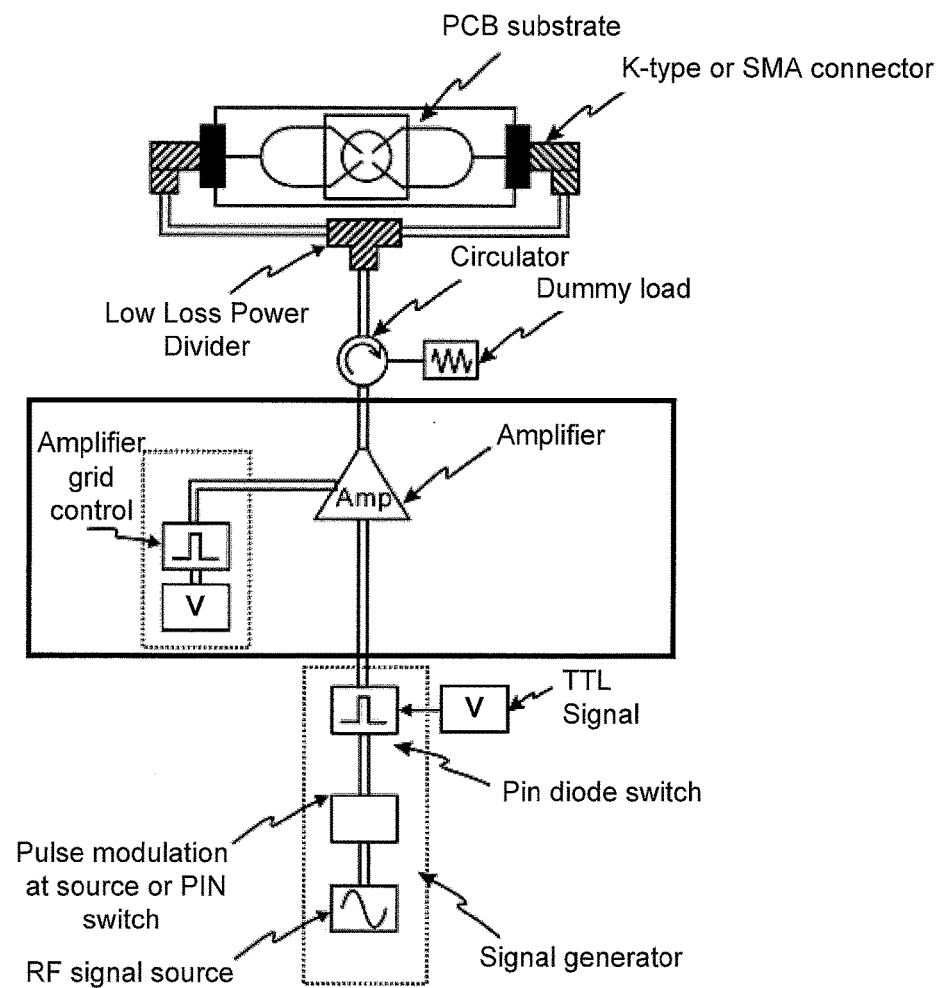
Figure 11D:
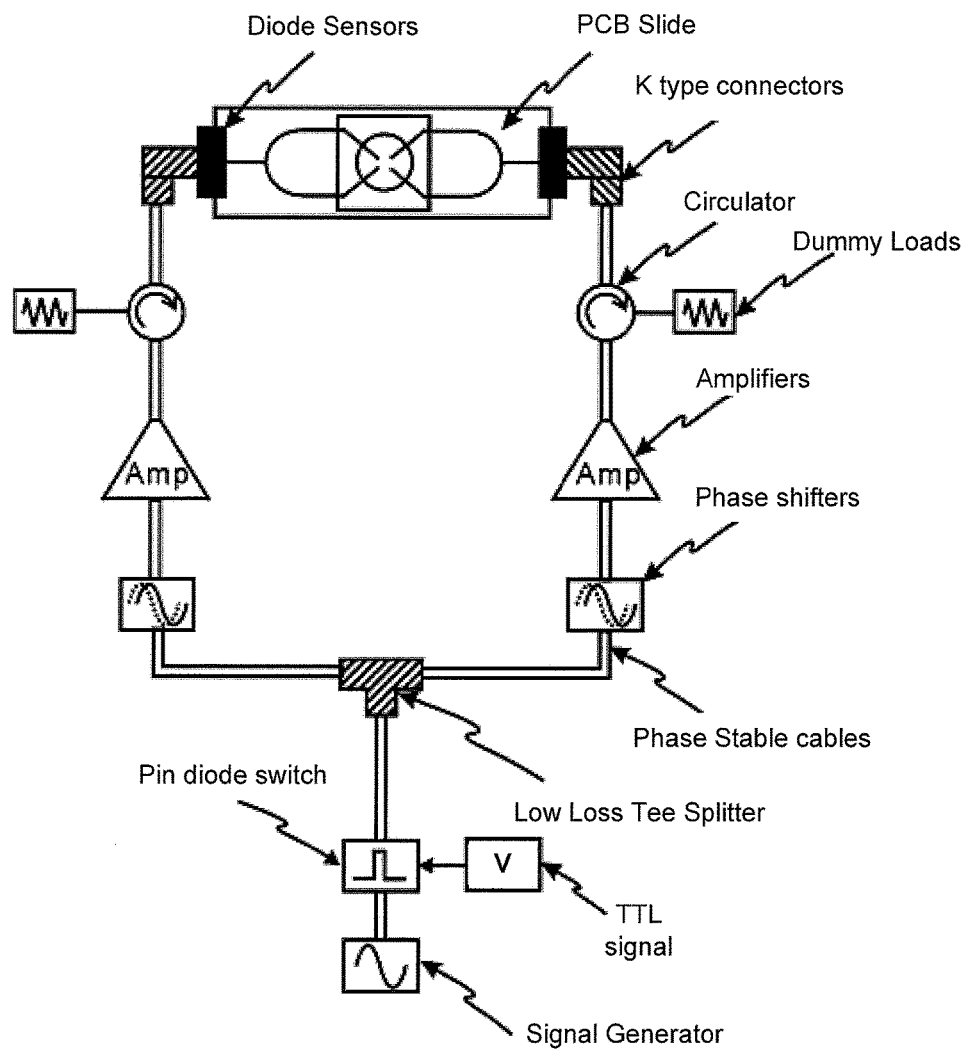

FIG. 11C is a circuit schematic diagram illustrating a representative manner of providing two signals to dual ports of a PCB board; and FIG. 11D is a circuit schematic diagram illustrating representative aspects of phase calibration between dual ports of a PCB circuit.

Figure 11E:
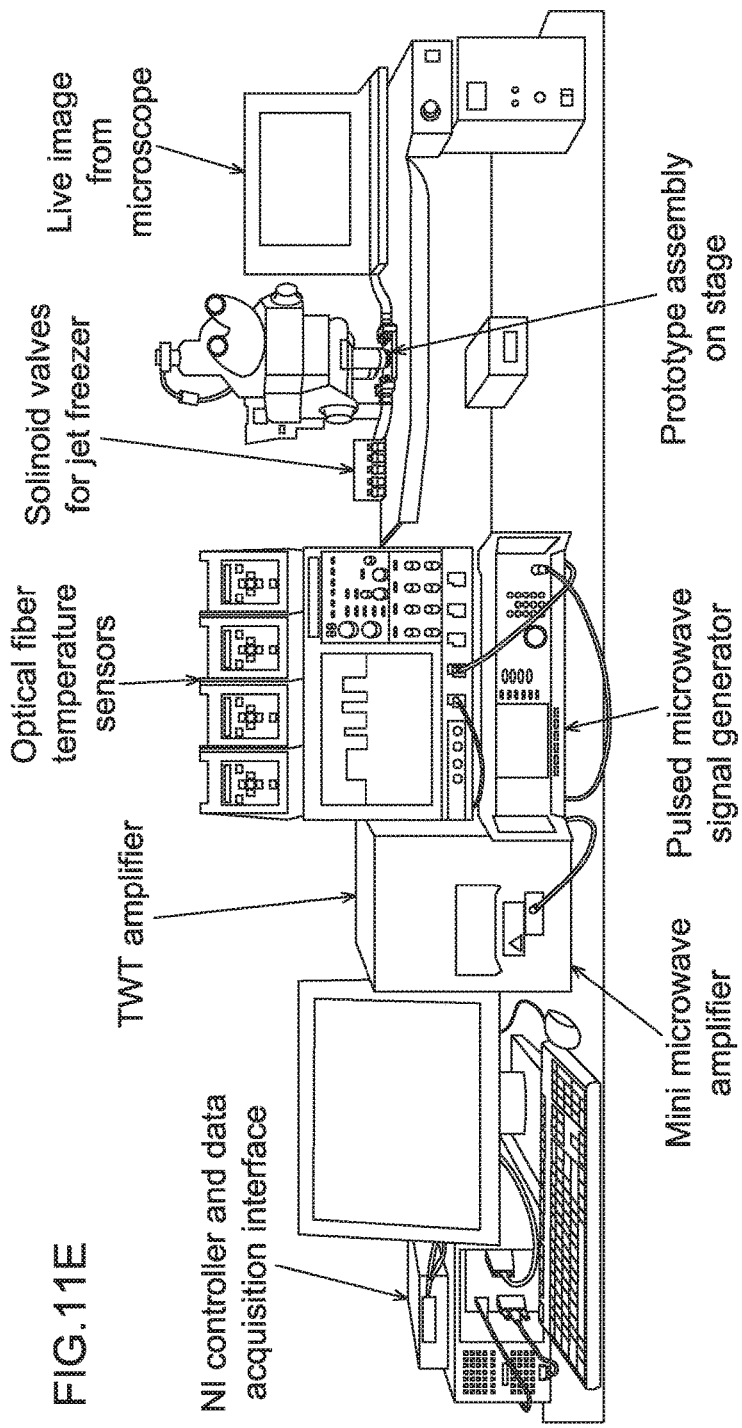
FIG. 11E is an image showing portions of a representative prototype sample preparation or fixation system in accordance with an embodiment of the present disclosure.
Figure 13A:
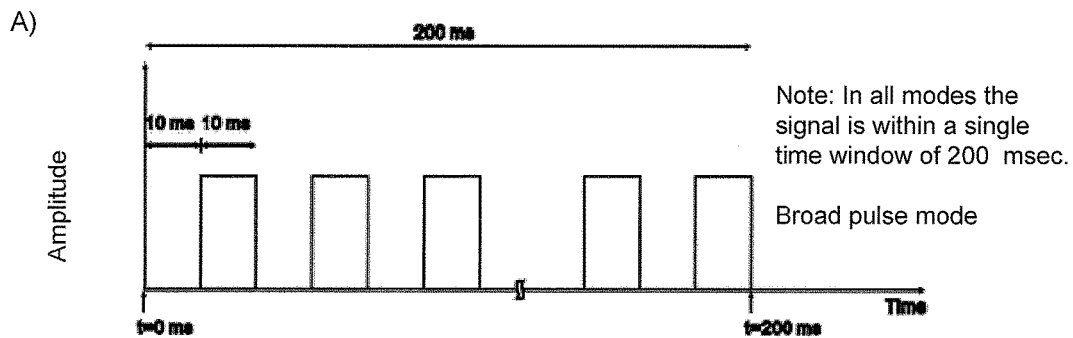
FIGS. 13A-13I are schematic illustrations of representative types of microwave pulse sequences that can be provided in accordance with particular embodiments of the present disclosure.
Figure 13B:
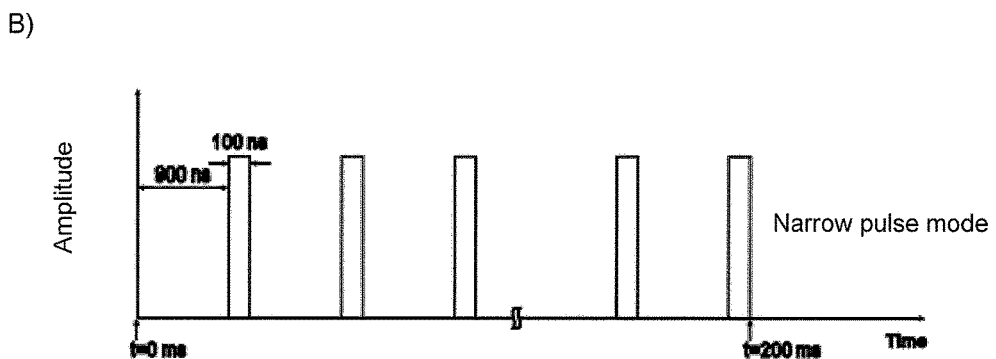
Figure 13C:
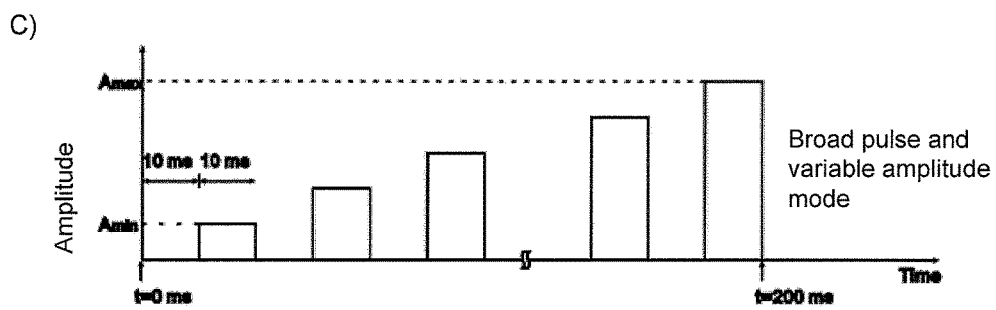
Figure 13D:
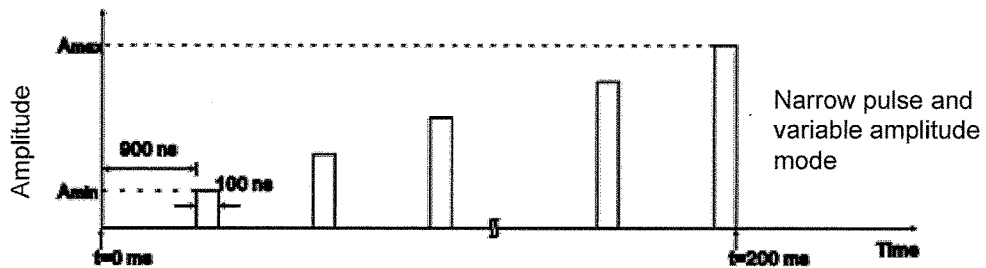
Figure 13E:
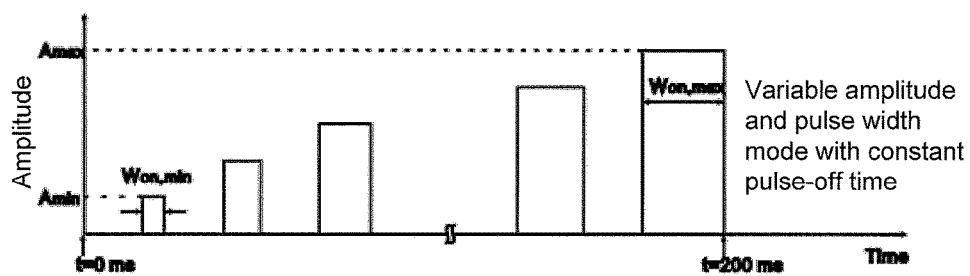
Figure 13F:
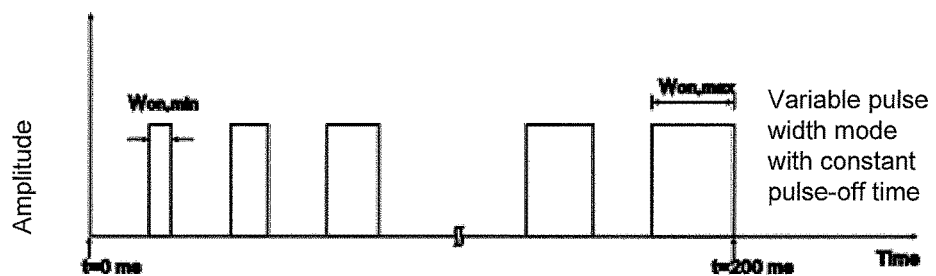
Figure 13G:
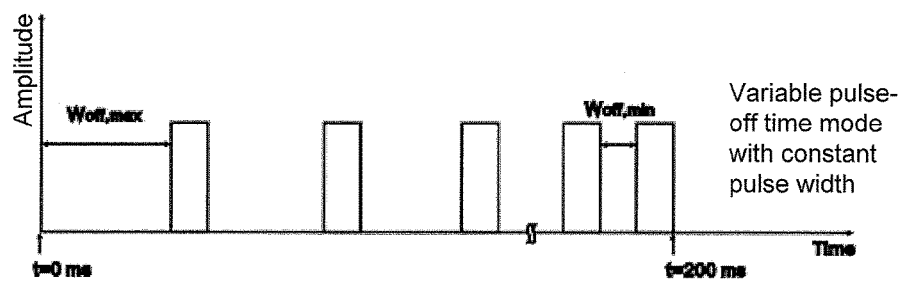
Figure 13H:
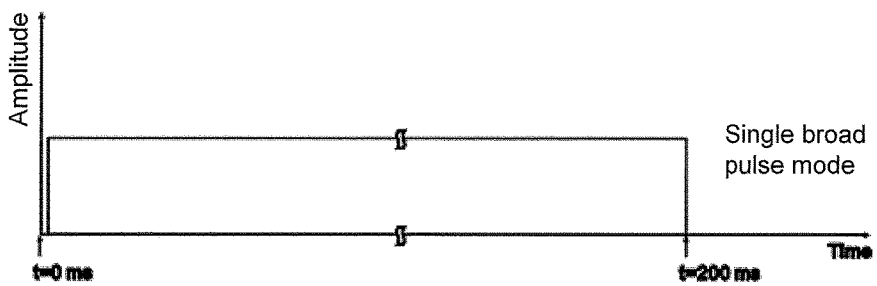
Figure 13I:
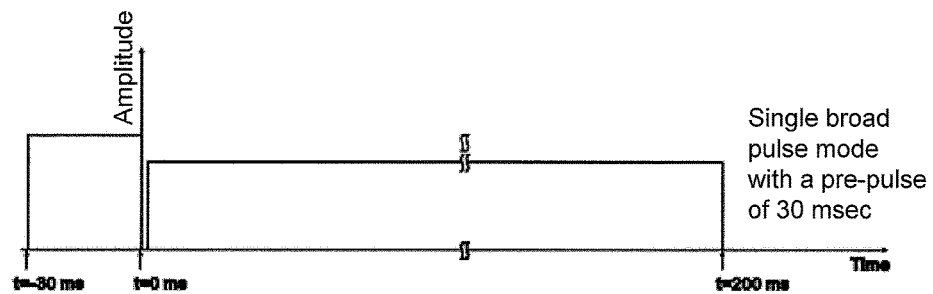

FIG. 11E is an image showing portions of a representative prototype sample preparation or fixation system 10 in accordance with an embodiment of the present disclosure. In an embodiment, the prototype system 10 utilizes a TWT amplifier that provides controlled excitation of specimens with microwave pulses as short as 100 nanoseconds to microseconds, for durations up to hundreds of milliseconds (or even continuous wave (CW)) while allowing access to power levels up to nearly 1 kW. A representative TWT was specified to operate over both ISM bands, 2.45 GHz and 5.8 GHz with a power at the fundamental frequency of at least 500 Watts. The microwave pulses can be controlled with nearly arbitrary pulse width, delay between pulses, and pulse amplitude; and all of these parameters can be altered during a single freezing event, so that the microwave energy can be matched precisely to the freezing front as it propagates through the sample.

The TWT has the advantage that it can provide high power over a broad frequency range. For pulses 100 nsec in duration (or less) the input signal must be modulated, either at the signal generator or with a PIN diode switch in series with the signal generator output. The design of the prototype system 10 enables a PIN fast modulation scheme, which is synchronized with a TWT suppression grid to eliminate the thermal noise prior to the experiment. The suppression grid is turned off immediately prior to freezing, and a computer controlled high power microwave pulse train is triggered to correspond with the actuation of a cryogenic coolant jet 220. Other embodiments in accordance with the present disclosure can utilize solid state microwave amplifiers instead of a TWT, in a manner understood by those of ordinary skill in the relevant art.

In various embodiments, the cryo-coolant jet 220 can be provided to the underside of the thermal energy transfer substrate 112 by way of a commercially available cryo-condenser. FIGS. 12A and 12B are images of a particular type of commercially available cryo-condenser suitable for providing a cryo-coolant jet 220 in accordance with an embodiment of the present disclosure.

FIGS. 13A-13I are schematic illustrations of representative types of microwave pulse sequences that can be provided in accordance with particular embodiments of the present disclosure. One or more pulse characteristics or parameters (e.g., pulse amplitude, inter-pulse interval, individual pulse duration, and/or other parameters) can be adjusted or dynamically changed or varied (e.g., in a selectable or programmable manner) during the provision, delivery, or application of a microwave pulse sequence or train. Some embodiments include or utilize a chirped pulse sequence, where a chirp pattern can dynamically accommodate impedance mismatch associated with impedance changes or variation resulting from rapid cooling of a capsule 110 and/or the sample(s), specimen(s), or fluid medium or media carried thereby. One or more "chirp recipes" can be determined (e.g., based upon experimental or simulated results) for particular sample types and/or volumes, where a given chip recipe corresponds or gives rise to desired, intended, or target sample vitrification properties or results.

In addition to the foregoing, multiple embodiments in accordance with the present disclosure avoid or substantially avoid thermal cooling of optical elements 55 such as a microscope objective, for instance, by way of application (e.g., selective delivery) of a gas (e.g., a room temperature or slightly heated dry gas such as Nitrogen or compressed dry air). In embodiments that include an immersion lens, which involve a fluid layer (e.g., a refractive index matching fluid) between a microscope objective and the capsule's cover 114, a selectively or programmably activated gas jet (e.g., a dry gas such as Nitrogen, which can be heated) can be directed toward or to the fluid layer at particular times, such as the onset of rapid cooling.

Aspects of particular embodiments of the present disclosure address at least one aspect, problem, limitation, and/or disadvantage associated with exiting sample preparation, fixation, or vitrification techniques. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, components, processes, or alternatives thereof, may be desirably combined into other different systems, components, processes, and/or applications. In addition, various modifications, alterations, and/or improvements may be made to various embodiments that are disclosed by a person of ordinary skill in the art within the scope and spirit of the present disclosure.

For example, a number of embodiments in accordance with the present disclosure need not be designed or suitable for microwave assisted cryo-fixation of samples, but can rather be designed for microwave assisted chemical fixation of samples. At least some of such embodiments can provide a support member other than a very high or extremely high thermal conductivity substrate 112 (e.g., a diamond or sapphire disk) on, as, or in very close proximity to a bottom surface of a sample cell 402. Microwave assisted chemical fixation embodiments can include microfluidic elements such as those described above to facilitate the introduction or circulation of one or more types of fluids (e.g., liquids or gases) such as chemical substances in a chamber 116, and hence the exposure of a sample carried thereby to one or more of such fluids.

As another example, certain embodiments in accordance with the present disclosure can include one or more groups or arrays of microfluidic microwave delivery chamber modules or sample cells 402 (e.g., a 2×2, 3×3, 4×4, or larger array of sample cells 402). Depending upon embodiment details, only one, a small number, or possibly none of the compartment interiors provided by the sample cells 402 can be configured for optical imaging at any given time (e.g., by way of selective displacement or positioning of a set of microscope objectives relative to individual sample cells 402 within the group or array of sample cells 402); or multiple or all compartment interiors of the sample cells 402 within the group or array of sample cells 402 can be configured for simultaneous optical imaging, such as by way of fiber optic bundles, optical lens assemblies, and image capture devices corresponding to each sample cell 402. In a sample cell group or array arrangement, microwave assisted cryo-fixation and/or microwave assisted chemical fixation can occur in a time sequenced or synchronized (e.g., essentially simultaneous) manner across multiple sample cells 402 within the group or array of sample cells 402, for instance, based upon or in response to one or more trigger events. Following fixation, individual sample cells 402 within the sample cell group or array can be transferred to one or more particular destinations, for instance, a cryo-destinations such as a dewar containing LN, or a high resolution cryo-microscopy system (e.g., an SEM or a SHIM). Alternatively, in certain embodiments, an entire group or array of sample cells 402 can be transferred to a predetermined destination, such as a dewar containing LN.

The preceding and other embodiments and embodiment variations are encompassed by the present disclosure, which is limited only by the following claims.

The invention claimed is:

1. A system for imaging a biological sample using a set of sample imaging wavelength ranges while preparing or fixing the biological sample, the system comprising:
 a sample capsule structure comprising:
  a thermal energy transfer substrate including a top face and a bottom face;
  a cover disposed opposite to the top face of the thermal energy transfer substrate, the cover comprising a material transparent or transmissive to the set of sample imaging wavelength ranges;
  a compartment disposed between the top face of the thermal energy transfer substrate and the cover, the compartment providing an internal volume in which the sample can be carried, and in which the sample is exposable to or carried by a fluid; and
  a set of microfluidic elements configured for introducing the fluid into and withdrawing the fluid out of the internal volume of the compartment;
 an electromagnetic signal source configured to generate microwave frequency signals in accordance with microwave signal parameters that are timed or synchronized relative to ice crystal growth dynamics;
  a microwave applicator coupled to the electromagnetic signal source and comprising a set of microwave signal delivery elements configured for exposing the sample within the compartment to microwave radiation generated in accordance with the microwave signal parameters while the sample is exposed to the fluid, wherein the microwave radiation has an average power density that avoids sample heating and an instantaneous power density that disrupts ice crystal nucleation events, and wherein the microwave radiation arrests initial ice crystal nucleation events in the sample within tens of microseconds; and
 a cryogenic cooling unit configured for selectively directing a cryogenic coolant jet to the bottom face of the thermal energy transfer substrate while the microwave applicator exposes the sample within the compartment to the microwave radiation during cryogenic cooling of the sample, wherein the thermal energy transfer substrate has a very high or extremely high thermal conductivity that enables cryogenic cooling of the substrate at a rate greater than approximately 5,000 degrees/sec.

2. The system of claim 1, wherein the sample capsule is configured to facilitate at least one of microwave assisted chemical sample fixation and microwave assisted cryogenic sample fixation.

3. The system of claim 2, wherein the thermal energy transfer substrate disposed beneath the sample and having a bottom face to which the cryogenic coolant jet can be directed to jet freeze the sample extremely rapidly while the microwave applicator exposes the sample within the compartment to microwave radiation.

4. The system of claim 3, wherein the sample capsule includes at least one freeze fracture initiation element configured for facilitating in-situ freeze fracturing of the sample.

5. The system of claim 4, wherein the cryogenic cooling unit is configured for supplying the cryogenic coolant jet and directing the cryogenic coolant jet to a bottom face of the thermal energy transfer substrate that is below the sample, such that the sample is flash frozen by way of extremely rapid transfer of thermal energy through the thermal energy transfer substrate to the cryogenic coolant jet.

6. The system of claim 5, wherein the microwave radiation is provided in a manner that disrupts water molecule pentamer cluster formation to vitrify portions of the sample during ultra-rapid freezing.

7. The system of claim 6, wherein the microwave radiation is provided in a manner that results in a vitrification depth within the compartment of up to approximately tens of microns.

8. The system of claim 3, wherein the microwave applicator is disposed above the sample.

9. The system of claim 3, wherein the thermal energy transfer substrate comprises diamond or sapphire.

10. The system of claim 3, wherein top face of the thermal energy transfer substrate forms a bottom surface of the interior of the sample capsule, on which the sample can be grown or placed.

11. The system of claim 1, wherein the microwave radiation is provided at a frequency of between approximately 2 GHz and approximately 18 GHz.

12. The system of claim 11, wherein the microwave radiation is provided at a frequency of approximately 2.45 GHz, 5.8 GHz, 10 GHz, or a combination thereof.

13. The system of claim 1, wherein the microwave radiation is provided by way of pulsed microwave signals having a high peak or instantaneous power and a low average power.

14. The system of claim 1, wherein the compartment and the microwave applicator are carried or supported by a dielectric substrate that carries conductive traces configured for providing microwave signals to the microwave applicator.

15. The system of claim 14, wherein the dielectric substrate additionally carries at least one of a set of microwave functional elements and a set of microwave coupler elements that are electrically couplable to the microwave applicator.

16. The system of claim 15, wherein (a) the set of microwave functional elements includes at least one of matching devices, a balun, a set of phase shifters, a set of power dividers, a set of isolators, a set of microwave opens, a set of microwave shorts, a set of microwave gaps, a set of microwave slots, a set of vias, a set of couplers couplers, a set of controlled length and controlled impedance transmission line elements, a set of microwave resistors, a set of microwave capacitors, and a set of inductors, and (b) the set of microwave coupler elements includes at least one of metal contact elements and associated mechanical pressure or force application devices that establish electrical signal communication between metal-to-metal contacts, intermediate conductive film(s) between metal-to-metal contacts, gap feeds, and gap couplers.

17. The system of claim 1, wherein the sample capsule structure is shaped and dimensioned to at least substantially match the size of a standard optical microscopy slide.

18. The system of claim 17, wherein the sample capsule structure is shaped and dimensioned for integration into an optical microscope stage or platform structure.

19. The system of claim 1, wherein the microwave applicator comprises a support member that is shaped and dimensioned to at least substantially match the size of an optical microscopy slide coverslip, and wherein the support member carries a patterned set of excitation elements that serve as electrodes by which microwave energy can be provided to internal portions of the compartment.

20. The system of claim 1, wherein the system further comprises (a) a membrane disposed between the cryogenic coolant jet and the bottom face of the thermal energy transfer substrate and which is pierceable by the cryogenic coolant jet, (b) a shutter mechanism configured to selectively isolate the thermal energy transfer substrate from the cryogenic coolant jet, or (c) a displacement mechanism configured for displacing the cryogenic coolant jet toward the thermal energy transfer substrate.

21. The system of claim 1, wherein the set of microfluidic elements includes an internal laminar flow region that forms at least portions of the internal volume of the compartment, and across which fluid flow to which the sample is exposed can occur in at least an approximately laminar manner.

22. The system of claim 1, wherein the sample capsule structure comprises a molded microfluidic cell that includes the set of microfluidic elements.

23. The system of claim 1, further comprising an optical imaging system configured for receiving or capturing an image of the sample within the compartment.

24. The system of claim 23, wherein the optical imaging system is configured for receiving or capturing an image of the sample within the compartment while the sample is exposed to the fluid and/or while the sample is exposed to the microwave radiation.

25. The system of claim 23, wherein the optical imaging system comprises a set of optical microscope objective lenses and an optical microscope platform configured for supporting the sample capsule structure such that an objective lens within the set of objective lenses can focus on a portion of the sample within the compartment.

26. The system of claim 1, wherein the sample capsule structure includes at least one set of fiducial markers to facilitate correlative microscopy procedures.

27. The system of claim 26, wherein the sample capsule structure includes a first set of fiducial markers internal to the compartment and a second set of fiducial markers external to the compartment.

28. The system of claim 1, wherein the system comprises multiple sample capsule structures, each of which is configured for exposing a distinct sample to a fluid simultaneous with exposing the sample to microwave radiation.

29. The system of claim 28, wherein each of the multiple sample capsule structures is configured to facilitate at least one of microwave assisted chemical sample fixation and microwave assisted cryogenic sample fixation.

30. A method for preparing or fixing a sample by way of ultra-rapid freezing, comprising:

providing a sample capsule structure that includes a compartment having an internal volume in which the sample can be carried, and in which the sample is exposed to or carried by a fluid;

generating microwave frequency signals in accordance with microwave signal parameters that are timed or synchronized relative to ice crystal growth dynamics; and exposing the sample capsule to a cryogenic coolant jet to rapidly cool the sample during a sample vitrification process while simultaneously exposing the sample capsule to microwave radiation corresponding to the microwave frequency signals in a manner that disrupts initial ice crystal nucleation events within the compartment within tens of microseconds and which avoids adversely affecting vitrification of the sample to thereby provide a vitrification depth within the compartment of at least approximately tens of microns, wherein the microwave radiation has an average power density that avoids sample heating and an instantaneous power density that disrupts ice crystal nucleation events in the sample.

31. The method of claim 30, wherein the microwave radiation comprises pulsed microwave signals having a high peak or instantaneous intensity, and a low average intensity.

32. The method of claim 30, wherein the sample is carried between an upper surface of the compartment and a lower surface of the compartment, and wherein the cryogenic coolant jet is configured to cool the lower surface of the compartment extremely rapidly, and the microwave radiation is provided above or from the upper surface of the compartment.

33. The method of claim 30, further comprising passing the fluid through the compartment by way of a set of microfluidic elements.

34. The method of claim 30, further comprising:
providing at least one set of fiducial markers carried by the sample capsule structure; and
determining a set of spatial positions corresponding to particular portions of the sample relative to the at least one set of fiducial markers.

35. The method of claim 30, further comprising freeze fracturing the sample while the sample is carried within the compartment.

* * * * *